US008573980B2

(12) United States Patent
Wetmore et al.

(10) Patent No.: US 8,573,980 B2
(45) Date of Patent: *Nov. 5, 2013

(54) APPARATUS, SYSTEM, AND METHOD FOR MODULATING CONSOLIDATION OF MEMORY DURING SLEEP

(71) Applicant: Sheepdog Sciences, Inc., San Francisco, CA (US)

(72) Inventors: Daniel Z. Wetmore, San Francisco, CA (US); Todd O. Anderson, San Francisco, CA (US); Robert J. Barretto, New York, NY (US); Alexander F. A. Butterwick, San Francisco, CA (US); Lia Siebert, San Francisco, CA (US)

(73) Assignee: Sheepdog Sciences, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/770,826

(22) Filed: Feb. 19, 2013

(65) Prior Publication Data

US 2013/0190556 A1 Jul. 25, 2013

Related U.S. Application Data

(63) Continuation-in-part of application No. 13/439,715, filed on Apr. 4, 2012, now Pat. No. 8,382,484.

(60) Provisional application No. 61/471,526, filed on Apr. 4, 2011, provisional application No. 61/744,826, filed on Oct. 3, 2012.

(51) Int. Cl.
*G09B 9/00* (2006.01)

(52) U.S. Cl.
USPC .......................................... 434/236; 434/238

(58) Field of Classification Search
USPC .................................. 434/156–157, 236, 238
See application file for complete search history.

(56) References Cited

U.S. PATENT DOCUMENTS

| | | |
|---|---|---|
| 3,884,218 A | 5/1975 | Monroe |
| 4,008,714 A | 2/1977 | Silva et al. |
| 4,203,452 A | 5/1980 | Cohen |
| 4,928,704 A | 5/1990 | Hardt |
| 5,259,390 A | 11/1993 | MacLean |
| 5,339,826 A | 8/1994 | Schmidt et al. |
| 5,447,166 A | 9/1995 | Gevins |
| 5,551,879 A | 9/1996 | Raynie et al. |
| 5,722,418 A | 3/1998 | Bro |

(Continued)

OTHER PUBLICATIONS

Antony et al.; Enhancing motor learning for a melodic sequence via sleep reactivation; Program No. 826.12; 2011 Neuroscience Meeting; Washington, DC; Nov. 16, 2011 (presentation abstract).

(Continued)

*Primary Examiner* — Robert J Utama
(74) *Attorney, Agent, or Firm* — Shay Glenn LLP

(57) ABSTRACT

Devices, systems and methods to modify memory and/or cognitive function by delivering a sensory stimulus paired with learned material at opportune physiological periods during sleep. For example, described herein are systems, methods and devices to enhance a user's cognitive function in such areas as memorization and learning. A machine (e.g., a system or device) may be used to identify opportune periods of the sleep cycle and to deliver a stimulus during specific phases of the sleep cycle to facilitate or interrupt memory consolidation. In some variations the machine records ambient sensory inputs during awake acquisition or reinforcement/relearning and replays all or an extracted form of the ambient sensory stimuli a specified portion of the user's sleep.

15 Claims, 23 Drawing Sheets

(56) References Cited

U.S. PATENT DOCUMENTS

| | | | |
|---|---|---|---|
| 5,940,801 | A | 8/1999 | Brown |
| 6,157,857 | A | 12/2000 | Dimpfel |
| 6,338,044 | B1 | 1/2002 | Cook et al. |
| 6,439,474 | B2 | 8/2002 | Denen |
| 6,625,485 | B2 | 9/2003 | Levendowski et al. |
| 6,626,676 | B2 | 9/2003 | Freer |
| 6,878,121 | B2 | 4/2005 | Krausman et al. |
| 7,041,049 | B1 | 5/2006 | Raniere |
| 7,190,995 | B2 | 3/2007 | Chervin et al. |
| 7,580,742 | B2 | 8/2009 | Tan et al. |
| 7,749,154 | B2 | 7/2010 | Cornel |
| 8,029,431 | B2 | 10/2011 | Tononi |
| 8,055,348 | B2 | 11/2011 | Heruth et al. |
| 8,382,484 | B2 | 2/2013 | Wetmore et al. |
| 2002/0103428 | A1 | 8/2002 | deCharms |
| 2002/0103429 | A1 | 8/2002 | deCharms |
| 2003/0004423 | A1 | 1/2003 | Lavie et al. |
| 2004/0131998 | A1 | 7/2004 | Marom et al. |
| 2005/0043652 | A1 | 2/2005 | Lovett et al. |
| 2005/0065452 | A1 | 3/2005 | Thompson |
| 2006/0106275 | A1 | 5/2006 | Raniere |
| 2006/0257834 | A1 | 11/2006 | Lee et al. |
| 2007/0207220 | A1 | 9/2007 | Luedtke et al. |
| 2007/0270706 | A1 | 11/2007 | Merilainen et al. |
| 2008/0004660 | A1 | 1/2008 | Assaf et al. |
| 2008/0138783 | A1 | 6/2008 | Karkanias et al. |
| 2008/0234785 | A1 | 9/2008 | Nakayama et al. |
| 2009/0198145 | A1 | 8/2009 | Chow |
| 2009/0214060 | A1 | 8/2009 | Chuang et al. |
| 2009/0281408 | A1 | 11/2009 | Lee et al. |
| 2009/0295911 | A1 | 12/2009 | Grim, III et al. |
| 2010/0068146 | A1 | 3/2010 | Luther-Forsstrom et al. |
| 2010/0087701 | A1 | 4/2010 | Berka et al. |
| 2010/0090835 | A1 | 4/2010 | Liu et al. |
| 2010/0099954 | A1 | 4/2010 | Dickinson et al. |
| 2010/0234752 | A1 | 9/2010 | Sullivan et al. |
| 2010/0331630 | A1 | 12/2010 | Odio |
| 2011/0015469 | A1 | 1/2011 | Walter et al. |
| 2011/0118534 | A1 | 5/2011 | Baror et al. |
| 2011/0160619 | A1 | 6/2011 | Gabara |

OTHER PUBLICATIONS

Benington et al.; Stimulation of A1 adenosine receptors mimics the electroencephalographic effects of sleep deprivation; Brain Research; 692; pp. 79-85; Sep. 18, 1995.
Born et al.; Sleep to remember; The Neuroscientist; 12(5); pp. 410-424; Oct. 2006.
Carr et al.; Hippocampal replay in the awake state: a potential substrate for memory consolidation and retrieval; Nature neuroscience; 14(2); pp. 147R153; Feb. 14, 2011 (author manuscript).
Creery et al.; Sleep reactivation enhances location memory; Program No. 824.01; 2011 Neuroscience Meeting; Washington, DC; Nov. 16, 2011 (presentation abstract).
Diekelmann et al.; Labile or stable: opposing consequences for memory when reactivated during waking and sleep. Nature Neuroscience; 14(3); pp. 381-386; Mar. 2011.
Diekelmann et al.; The memory function of sleep; Nature reviews Neuroscience; 11; pp. 114-126; Feb. 2010.
Feinberg et al.; Flurazepam effects on slow-wave sleep: stage 4 suppressed but numbers of delta waves constant; Science; 198(4319); pp. 847-848; Nov. 25, 1977.
Foster et al.; Reverse replay of behavioural sequences in hippocampal place cells during the awake state; Nature; 440; pp. 680-683; Mar. 30, 2006.
Gais et al.; Learning-dependent increases in sleep spindle density; The Journal of Neuroscience; 22(15); pp. 6830-6834; Aug. 1, 2002.
Godschalk et al.; Slow wave sleep and a state resembling absence epilepsy induced in the rat by y-hydroxybutyrate; European journal of pharmacology; 44(2); pp. 105-111; Jul. 15, 1977.
Idzikowski et al.; 5-Hydroxytryptamine-2 antagonist increases human slow wave sleep; Brain Research; 378(1); pp. 164-168; Jul. 16, 1986.
Ji et al.; Coordinated memory replay in the visual cortex and hippocampus during sleep; Nature neuroscience; 10(1); pp. 100-107; Jan. 2007.
Lee et al.; Memory of sequential experience in the hippocampus during slow wave sleep; Neuron; 36(6); pp. 1183-1194; Dec. 19, 2002.
Marshall et al.; Boosting slow oscillations during sleep potentiates memory; Nature; 444; pp. 610-613; Nov. 30, 2006.
McCarley; Neurobiology of REM and NREM sleep; Sleep medicine; 8(4); pp. 302-330; Jun. 2007.
Ozen et al.; Transcranial electric stimulation entrains cortical neuronal populations in rats; The Journal of neuroscience; 30(34); pp. 11476-11485; Aug. 25, 2010.
Pavlik et al; Using a model to compute the optimal schedule of practice; Journal of experimental psychology Applied; 14(2); pp. 101-117; Jun. 2008.
Perspectives on Neuroscience and Behavior; The Neuroscientist; 16(2); pp. 116-117; Apr. 2010.
Rasch et al.; Odor cues during slow-wave sleep prompt declarative memory consolidation; Science; 315(5817); pp. 1426-1429; Mar. 9, 2007.
Rudoy et al.; Strengthening individual memories by reactivating them during sleep; Science; 326(5956); pp. 1079; Nov. 20, 2009 (author manuscript).
Stickgold et al.; Sleep and memory: The ongoing debate; Sleep; 28(10); pp. 1225-1227; Oct. 2005.
Wagner et al; Sleep inspires insight; Nature; 427(6972); pp. 352R355; Jan. 22, 2004.
Walter; Getting Smarter While You Sleep; Sleep Review; Oct. 2008; retrieved from the Internet; http://www.sleepreviewmag.com/issues/articles/2008-10_03.asp; 6 pages.
Wilson et al.; Dynamics of the hippocampal ensemble code for space; Science; 261; pp. 1055-1058; Aug. 20, 1993.
Wilson et al.; Reactivation of hippocampal ensemble memories during sleep; Science; 265; pp. 676-679; Jul. 29, 1994.
Wilson; Hippocampal memory formation, plasticity, and the role of sleep; Neurobiology of learning and memory; 78(3); pp. 565-569; Nov. 2002.
Yeshurun et al.; The privileged brain representation of first olfactory associations; Current biology; 19(21); pp. 1869R1874; Nov. 17, 2009.
Ziegler et al.; Reversal of slow-wave sleep by benzodiazepine antagonist Ro 15/1788; Lancet; 326(8453); pp. 510; Aug. 31, 1985.

APPARATUS, SYSTEM, AND METHOD FOR MODULATING CONSOLIDATION OF MEMORY DURING SLEEP

CROSS REFERENCE TO RELATED APPLICATION

This application claims priority as a continuation-in-part to U.S. patent application Ser. No. 13/439,715, filed Apr. 4, 2012, and titled "APPARATUS, SYSTEM, AND METHOD FOR MODULATING CONSOLIDATION OF MEMORY DURING SLEEP," now Publication No. 2012-0251989, which claims priority to U.S. Provisional Patent Application No. 61/471,526, filed Apr. 4, 2011, and titled "APPARATUS, SYSTEM, AND METHOD FOR MODULATING CONSOLIDATION OF MEMORY DURING SLEEP," each of which is herein incorporated by reference in its entirety.

This application also claims priority to U.S. Provisional Patent Application No. 61/744,826, filed Oct. 3, 2012, and titled "LEARNING DATABASE AND SCHEDULER SYSTEM AND METHODS FOR MODULATING CONSOLIDATION OF MEMORY DURING SLEEP," which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Described herein are devices, systems and methods for modulating (including enhancing and/or disrupting) cognition and/or memory. More particularly, described herein are devices, systems and methods for interfacing computerized platforms to enhance human cognition during sleep.

BACKGROUND

Proper memory function requires encoding of a memory during learning, consolidation of the memory in the hours and days that follow, and retrieval of the learned content during testing.

Memory consolidation is the process whereby the brain transfers memories to long-term storage. Consolidation of memories occurs primarily during sleep. Deep, or 'slow-wave' sleep (SWS), is particularly important for consolidating long-term memories. Recent advances in the fields of neurobiology, psychology, and sleep research have characterized the important relationship between sleep and memory.

Sleep is required for normal memory consolidation and reduced sleep quality or quantity disrupts memory function. In people, memory and other higher cognitive functions can be improved by increasing sleep quantity or sleep quality. Intensive training or learning causes an increase in the amount of SWS sleep during a subsequent night, suggesting that this phase of sleep is required for memories to be consolidated. In rodents, neurobiological studies have shown that patterns of activity among neurons in the hippocampus, a key brain region for memory, occur in a predictable and sequential pattern when a rodent is exploring a maze or other environment. The spatial memory represented by this experience is thought to be consolidated during sleep. Electrophysiological recordings during SWS have been used to identify 'replay' of the patterns of neural activity observed during previous experience, suggesting that replay is an important mechanism for consolidation of memories to long-term storage. Interruption of replay during sleep by electrical stimulation disrupts memory formation.

There are several phases of sleep that occur in a repeated cycle. Sleep phases can be identified by differences in brain activity and physiology, including variation in heart rate, body temperature, and arousal threshold. In humans, sleep is generally described according to a cycle in which rapid eye movement (REM) sleep is followed by non-REM sleep that generally proceeds sequentially through phases S1, S2, S3, and S4. Phases S1 and S2 are generally referred to as light sleep, and phases S3 and S4 are generally referred to as deep or 'slow-wave' sleep (SWS).

Normal cognitive function requires sufficient and well-structured sleep. Cognitive impairment due to sleep abnormalities occurs in individuals with neurodevelopmental disorders such as Down syndrome, neurodegenerative disorders such as Alzheimer's disease, various forms of insomnia, sleep apnea, and other pathological conditions. Similarly, reduced memory function unrelated to disease occurs with normal aging, overnight shift work, drug or alcohol use, and other causes of sleep impairment or sleep disruption. For these various forms of cognitive dysfunction, strategies to alleviate or mitigate cognitive deficits with pharmaceutical, educational, and behavioral interventions have received significant attention but have not adequately addressed cognitive deficits. New methods for improving the lives of those with intellectual disabilities, age-related cognitive decline, and other forms of learning disability by improving memory and cognitive function are desired. Moreover, healthy, typically-developed students of all ages would benefit from a method for enhancing memory consolidation and thus long-term memory retention.

The systems, methods and devices described herein may relate to augmenting or disrupting memory consolidation. These systems, methods and devices may allow the application of techniques to improve learning and memory non-invasively and without drugs and may engage memory consolidation processes that are active during sleep.

Although there is some academic work examining the presentation of sensory stimulus cues during sleep, this work has, to date, not been applied to a home setting in a manner that allows application of these techniques by an individual user. For example, in the first publication to report this effect, contextual presentations of olfactory cues during a prior learning event, when re-exposed during slow-wave sleep, were shown to improve the retention of memories formed during the learning event (Rasch, B., Büchel, C., Gais, S., and Born, J., 2007, Odor cues during slow-wave sleep prompt declarative memory consolidation. Science, 315, 1426-1429). In the simplest form of this technique, memory may be enhanced by (1) pairing learning with a sound or smell, (2) monitoring sleep during a subsequent night's sleep or nap, (3) detecting slow-wave (deep) sleep, and (4) re-presenting the sensory cue. Published studies of controlled, clinical studies of this technique have reported up to about 30% improvements in memory in healthy young adults (Diekelmann, S., Büchel, C., Born, J., and Rasch, B., 2011, Labile or stable: opposing consequences for memory when reactivated during waking and sleep. Nature neuroscience). Unfortunately, these studies provide little guidance on the application of these results in a home or user-applied setting, outside of a controlled laboratory setting.

Further, additional research has shown that misapplication of these techniques may lead instead to a decrease in memory.

In contrast to the studies that reported enhanced memory after sensory re-presentation during sleep, re-presenting the sensory stimulus from training to the subject during wakefulness leads to a reduction in memory performance (Diekelmann et al., 2011). This finding also suggests methods for abolishing undesired memories such as those associated with traumatic events that lead to post-traumatic stress disorder (PTSD). Memory re-consolidation occurs when a memory that has been successfully stored in long-term memory is recalled. Maintenance of the memory in long-term memory after this event of memory recall requires active neurobiological processes to re-consolidate the stored memory trace. Accordingly, methods that selectively disrupt memories that are maladaptive, related to psychiatric conditions, or otherwise unwanted would be of great benefit to many.

Memory consolidation can also be reduced by disrupting sleep or by depriving a subject of sleep. Studies in humans and animals have shown that sleep deprivation or disruption of sleep after a training event lead to reduced memory performance.

Systems and methods for modulating memory consolidation during sleep have been previously described, but these disclosures do not describe how to select, prioritize, and schedule contextual sensory stimuli to be presented to a subject in order to achieve effective modulation of memory consolidation for multiple learning and sleep consolidation events across one or more days and nights. The systems and methods for configuring, populating, and querying a learning database of training content and contextual sensory stimuli described here are useful for selecting, prioritizing, and scheduling memory consolidation events.

SUMMARY OF THE DISCLOSURE

Described herein are devices, systems and methods to deliver a sensory stimulus or stimuli at opportune physiological periods to enhance the user's cognitive function in such areas as memorization and learning. A machine (e.g., a system or device) may be used to identify opportune periods of the sleep cycle and to deliver a stimulus during specific phases of the sleep cycle, for example to facilitate or interrupt memory consolidation. In other embodiments, the machine records ambient sensory inputs such as those detected by auditory, somatosensory, olfactory, gustatory, visual, vestibular, or sensory systems during a period of learning and stores these stimuli in a database for subsequent re-presentation during sleep.

The devices and systems may determine the phase of sleep for a user as part of an integrated device or system that also determines the sensory stimulus and presents the sensory stimulus during training and/or sleep. The determination of sleep phase by monitoring an individual during sleep may be referred to as sleep staging. Sleep staging may be performed using the traditional Rechtschaffen & Kales rules, which classify sleep into six separate stages: wake, rapid eye movement (REM) sleep, S1 (light sleep), S2 (light sleep), S3 (deep sleep), and S4 (deep sleep). Alternative systems for sleep staging have been described and are known to those skilled in the art. Techniques for monitoring physiological changes associated with different stages of sleep may include electroencephalography (EEG) recordings of brain activity, electrooculagraphy (EOG) of eye movement and ocular muscle contractions, electrocardiography (ECG) of heart beats, as well as heart rate or heart rate entropy, respiratory rate, body temperature, eye or body movements (actigraphy), and other techniques. A variety of devices and sensors can be used to monitor physiological changes associated with sleep phases and may be incorporated into the devices, systems and methods described herein.

In addition to sensing the phase of sleep, the devices and systems may also deliver a stimulus, such as an electrical or sensory stimulus, for the purpose of modulating the phase of a user's sleep or modulating the quality of sleep and/or the quality or intensity of brain rhythms during a particular phase of sleep. In particular, the stimulus may mimic or repeat a stimulus that was intentionally or inadvertently paired with the "learning" of the memory to be modulated.

Learning of any appropriate material may be modulated (e.g., enhanced, inhibited) by the systems and methods described herein. For example, in some variations, the devices and systems described herein enhance learning of material to be compiled for a user from several sources that may include: 1) material entered into a computing device by the user or a third party that may be stored locally on the device or stored on a remote server or intermediate device; 2) material that may be in a variety of electronic formats that can be uploaded by the user or third party to a computing device for storage through the Internet on a remote server or on an intermediate device; 3) material chosen by the user from a pre-determined set of training material that may be provided by a third party or the device; 4) material that may be generated based on the user's location at a particular time or 'check-in' by a service having functionality similar to that of Gowalla or Foursquare; 5) material generated based on the user's interests as indicated by the user, by a third party, or by data mining; 6) material that may be supplied by a third party such as a teacher, work colleague, friend, advertiser, or other individual or entity; or 7) material supplied by other suitable means appreciated by one skilled in the art, that may be currently known or hereafter developed.

In some variations, the devices and systems described herein may be networked such that user information and device control can be managed through interactions with any combination of the devices. Exemplary interactions include: 1) the ability for the user to select physiological recording settings from a personal computer or other machine, which further synchronizes information with a base station, 2) the ability for sleep quality information acquired from a base station to be stored and analyzed on a personal computer, and/or 3) the ability for remotely communicating with the base station from a learning environment.

In one embodiment, the system or device has the ability to be networked with remote servers, other nearby components of the system or device, and third party servers and devices. The networking of devices offers additional functionality, ease of use, physiological sensing, or data management as each networked or otherwise connected device may have different advantages in different phases of the training program. For example, networking of devices may permit data on learned material, past sleep stimulus exposures, awake sensory exposures, cognitive performance, or event attendance at a particular location, or event, such as in a lecture hall, to be used to deduce probable stimuli exposures or training content of interest.

In general, the devices described herein may be controlled by the user. Thus, any of the variations described herein may be configured so that a user may activate the device (e.g., trigger the learning/training session and later sleep consolidation sessions) without the need for additional intervention (e.g., from a technician, or the like). For example, a user may control the device through the machine's user interface; said interface may exist on the device, through the Internet on a remote server, through a web-based software application, or through an intermediate device. An example interaction between the user and the device through the user interface may be in selecting which previous learned items the user wishes to further practice, or in defining the importance of a single or group of learned item(s).

In some variations, a user or third party may receive feedback concerning various aspects of the device's function, including but not limited to the quality of sleep, learning content presented, sensory cues presented, and memory function. This feedback may be generated in real-time or at a delay. The feedback may be delivered to the user or a third party by various routes including, but not limited to sensory feedback such as by visual, auditory, or haptic stimuli or information displayed on a computer screen, handheld device, or other electronic device.

In general, the stimulus applied during learning and again during sleep consolidation may be any appropriate sensory stimulus. In particular, stimuli that are below the threshold for waking the user (e.g., non-distracting sensory stimuli) are used. The mode of the stimuli may include one or more of: audible, tactile (including somatosensory), olfactory, vestibular, gustatory, visual, or the like. In some variations, the system or device includes a number of predetermined sensory stimuli, and may choose from this pool of sensory stimuli to pair the particular, specific sensory stimuli with a particular training session and/or with a particular piece of information to be learned. In some variations, the sensory stimuli may be multi-modal.

In some variations, the system or devices may be configured to record and provide sensory stimuli that are copied or extracted from ambient or environmental sensory information not controlled by the invention. For example, the system or devices described herein may include an ambient recorder ("sensory recorder") for recording or extracting background sensory stimuli from during a training period. In some variations the system may receive information on sensory stimulus provided by audio players, computers, television/video players, and the like. In some variations the system or device may communicate electronically with such peripherals to determine what sensory stimulus was being presented by these peripherals during the learning phase.

The device and systems described herein may interface with a networked device to enable selection of sensory information from a database. The content of such a database could be populated from user-uploaded content or from third parties through a web-browser or similarly effective widget. Third parties may include educational entities and socially-derived networks.

In some variations, the systems or devices may also include the ability to deliver a reconstruction of recorded ambient stimuli, or a complimentary percept, such as one that has undergone signal processing to identify signals of interest or high variance, during targeted phases of the users' sleep cycle.

In general, the devices and systems described herein may be configured for use with one or more user. For example, a system or device may keep track of which users receive which stimuli at which time and sleep phase. As mentioned, the system and device may be configured to ensure that a particular stimulus is paired with a particular training session and/or material to be learned for a particular user. Thus, a device may be configured to determine user identity to help insure that the same user receives novel stimuli for new training sessions/new material. Thus, in some variations the system may use biometric data to determine/confirm user identity. In some variations the systems and/or devices may request user name and/or password/identity codes. Examples of biometric data may include fingerprint, or other biometric identifiers. In some variations the system is configured to assume that it will only be used for a single user. The pool of sensory stimuli may be finite, and in some variations the device or system may indicate when the maximum number of sensory stimuli has been used. In some variations, the system or device may be configured so that a sensory stimuli module may be removed/added/replaced to provide new or additional sensory stimuli for pairing with training sessions or learned material.

In some embodiments, learning material is presented by the machine or by software on a computer, phone, or other electronic device (currently known or hereafter developed) at the same time as sensory stimuli or in close temporal relation to the sensory stimuli.

Physiological changes that occur in response to presentations of sensory stimuli may be used for feedback modulation of the delivered stimuli. These physiological changes may be monitored during sleep, during wakefulness, or during training or testing. The variety of physiological features that can be monitored will be appreciated by one skilled in the art and may include brain rhythms that relate to attention, memory processing, or other cognitive function; heart rate, heart beat entropy, or ECG signals; respiratory rate or entropy; pulse oximetry (blood oxygen content, $SpO_2$); galvanic skin responses (GSRs); arousal levels; eye gaze; posture; muscle tone; or other physiological signals of interest or appreciated by one skilled in the art.

Desirable feedback in response to identified physiological features may include, but are not limited to, modifying the intensity, modality, or other aspects of sensory stimulus presentation; modifying the rate, content, or difficulty of training content; delivering a reminder cue to modify attention, gaze, or other aspects of cognition or physiology; or delivering stimuli to affect brain rhythms and/or cognitive processes, including but not limited to increasing the frequency, intensity, or spatial extent of slow wave (delta) rhythms. Moreover, stimuli may be modulated to recapitulate prior physiological activity measured during past successful sleep sessions. For example, a strong stimulus intensity could negatively affect the stability of the current sleep phase, whereas a weak stimulus intensity may not be sufficiently salient to warrant memory consolidation. By monitoring the effect on sleep, memory, or other aspects of physiological function, the present invention can choose the appropriate stimulus parameters for a particular user given a particular set of physiological measurements.

Third parties may be granted access to control the device as well as gather information from the device through the Internet on a remote server, or through an intermediate device. A third party may provide specific instructions as to how the device is to interact with the user. In some variations a third party may receive information such as durations of sleep states or assessments of memory performance.

Third parties may be granted access to submit data to components of the device to improve the ability of the device to aggregate learning content and to integrate the device's capabilities with the third party's objectives, as well as gather information from the device through the Internet on a remote server, through a web-based software application, or through any suitable intermediate device currently known or hereafter developed.

One variation of a device or system is configured to aid or enhance the development of a skill. For example, in some variations, the system may be configured to aid in learning foreign languages or technical software languages. Training sessions may be paired with a sensory stimulus. In general, the sensory stimulus is distinct from the material being trained. For example, the sensory stimulus may be a primitive (e.g., a scent, tone, touch, or the like) that does not, in the absence of being paired with the training session, evoke the trained material.

In general, the systems or devices described herein may be used to train virtually any subject matter. For example, the systems or devices and/or related methods may be used for learning vocational trade skills, such as, for example, training of automotive mechanics. In one variation, the systems or devices may be used for test preparation for standardized tests such as those required for admission to primary or secondary schools, universities, post-graduate programs, or other academic pursuits; tests required for admittance to a specific professional group including but not limited to the state bar exam for lawyers, the Certified Public Accountant (CPA) exam for accountants, the medical board exams for doctors, the Series 7 exams for brokers, or other professional tests or exams that would be known to one skilled in the art of test preparation. In some variations, the systems and devices described herein may be used for experiential learning such as occurs during residency training for medical doctors, strategy learning for professional athletes (such as learning a playbook for football players), or other applications appreciated by one skilled in the art for which learning by observing and learning by doing are fundamental. Learning involving rote memorization may also be enhanced using the devices, systems and methods described herein.

Thus, the systems, devices and methods described herein may be particularly useful for repeated learning using these techniques. The system, devices and methods described herein are particularly well suited for repeated use where it is desirable or necessary to enhance learning of more than one piece of information or task skill. Because repeated use requires the use of multiple stimulations, repeated at one or more times following a learning session, a device useful for repeated learning is typically capable of distinguishing between learning trials and automatically tracking stimuli and learning sessions.

In one variation, the system and device may be used to learn more about another person's interests or experiences by sharing content learned or stimuli delivered by the device. This embodiment could be of use to help prepare for an interview, a sales meeting, or a blind date. Similarly, in some variations, the device, system and/or related methods may be used in military, law enforcement, or intelligence gathering applications, including those related to interrogation. In another embodiment, the invention may be used for training of soldiers, members of law enforcement, or intelligence agents.

The devices and systems described herein may also be used as part of a therapeutic method to treat a patient. For example, the devices, systems and methods may be used to improve memory and/or cognitive function by individuals with inherited neurodevelopmental disorders characterized by learning, memory and/or cognitive deficits including Down syndrome, Rett syndrome, fragile X syndrome, neurofibromatosis type 1, tuberous sclerosis, phenylketonuria, maple syrup urine disease, and other inherited neurodevelopmental disorders appreciated by one skilled in the art, as well as disorders such as autism spectrum disorders which are generally diagnosed in the first five years of life and may be due to genetic and/or environmental causes.

An embodiment that applies the device and/or related methods may be used to improve memory and/or cognitive function by individuals with cognitive and/or memory deficits associated with normal aging or neurodegenerative disorders including Alzheimer's disease, Parkinson's disease, frontotemporal dementia, and other age-related or neurodegenerative disorders appreciated by one skilled in the art.

In some variations, the systems, devices and/or related methods may be used by individuals with disorders of sleep such as central sleep apnea, obstructive sleep apnea, insomnia, and other forms of sleep abnormalities appreciated by one skilled in the art, including but not limited to those that lead to reduced memory function or cognitive impairment.

In some variations, the devices, systems and/or methods may be used as a substitute or supplement to drug therapy to enhance or disrupt memory formation or eliminate or otherwise modify existing memories.

In some variations, the systems, devices and/or related methods may be used by individuals with disorders for which memory disruption is desired such as post-traumatic stress disorder (PTSD), obsessive compulsive disorder, depression, or other disorders appreciated by one skilled in the art.

These system and devices may be used by adults and/or children. For example, the systems, devices and/or related methods described herein may be adapted for use by babies, toddlers, or pre-kindergarten-aged children. In this application, one embodiment is a device built into a toy that a child may interact with and/or a piece of clothing intended for the child to wear to bed.

In some variations, the systems, devices and/or related methods may be used prenatally. The sleep state of a fetus may be determined by monitoring movement, heart rate, respiratory rate, brain rhythms, or other physiological correlates of sleep in the womb with detectors placed on or near the mother. The fetus may be presented with auditory training material (e.g. words and definitions or other language content) combined with a neutral sound or haptic stimulus and the neutral stimuli are re-presented when the fetus is sleeping or, in some embodiments, more specifically in deep sleep.

In some variations the systems or devices may use training optimization algorithms to determine what content is presented at what interval to reduce the amount of time required for training.

The sensory stimulus may be optimized. In some variations, the sensory stimulus provided may be optimized based on the information to be learned. As mentioned, the sensory stimulus provided may be non-interruptive, and may be configured to be innocuous so as not to interrupt the concentration of the user during the training session and/or not to awaken or disrupt the user's sleep during sleep consolidation. In some variations the sensory stimulus is provided by third parties (e.g. advertisers) who pay to have a user train with a particular scent, jingle, or other stimulus during training with the device. In another embodiment, a user could purchase a single stimulus or set of stimuli similar to how one buys a ringtone or rights to a copyright-controlled stock image.

An embodiment could populate a user's training set through the Internet on a remote server, or through an intermediate device according to a code (e.g. quick response (QR) code, hashtag, hyperlink, etc.). One specific embodiment would be a QR code at a museum exhibit so that content about the exhibit could be learned at another time. Another specific embodiment would be a QR code on an informational plaque at a park or monument so that content about the geography, ecology, or history of that location could be learned at another time.

An embodiment could select learning material based on location data, social data (e.g. who are you with at a particular time—are they a device user, too?), and/or timing data (e.g. what time did you enter a particular classroom, thus defining whether your training content database should be populated with content about physics (your class) or chemistry (the preceding class)).

In some variations the system or device may select learning material, sensory stimuli, or other aspects based on a user's use of a social network, such as one that includes the functionality of Facebook, Twitter, or Myspace.

In general, the sensory stimulus is unique to a particular learning session or subject matter. Thus, in variations the linking of the sensory stimulus to the subject matter may allow association across training sessions. For example, in some variations the system (e.g., using control or system logic) may select stimuli for the purpose of invoking transitive inference between content to be learned. In a simple example, a user desires to associate the word "orange" with the picture of an orange. While being presented with an olfactory cue, the user is also presented the word "orange." In another learning event, the same olfactory cue is co-presented with the picture of an orange. The user subsequently uses transitive inference to associate the word with the picture, without having a simultaneous presentation of the two items.

In some variations, the system or device may use analytical and/or data mining techniques to determine interests, experiences, and/or previously learned content in order to select a stimulus or set of stimuli that engage transitive inference processes between previous experience and new learning content. These techniques may be provided as logic (e.g., stimulus selection logic) configured as hardware, software, firmware, or the like.

In some variations an automated algorithm (relationship logic) determines which content that has been added to a user's content database is related, similar or coupled (e.g. all the state capitals, the word 'sleeping' in different languages, or a sequence of steps required to perform CPR), then applies the same sensory stimulus (e.g. the sound of snoring or the scent of a rose) for these pieces of training content, even if the learning events are separated in time by minutes, hours, days, weeks, months, or years. This embodiment may be considered as related to the concept of transitive inference. In a related embodiment, a curated service, third party, or socially-derived network may determine whether content to be learned is related, similar or coupled and may use this determination to determine whether the same or similar sensory stimulus should be presented for these items of content to be learned. In another embodiment, the determination of whether training content is related for purposes of choosing identical or similar sensory stimuli to present during training may be made based on whether other users have coupled such content. For instance, if other users had experienced memory improvements due to transitive inference by using a similar stimulus to associate with content to be learned.

In general, the systems, devices and methods described herein monitor the user to automatically determine the sleep phase for the patient, and trigger replay of the sensory stimulus upon or after detection of a particular sleep phase. The sleep phase may be a typical sleep stage (e.g., slow-wave sleep) or a variation of a typical sleep stage. In some variations, the user may have their sleep modified when using the device. For example, a user may take a drug or drugs to increase the frequency, changes the lengths of bouts of, or otherwise enhance the quality or quantity of slow-wave sleep to improve memory consolidation. Such drugs could include gamma-hydroxybutyric acid (GHB, also referred to as sodium oxybate), adenosine A1 receptor agonists, 5-HT2 antagonists or other drugs known to one skilled in the art that increase slow-wave sleep quantity, quality, or intensity. In some variations, the subject may take a drug or drugs that disrupts or reduces slow-wave sleep to interfere with normal memory consolidation. Such drugs could include hypnotics such as flurazepam, benzodiazepine antagonists such as flumazenil, or other drugs known to one skilled in the art that decrease slow-wave sleep quantity, quality, or intensity. In some variations the user may take a drug or drugs to change the frequency, lengths of bouts of, or otherwise modulate the quality or quantity of a particular phase of sleep that may include light sleep, deep sleep, REM sleep, stages S1, S2, S3, or S4 of non-REM sleep, or other identifiable phases of sleep.

Also considered herein is the use of the devices or systems described herein to use one or more techniques (e.g., electrical stimulation, sensory stimulation or other methods) to induce brain rhythms at delta frequencies to modulate the functional properties of slow-wave sleep to improve memory consolidation processes. Similarly, systems, devices and methods may use electrical stimulation, sensory stimulation or other methods to disrupt brain rhythms at delta frequencies to modulate the functional properties of slow-wave sleep to interfere with memory consolidation processes. Electrical stimulation, sensory stimulation or other techniques may be used to induce brain rhythms at other frequencies or with other spatial temporal patterns in order to affect brain rhythms and underlying cognitive processes.

Also described herein are devices, system and methods that use feedback from recording or monitoring of physiological or other parameters that correspond to sleep state or arousal level to define the intensity, modality, and/or specific stimulus delivered during sleep.

For example, described herein are systems for improving memory. These systems may have a training mode and a sleep consolidation mode, and may include: a user interface comprising a control allowing a user to switch the device to the training mode to indicate a training session; a sensory stimulator configured to provide a plurality of distinct sensory stimuli; a sleep monitor configured to monitor a user's sleep state; and a controller comprising control logic receiving input from the user interface and configured to select a distinct sensory stimulus for a specific training session and to control the application of the distinct stimulus during the specific training session, and further wherein the controller receives information on the user's sleep state from the sleep monitor, and controls the sensory stimulator to apply the distinct sensory stimulus from the specific training session when the user is experiencing a specified sleep stage during a sleep consolidation mode following the specific training session.

The sensory stimulator may be configured to provide a plurality of non-distracting sensory stimuli. The sensory stimuli may be, for example, olfactory, auditory, or tactile. In some variations the sensory stimuli is predetermined (e.g., the sensory stimulator or controller may include a set of sensory stimuli for delivery by the sensory stimulator); in some variations the sensory stimulator is configured to provide an ambient sensory stimulus recorded during the training session. For example, the sensory stimulator may comprise an ambient recorder for recording the ambient stimulus wherein the ambient recorder is configured to record one or more of ambient sounds, ambient odors, and ambient sensations.

Any of the systems or methods described herein may be configured so that the specified sleep stage is predetermined from the known sleep stages (e.g., slow wave sleep, light sleep, REM sleep, phases S1, S2, S3, or S4 of non-REM sleep, etc.) or combinations of sleep stages. For example, in some variations the sleep stage is slow wave sleep. In some variations (e.g., for reconsolidation of amydalar memories that may be important for PTSD) the sleep stage is rapid eye movement sleep.

In any of the variations described herein the systems and devices may include a memory (e.g., a computer or digitally readable/writable memory). This memory may be connected directly or remotely to the controller. The memory may be configured to store information that indicates one or more of which sensory stimuli have been applied for specific training sessions, the sleep state of user, and completion of application of a sensory stimulus during a sleep consolidation mode following a specific training session. In some variation the memory is important for storing and providing user configuration. For example, the device or system may read a user configuration file or memory to determine what sensory stimuli have been used, or are available for use, and/or for determining what training has occurred, or has been paired with a sensory stimuli. The configuration file may also store user information (e.g., biometric information) and/or access information. The controller may be configured to read information from the memory.

In general, the user interface is adapted so that the user may readily and easily control operation of the system or device. For example, the user interface may include at least one of: a switch, a toggle, a button, a slider, a knob, or a touchscreen, and may indicate (via instructions, menus, or the like) what options the user may select. The user interface may provide visual, audible, or tactile feedback on the status or operation of the device and/or system.

Any appropriate sleep monitor may be used. The system or device may include sleep monitoring logic to determine (based typically on information provided by a sleep monitor) what sleep state the user is in. This determination may be probabilistic (e.g., the logic may indicate a user is in a particular sleep state, or is not even sleeping, when user indicators (e.g., movement indicators, thermal indicators, electrical indicators, etc.) indicate that the likelihood of a particular sleep state is above some threshold). In some variations the sleep monitor comprises a non-contact sleep monitor. For example, the sleep monitor may be positioned near the sleeping user and may indicate (based on motion) an approximation of which sleep state the user is in.

In any of the variations described herein the system or device may be configured to reside all or partially in a housing. For example, the housing may at least partially enclose the user interface, sensory stimulator, and controller, and/or other components. In some variations the system or device is portable. For example, a portable system may include a housing and may be battery-powered or wall (plug-in) powered. The devices or systems may be lightweight, particular the portable systems. For example the device or system may weigh less than 20 pounds, less than 15 pounds, less than 10 pounds, or less than five pounds. In some ultra lightweight configurations the system weighs less than a pound. For example, a system or device may be configured to operate on a handheld device (e.g., iPhone™, iPad™, Android, or other mobile device capable or running application software). For example, the control logic comprises an application configured to be executed on a mobile device.

The system or device may include a handle. In general, these systems and device are intended for a user to operate without requiring additional assistance, at home (e.g., for personal use).

Any of the devices or systems described herein may include a communications module coupled to the controller configured to allow communication with a remote site.

Thus, for example, also described herein are portable user-controllable devices for improving memory, the device comprising: a user interface comprising a control allowing a user to place the device into a training mode indicating a training session; a sensory stimulator configured to present a plurality of distinct sensory stimuli; sleep monitoring logic configured to determine when the user is in a specified sleep state; and a controller comprising control logic configured to determine a specific sensory stimulus received by the user concurrent with a particular training session; wherein the controller is further configured to reapply the specific sensory stimulus when the user is in a specified sleep state following the training session. As mentioned, the portable system or device may include a housing at least partially enclosing the user interface, sensory stimulator, and controller. The portable system or device may also include a sleep monitor configured to monitor the user's sleep state.

Also described herein are systems for improving memory having a training mode and a sleep consolidation mode, the system comprising: a user interface comprising a control allowing a user to switch the device to the training mode to indicate a training session; a sensory stimulator configured to play back an ambient stimulus recorded during a training session; a sleep monitor configured to monitor the user's sleep state; and a controller comprising control logic receiving input from the user interface and configured to cause the system to record the ambient stimulus during the training session, further wherein the controller receives information on the patient's sleep state from the sleep monitor, and controls the sensory stimulator to apply the recorded ambient stimulus when the user is experiencing a specified sleep stage following the specific training session.

As mentioned above, any of the systems or devices described herein may be configured to use ambient sensory stimuli, including ambient noise. In some variations the system or device may therefore include an ambient recorder for recording the ambient stimulus. The ambient recorder may be part of the sensory stimulator, or it may be a separate element. For example, an ambient recorder may be configured to record one or more of ambient sounds, ambient odors, and ambient sensations. In some variations the sensory stimulator is configured to access one or more sources of ambient stimuli that are active during the training session. The one or more sources of ambient stimuli may include one or more of: audio players, computers, televisions, mobile devices, scent releasing devices, and massage/vibratory devices, or any other device configured to deliver a sensory stimulus to the user.

Also described herein are methods of improving memory with a user-controlled device. For example, the method may include the steps of: selecting, in a user-controlled device, a specific sensory stimulus that is received by the user during a first learning period; detecting, with the user-controlled device, a specified sleep stage in the user following the first learning period; and delivering, from the user-controlled device, the specific sensory stimulus to the user during the specified sleep stage following the first learning period. In some variations, the method further includes delivering, from the user-controlled device, the specific sensory stimulus to the user during the first learning period. In some variations the method includes using ambient sensory stimuli. For example, the method may include selecting the specific sensory stimulus by recording an ambient sensory stimulus during the first learning period.

As mentioned above, delivering the specific sensory stimulus may include delivering a non-distracting sensory stimulus.

In some variations, the method includes the steps of: selecting, in the user-controlled device, a second sensory stimulus that is different from the first sensory stimulus and that is received by the user during a second learning period; and delivering the second sensory stimulus to the user during a specified sleep stage following the second learning period.

The method may also include the step of switching the user-controlled device so that the device is in a training mode during the first learning period and in a sleep consolidation mode during delivery of the sensory stimulus to the sleeping user.

Selecting the sensory stimulus may include choosing a sensory stimulus from among a plurality of non-distracting sensory stimuli that have not previously been delivered by the user-controlled device during a learning period. In some variations, selecting the sensory stimulus comprises selecting one or more of: an olfactory stimulus; an auditory stimulus; and a tactile stimulus.

Detecting a specified sleep stage in the user following a learning period (e.g., the first or a second learning period) may include monitoring the users sleep state without contacting the users head or portion of the user's body.

In some variations, the method may also include storing in a memory information that indicates one or more of: which sensory stimulus has been selected, a sleep state of user, and completed delivery of a sensory stimulus during the specified sleep stage.

Also described herein are methods of disrupting memory formation in a user, the method comprising: delivering, from a user-controlled device, a specific sensory stimulus to the user during a training period comprising recollection or re-experience of information to be forgotten; detecting, from the user-controlled device, a specified sleep stage in the user; delivering, from the user-controlled device, the specific sensory stimulus during the specified sleep stage; and disrupting the specified sleep stage.

As mentioned above, disruption of memory may be particularly valuable in treating a disorder of memory such as post-traumatic stress disorder (PTSD) and the like. The step of disrupting the specified sleep stage comprises waking the user and/or modulating brain rhythms active during the specified sleep stage, and/or shifting the user to a different sleep stage and/or disrupting the sleep stage through brain stimulation. As mentioned above, the specified sleep stage may be any appropriate sleep stage, including slow wave sleep or rapid eye movement sleep.

Also described herein are methods of treating a user for a disorder of memory with a user-controlled device, the method comprising: delivering, from the user-controlled device, a specific sensory stimulus to a user having a disorder of memory during a first learning period; detecting, with the user-controlled device, a specified sleep stage in the user following the first learning period; and delivering, from the user-controlled device, the sensory stimulus to the user during the specified sleep stage following the first learning period.

Any appropriate disorder may be treated. For example, the disorder may be a disorder of memory that is a neurodevelopmental disorder, such as one or more of: Down syndrome, Rett syndrome, fragile X syndrome, neurofibromatosis type 1, tuberous sclerosis, phenylketonuria, maple syrup urine disease, autism spectrum disorders. In some variations, the disorder of memory is a cognitive and/or memory disorder. In some variations, the disorder is a neurodegenerative disorder, such as one or more of: Alzheimer's disease, Parkinson's disease, Huntington's disease, frontotemporal dementia. In some variations, the disorder is one or more of a sleep disorder, central sleep apnea, obstructive sleep apnea, and insomnia.

Also described herein are systems and methods useful for achieving effective modulation of memory consolidation during sleep. More particularly, described herein are devices, systems, and methods for achieving effective modulation of cognition or memory over one or more days and/or nights, including devices, systems, and methods for configuring, populating, and querying a learning database with training content and contextual sensory stimuli co-presented with the training content, as well as devices, systems, and methods for selecting, prioritizing, and scheduling contextual sensory stimuli to be presented during study and sleep. Systems are described that are configured to determine how to use training content from the learning database to determine a training schedule for repetition of sensory stimuli associated with particular training content over one or multiple nights of sleep.

As described in greater detail below, any of the systems, devices and methods described herein may be adapted specifically for use with electronic media. Use with electronic media has particular advantages. In particular, the systems, methods and devices may be configured so that the electronic media is analyzed and features (e.g., content-based features and/or contextual features, including structural features) of the electronic media may be used to determine/select the sensory stimuli and/or the manner in which the sensor stimuli is delivered or replayed.

For example, described herein are systems for improving learning, memory, or learning and memory from an electronic media. Such systems may include a training mode and a sleep consolidation mode, and further comprise: a sleep monitor configured to monitor a user's sleep state; a sensory stimulator configured to provide a plurality of distinct sensory stimuli based on the electronic media; a controller comprising control logic configured to select a sensory stimulus for a specific training session based on the content of the electronic media, and to control the application of the sensory stimulus, wherein the controller receives information on the user's sleep state from the sleep monitor, and controls the sensory stimulator to apply the contextual sensory stimulus from the specific training session according to a training schedule when the user is experiencing a specified sleep stage during a sleep consolidation mode; and a learning database configured to be populated with training content and sensory stimuli co-presented with the training content, wherein the controller is configured to determine which sensory stimuli to use based on the electronic media.

As mentioned above, the sensory stimulator may be configured to provide an ambient sensory stimulus recorded during the training session. The controller may also be configured to determine which sensory stimuli to use based on the content of the electronic media. In general, the content of the electronic media may refer to the subject matter content (e.g., what is being delivered), the content delivery (e.g., language, modality, appearance, etc. of the delivered content), the relation of the content to previously delivered content, etc.

In some variations, the controller is configured to determine how to apply the sensory stimuli based on the content of the electronic media. For example, the number of sensory stimuli to deliver, the intensity of the delivered sensory stimuli (e.g., volume of the sensory stimuli for auditory stimuli, etc.), or the like.

In some variations the controller is configured to determine which sensory stimuli to use based on the structure of the electronic media. In general, the structure of the electronic media may refer to the delivery characteristics of the electronic media, such as the length (e.g., duration) of the delivered electronic media, the type of electronic media, etc.).

The system may also include a memory configured to store information that indicates one or more of: which sensory stimuli have been applied for specific training sessions, the sleep state of user, and completion of application of a sensory stimulus during a sleep consolidation mode following a specific training session.

Any appropriate electronic media may be used. For example, the electronic media may comprise an electronic book (e.g., e-book), a digital recording, etc. Any of the device/system variations described herein may include an analysis module configured to pre-analyze the electronic media to determine sensory stimuli to apply. An analysis module may include software, hardware, and/or firmware that is configured to review and analyze the electronic media before and/or during delivery. The analysis module may determine characteristics, including content-based characteristics, such as subject matter characteristics or the like, and context-based characteristics (e.g., structural characteristics, such as the length of the material to be delivered, etc.). The analysis module may include analysis logic for recognizing content or context characteristics. In some variations the analysis module includes analysis logic configured as a neural network for recognizing content and/or context. In some variations the analysis module is configured to read one or more "tags" associated with the electronic media that determine the content and/or context characteristics.

Also described herein are portable user-controllable device for improving learning and memory from an electronic media, the device comprising: a user interface comprising a control allowing a user to place the device into a training mode before the user experiences the electronic media; a sensory stimulator configured to present a plurality of distinct sensory stimuli concurrently with a user's experience of the electronic media; sleep monitoring logic configured to determine when the user is in a specified sleep state; and a controller comprising control logic configured to determine a sensory stimulus based on the electronic media for a particular training session; wherein the controller is further configured to reapply the specific sensory stimulus when the user is in the specified sleep state following the training session; wherein the controller is configured to determine which sensory stimuli to use based on the content, structure or content and structure of the electronic media.

DETAILED DESCRIPTION

Figure 1A:
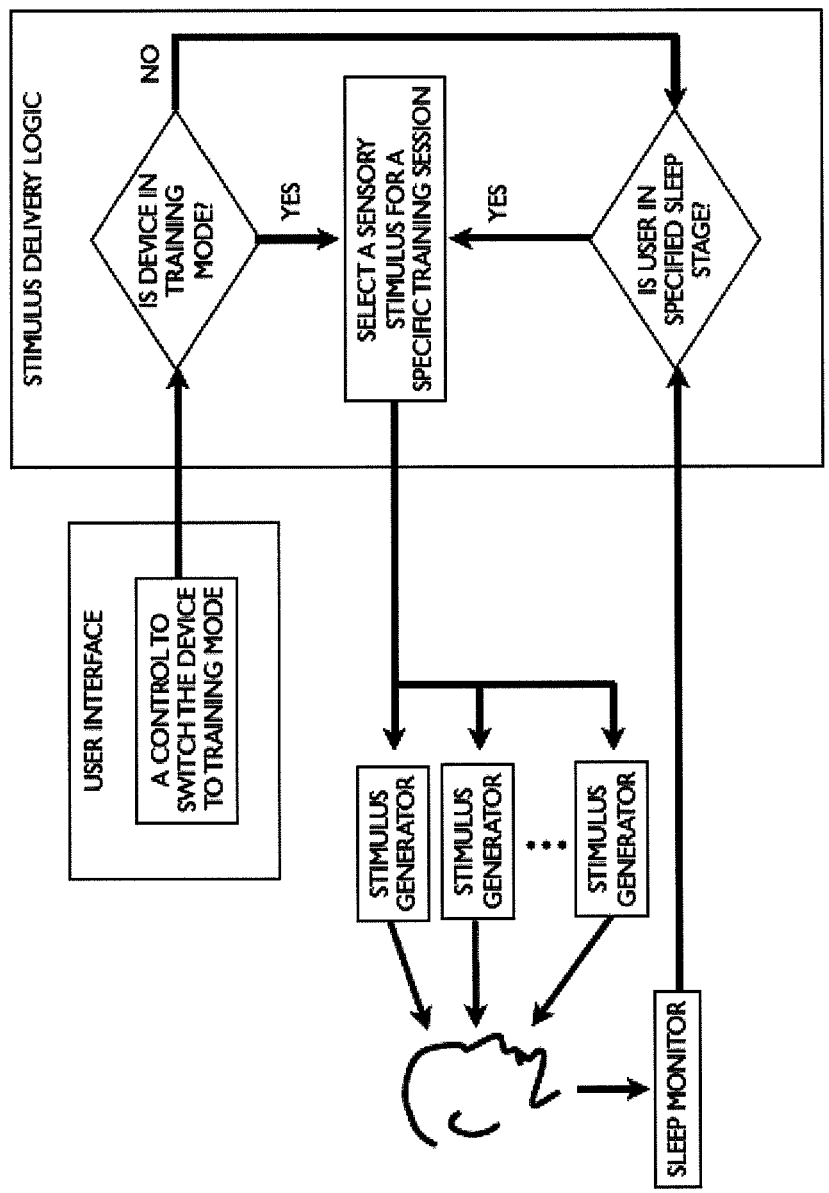
FIG. 1A shows a schematic view of one variation of a system/device for improving memory during sleep as described herein.

Reference throughout this specification to "one embodiment," "one variation," "an embodiment," "a variation" or similar language means that a particular feature, structure, or characteristic described in connection with the embodiment or variation is included in at least one embodiment or variation of the present invention. Thus, appearances of the phrases "in one embodiment," "in on variation," "in an embodiment," and similar language throughout this specification may, but do not necessarily, all refer to the same embodiment or variation.

The devices, systems and methods described herein may be embodied in other specific forms without departing from their spirit or essential characteristics. The described embodiments and variations are to be considered in all respects only as illustrative and not restrictive.

Memories formed during wakeful activity are consolidated into long-term memories during sleep. Certain phases of sleep are especially important for memory consolidation, and ambient stimuli that occur during studying can facilitate consolidation if replayed during those important sleep phases. We have built a system, described herein, that enhances memory formation. The system associates the various pieces of information the user is attempting to learn with the sensory environment experienced by the user while studying. The system can either record natural stimuli in the study environment, such as the music playing or other ambient noises, or it can deliver stimuli, such as pleasant and unique odors or sounds. Later, when the user is sleeping, the system monitors sleep phase by analyzing various sensors such as those for monitoring brain waves, muscle activity, movement, heart rate, and breathing. In one embodiment, when the system determines that the user is in a phase of sleep important for memory consolidation, the system replays the stimuli associated with the information currently being learned. Reactivating the sensory stimuli experienced during an awake study may aid consolidation of the target information during sleep. In the morning, the system may track learning progress by testing the user's ability to remember the information studied during the previous day and consolidated during sleep.

The following terms may be used herein. As used herein, the phrase "Training Mode" optionally may be referred to as a Study Mode or the Training Phase, and may refer to a state of the device or system during which the user utilizes the memory enhancing device during a session to learn training content. The device activates its stimulus generators at opportune times as the user experiences elements of learning content. Training Mode or Study Mode may occur during a Training Period, Study Period, Training Session, or Study Session.

As used herein the term "Sleep Mode," optionally referred to Sleep Consolidation Mode, refers to a state of the invention, during which the user utilizes the memory enhancing device during sleep. The device may assess the user's sleep state. In some variations, during slow wave sleep, the device activates its stimulus generators to enhance memory consolidation.

For the purposes of this description, physiology may refer to any biological process in a human.

As used herein, "memory" or organic memory (as opposed to computer or device memory) typically refers to a mental process by which information is encoded, stored, and retrieved by the brain. There are different types of memory, including motor memory, episodic memory, and emotional memory.

As used herein, a mobile device may include a hand-held portable computing device (e.g. cellular phone, portable music player, or personal digital assistant).

As used herein, "Contextual Sensory Stimulus" may refer to a sensory stimulus that is co-present with elements of training content. For example, a green light presented while the lyrics to a song are being learned, or the aroma in a room while vocabulary is studied.

As used herein, "Ambient Stimuli" may refer to sensory impressions experienced by the user while studying in a natural environment, beyond what the system itself produces, such as music, coffee aroma, or bus vibrations. "Non-Distracting Sensory Stimuli" may refer to a sensory stimulus which does not disrupt the process of studying, or the sleep of the user.

As used herein "Learning Database" may refer to a relational set linking each element of information from training content to the appropriate contextual sensory stimulus.

"Training Content" may refer to a set of facts or information to be learned.

As used herein, "Trigger State" may refer to a stage of sleep or aspect of sleep (e.g. slow wave sleep) that cues the device or systems for modifying memory described herein to begin delivering sensory stimuli to the user.

As used herein, "Modulating memory consolidation" may refer to enhancing or disrupting memory consolidation, or enhancing and disrupting memory consolidation (e.g., enhancing some, disrupting others).

In general, the systems described herein may include one or more of: a user interface that is configured to allow a user (without requiring a third party) to control and operate the system; a sensory stimulator configured to provide a plurality of distinct sensory stimuli; a sleep monitor to monitor the user's sleep state; and a controller to coordinate the operation of the system in providing the appropriate sensory stimulus during a training period and again later during one or more sleep consolidation periods. The system may be specifically configured to be operated by the user over a plurality of different training sessions, providing different (i.e., unique) sensory stimuli to coordinate with the different training sessions and/or different materials to be learned.

The systems and devices described herein may combine multiple modules into a cohesive system. These modules or components may include control logic (e.g., software, firmware, hardware, or the like) which matches learning content with associated sensory stimuli delivered, and hardware (e.g., sensory stimulators) such as scent dispensers or audio speakers and/or recorders. During sleep, monitoring hardware such as electroencephalography (EEG) for recording brain rhythms may be analyzed by logic (e.g., algorithms or logic for detecting deep sleep, such as slow-wave, or delta, 0.5-4 Hz, rhythms in the EEG signal) or other sleep stages and then triggering presentation of sensory stimuli (e.g., sounds or smells). In some variations, performance may be monitored by the system to test memory performance the following day. The platform may use wireless and internet-based networking technologies to access a database that may include learning content, sensory stimuli, and/or sleep monitoring parameters in order to optimize system performance for an individual user or patient population.

For example, FIG. 1A shows one variation of a schematic illustrating some of the functional components of a system or device. In this example, the system includes a user interface, which has a control to switch the device to a training mode. The system or device may include various modes of operation, including a training mode, during which a sensory stimulus may be applied, and a sleep consolidation mode, during which the system monitors the user/patient to determine if the user is in a desired sleep state (e.g., a sleep state conducive to memory consolidation). Thus, the system also includes a sleep monitor, examples of which are provided below, to determine or estimate the patient's sleep state. The system also typically includes a stimulus generator to generate a plurality of sensory stimuli, and a controller to coordinate the activity of the system, as discussed herein. In some variations these elements are separate modules or components, which may be functionally connected (via the controller, for example). In some variations these elements are completely or partially housed within a housing, and may form a unitary device.

Figure 1B:
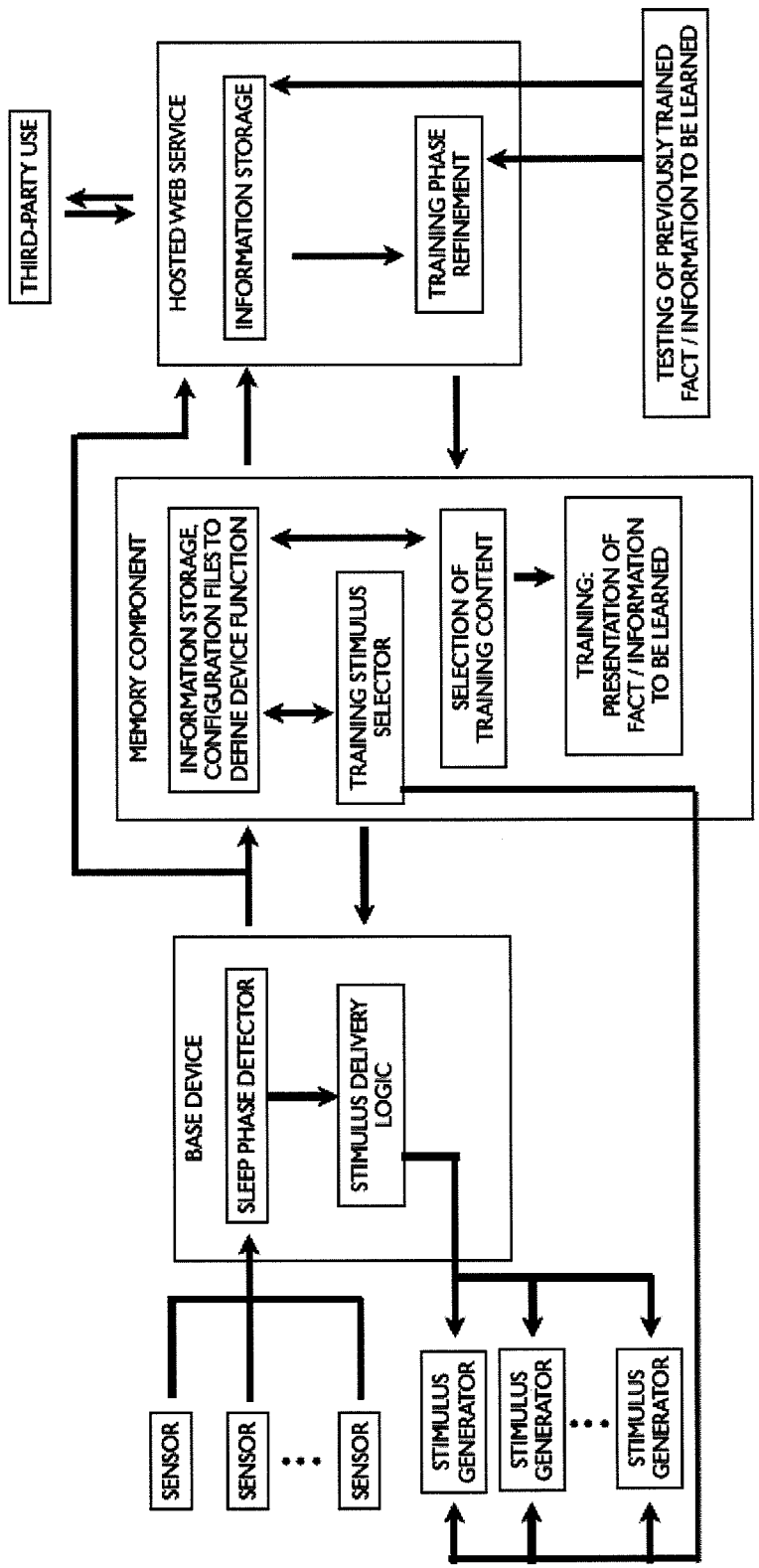
FIG. 1B illustrates functional elements of another variation of a system as described herein.
Figure 2:
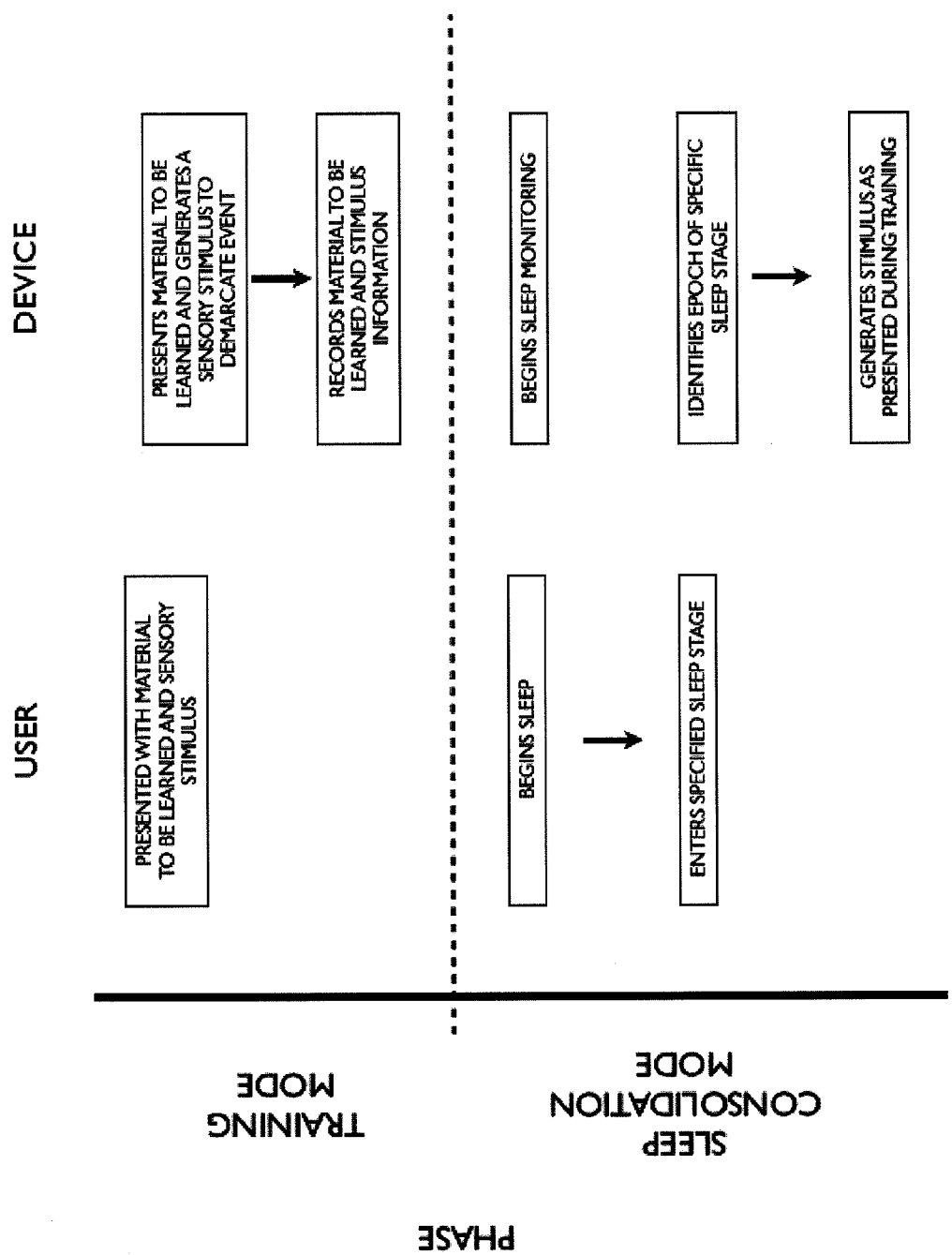
FIG. 2 shows a timeline illustrating how the user may interact with a system in an exemplary usage in accordance with one embodiment.
Figure 9:
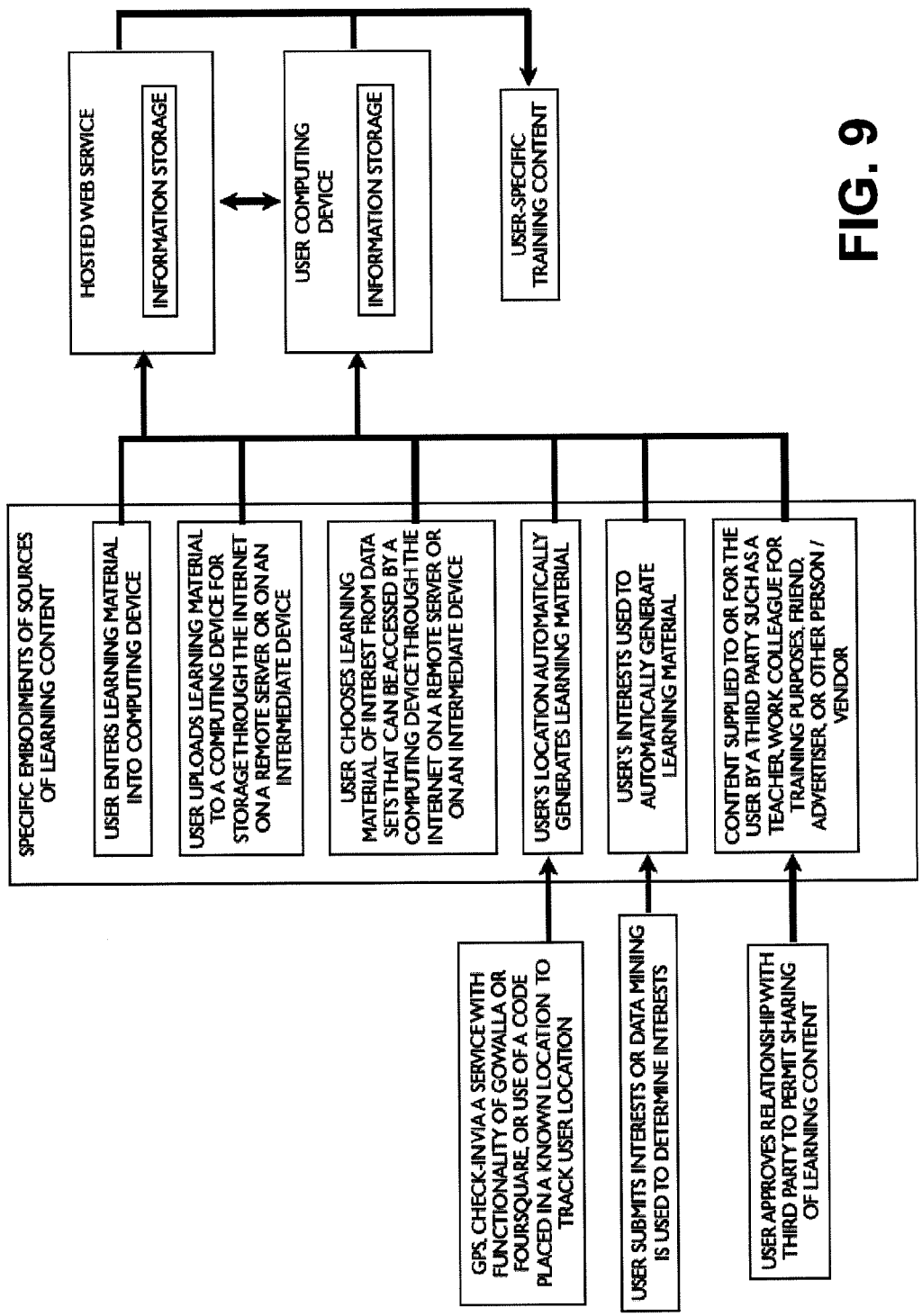
FIG. 9 shows methods for determining user-specific training content in accordance with one variation.

FIG. 1B shows another variation of a system/device for modulating memory in a sleeping user. In this embodiment, several functional regions/steps are shown. The first step is to provide a piece of control logic (e.g., software) that functions as a desktop, web, or handheld device application (FIG. 1B). The control logic may permit a user to search a database of existing learning content supplied by a third party or the user may upload or otherwise enter their own information to be learned into the database. In another embodiment, the software may select training content for the user based on the user's interests, friends, locations where they have been, membership in a group (such as being a student in a particular class), or other sources (see FIG. 9, below).

In FIG. 1B, once the user and/or software has selected training content for the user to learn, the system may present the user with the training material in a manner that can be conducive to learning such as a flashcard-like framework in which one item of a training pair (e.g. a technical term) may be shown to the user, followed by the other item of the training pair (e.g. the definition of the technical term).

Figure 3:
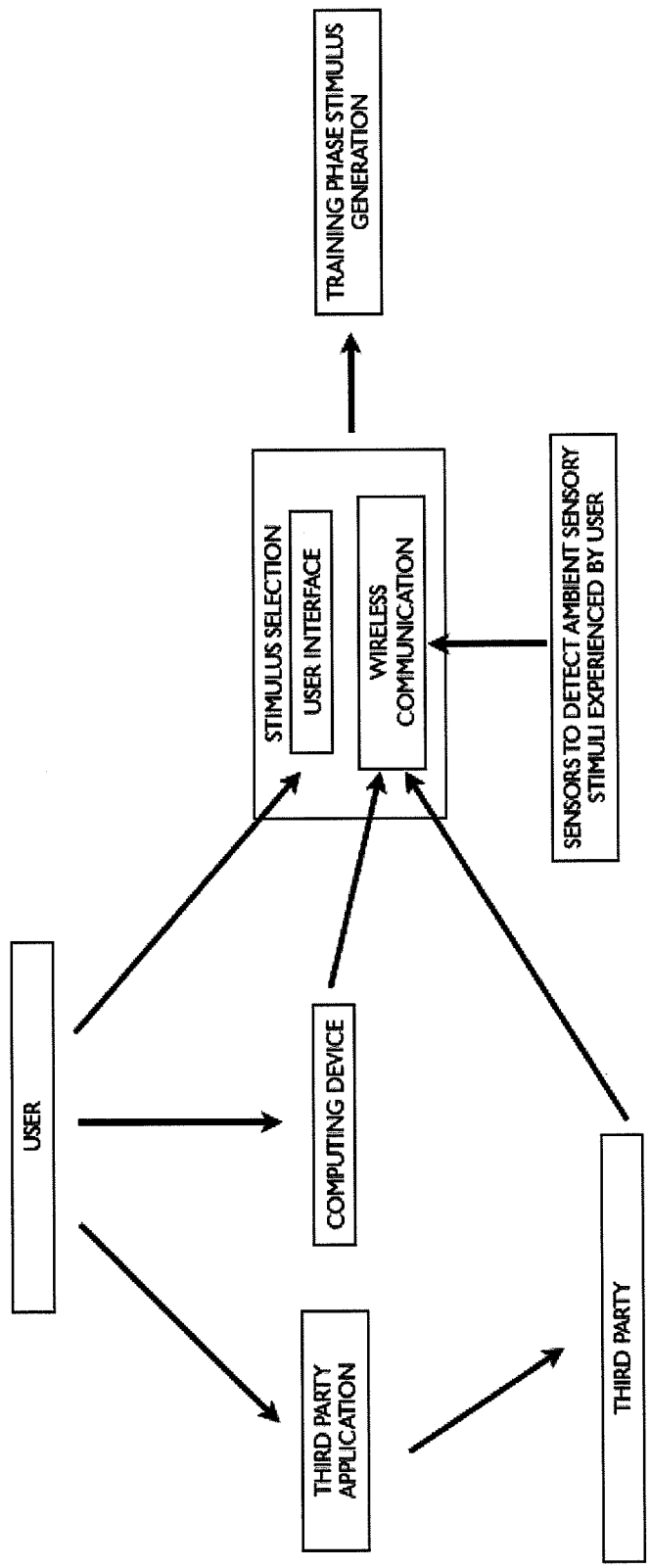
FIG. 3 illustrates how conditioning stimuli may be selected for training where the user can directly communicate to the device/system, or via a networked computing device, or may interact with a third party device to choose training content.
Figure 4:
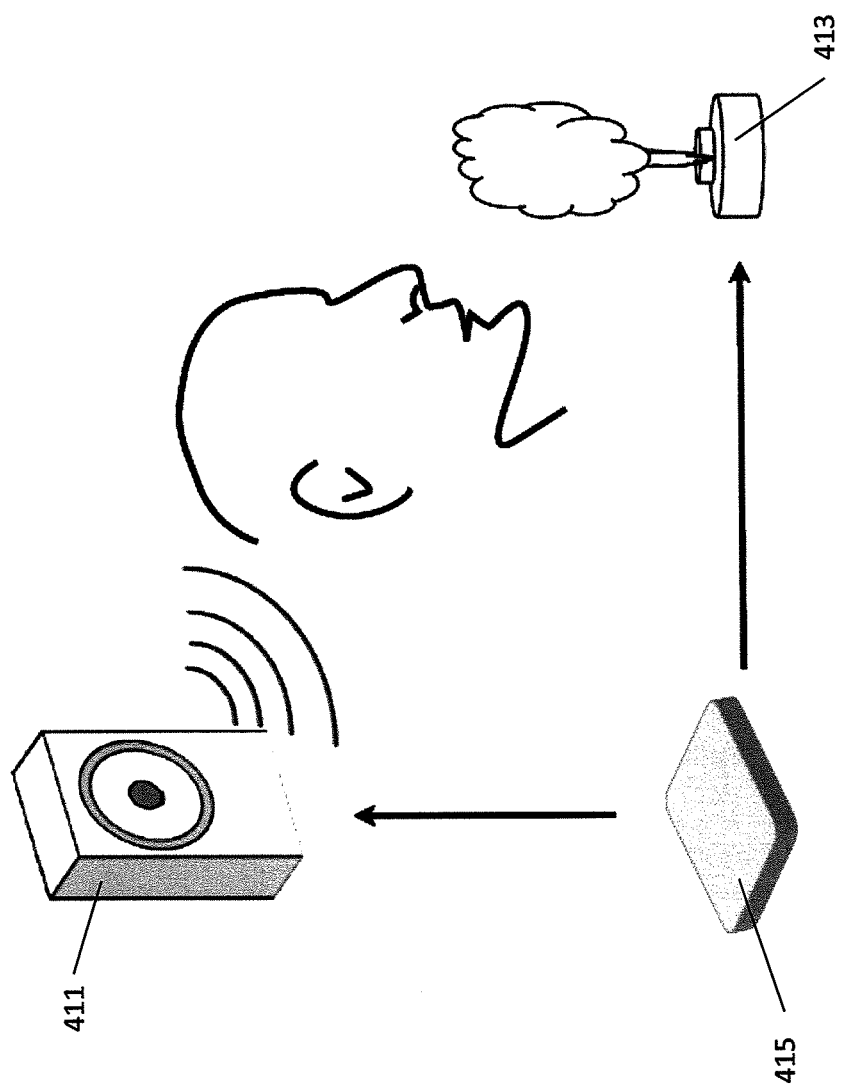
FIG. 4 shows how individualized stimuli may be delivered to the user through modular devices in accordance with one variation.

At the same time or near in time to the user's learning session, a sensory cue can be presented, for instance a sound delivered by a speaker (one variation of a sensory stimulator), a scent delivered by an odorizer (another variation of a sensory stimulator), a haptic stimulus delivered to the user's body, or other sensory stimulus (FIGS. 3 and 4).

In some variations, the device may record the training content learned and sensory stimuli delivered to a database that can be stored on the device used for training or remotely via the Internet or an intermediate device.

Figure 5:
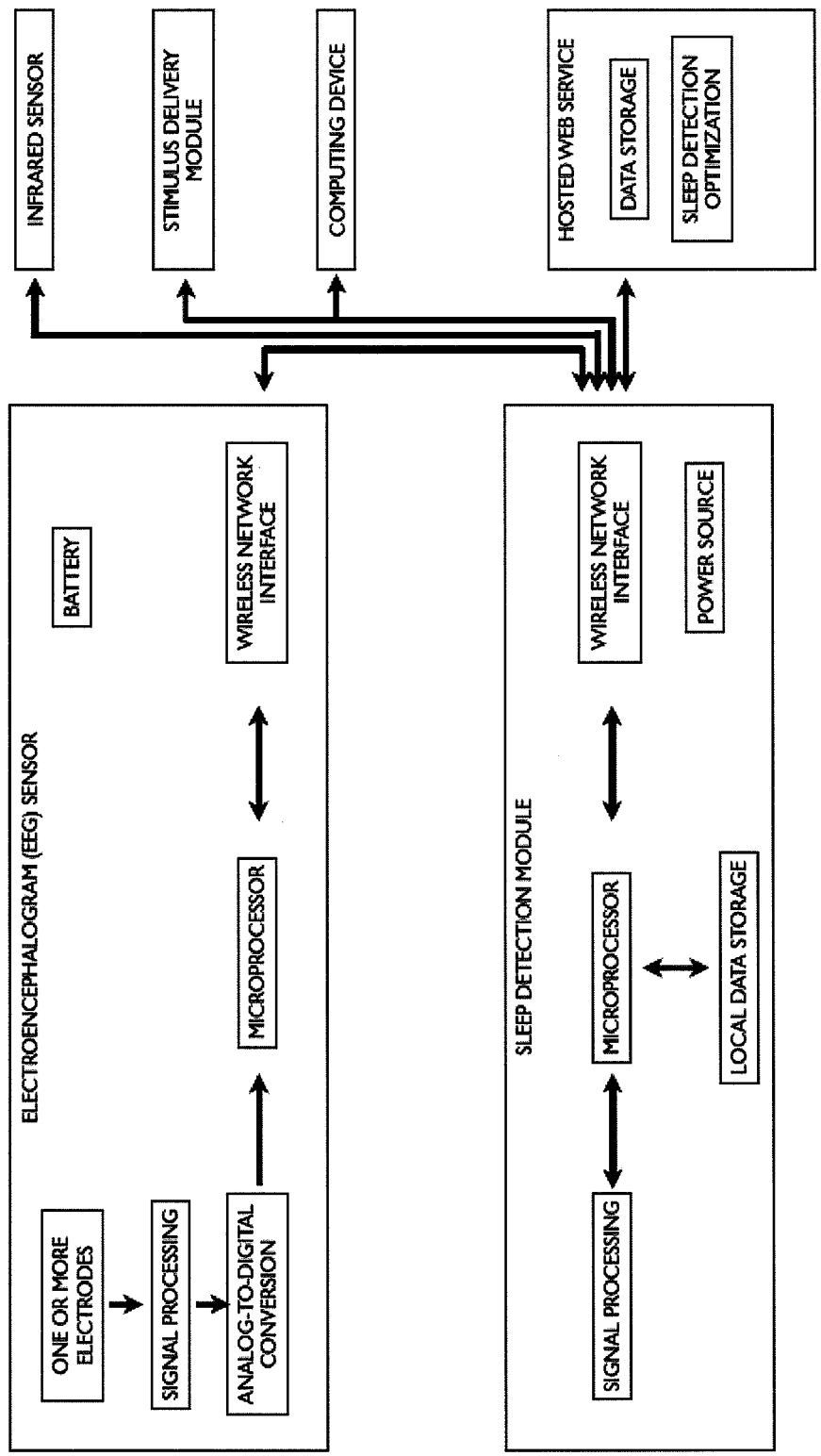
FIG. 5 shows device components for monitoring physiological features of sleep staging with an electroencephalogram detector (EEG) in accordance with one variation.
Figure 6:
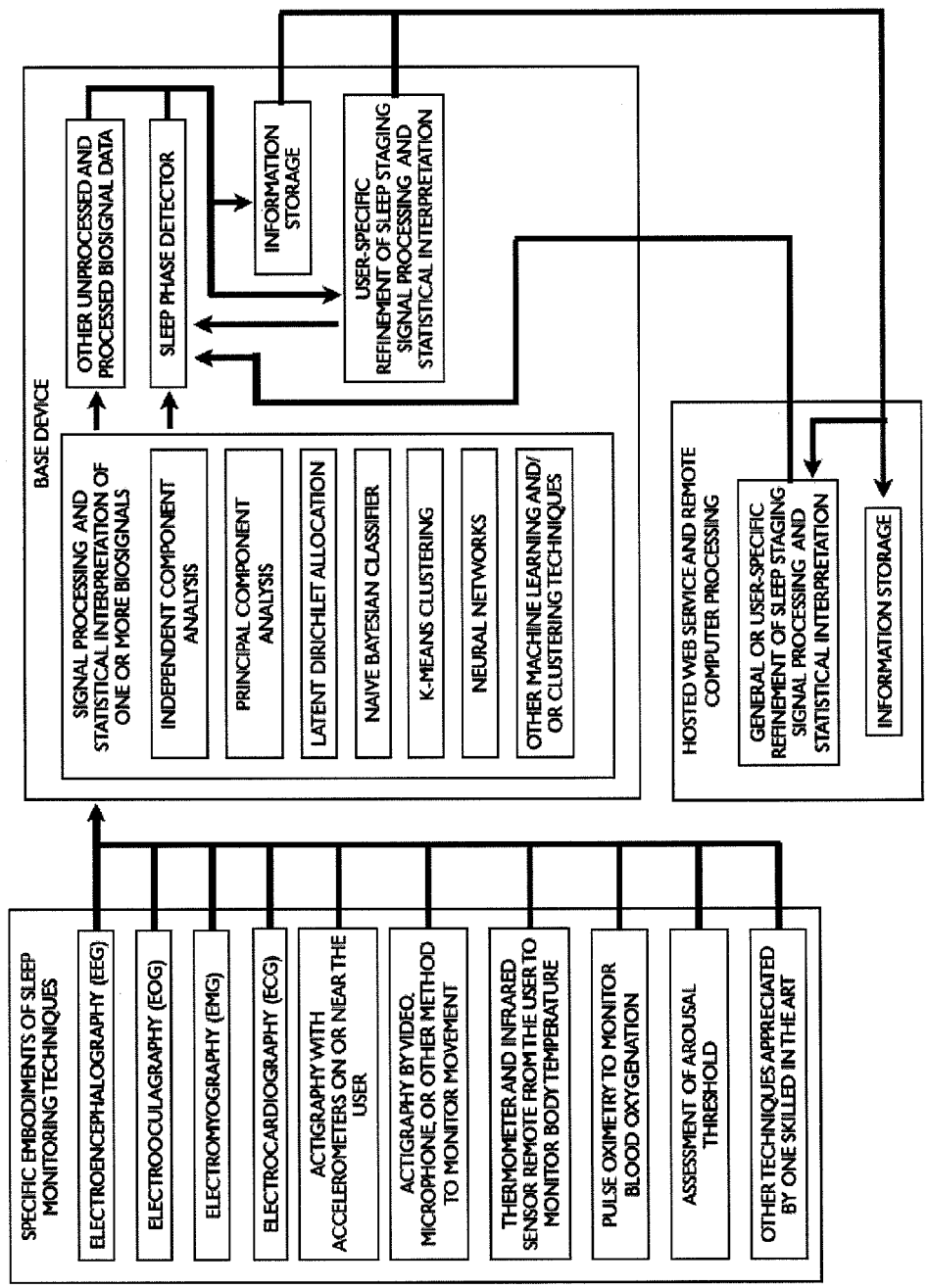
FIG. 6 shows techniques for sleep phase detection and storage of sleep staging data in accordance with one variation.

When the user goes to sleep on the subsequent night or a later night or during a nap, the user's sleep state can be monitored by one or more techniques appreciated by one skilled in the art (FIGS. 5 and 6).

Figure 7:
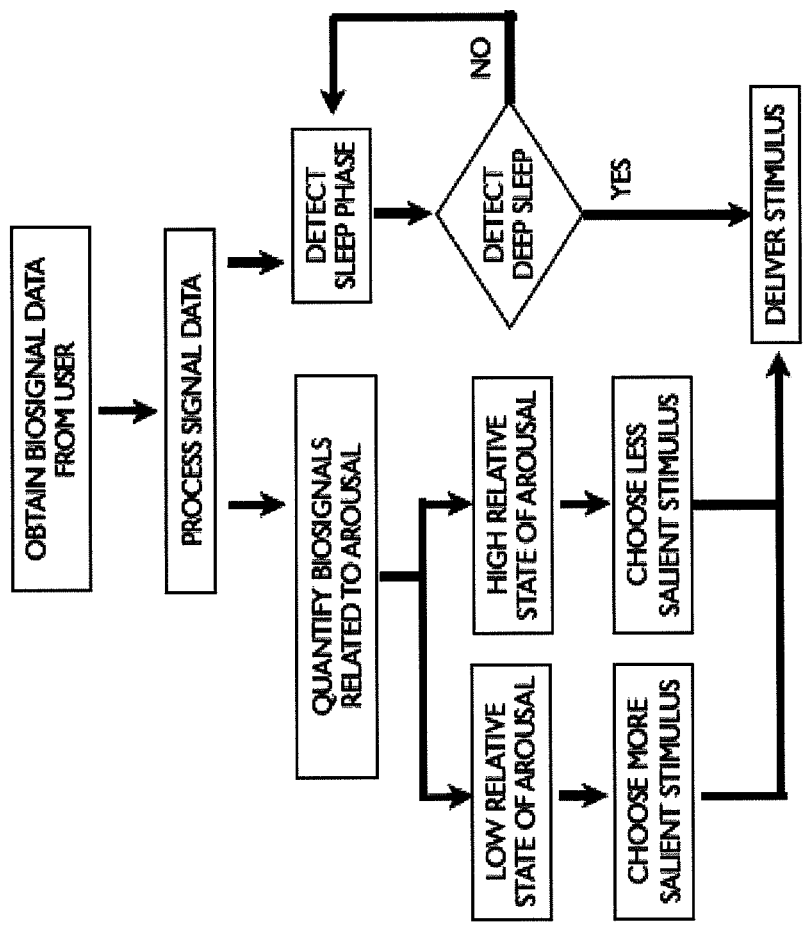
FIG. 7 shows how real-time monitoring of biosignals to assess arousal state and sleep state can be used to choose or modulate the sensory stimuli delivered during SWS in accordance with one variation.
Figure 8:
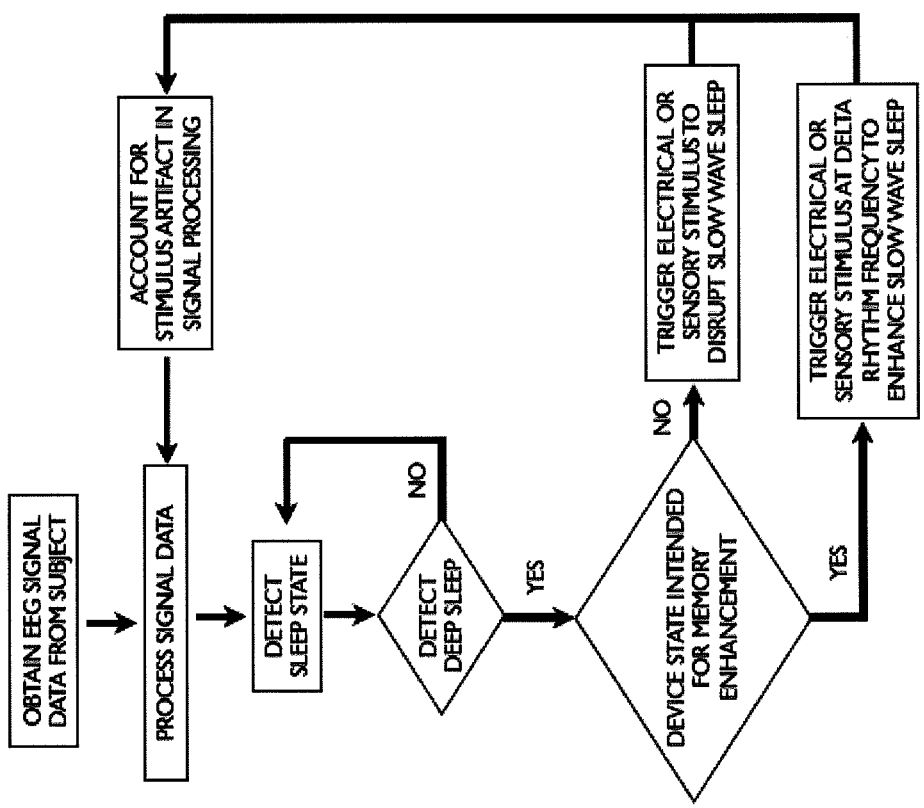
FIG. 8 shows how sensory or electrical stimulation at device-defined frequencies may be used to enhance or disrupt slow-wave 'delta' oscillations during slow-wave sleep in accordance with one variation.

The system may include sleep monitoring that can identify particular stages of sleep and communicate this information to a device that determines whether to deliver sensory stimuli and, if so, which sensory stimuli to deliver at which sleep stage to a particular user. In one embodiment, sleep monitoring may be accomplished by electroencephalography (EEG) and the sleep state during which sensory stimuli are delivered may be deep sleep identified on the basis of one or more brain rhythms such as delta rhythms (generally about 0.5-4 Hz) and/or the absence of muscle activity related to eye or other movements generally indicative of other stages of sleep. In one embodiment, the quantity or quality (e.g. intensity) of a particular stage of sleep that may be deep sleep can be increased or decreased by delivering sensory stimuli or electrical stimulation (FIG. 8). In one embodiment, the choice of sensory stimulus and/or its intensity and/or its rate of repetition can be adjusted based on the level of arousal of the user during sleep (FIG. 7).

In some variations, efficacy of the system may be determined by re-testing the user the following morning or at a later time to determine whether training material was learned.

In some variations the system may save information to a memory, including a local memory or database on a base device or remotely via the Internet or an intermediate device. Stored information may be related to a) training content; b) the success or failure to remember a particular item of information; c) sleep monitoring data related to physiology and/or sleep phase; d) the sensory stimuli delivered and the intensity of the sensory cues (e.g. how loud was a sound); and/or e) other information.

Figure 10:
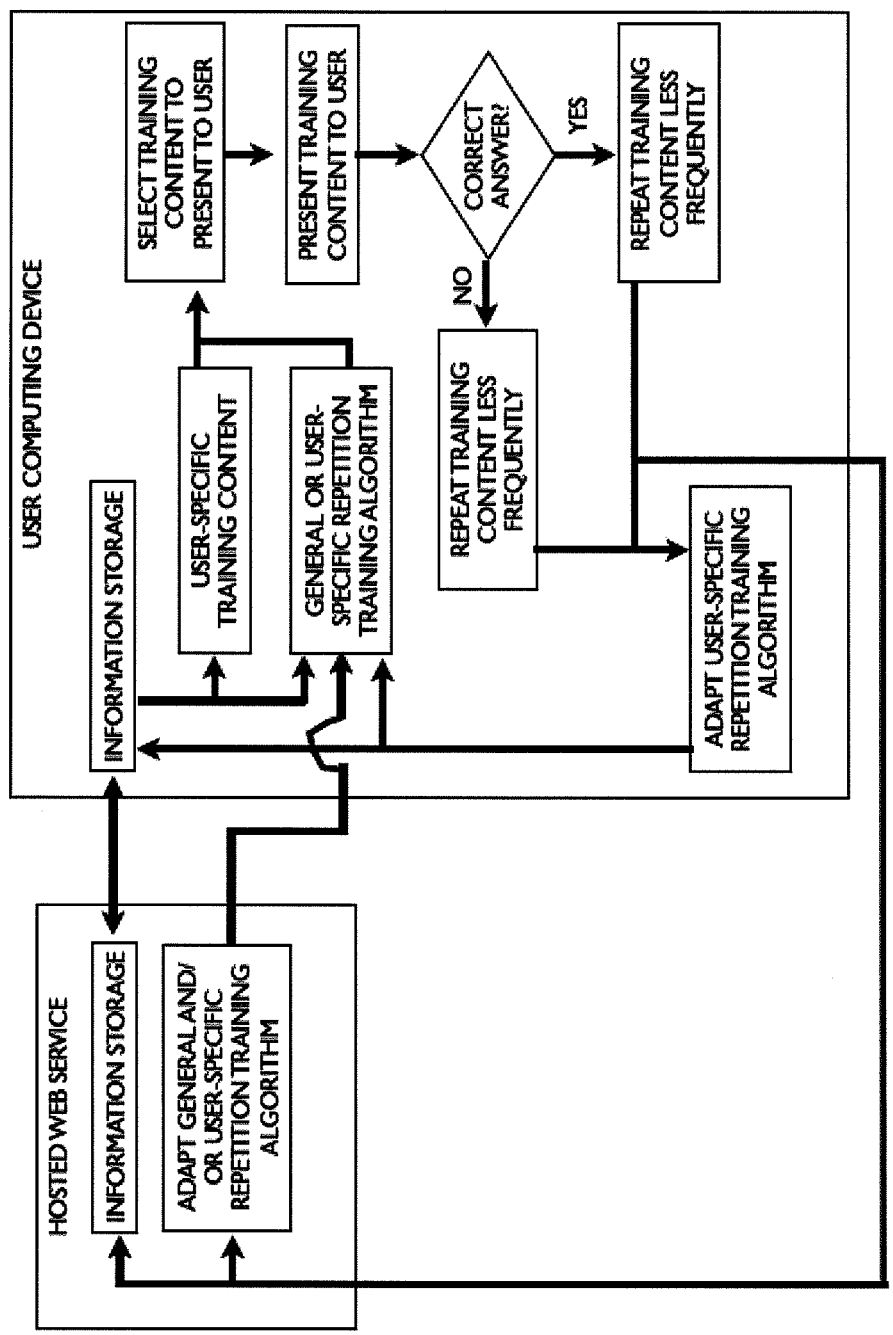
FIG. 10 shows how the invention determines individualized training parameters to improve the efficiency of memory training and memory consolidation during sleep in accordance with one variation.

In some variations the system or device uses data mining and/or other statistical techniques to analyze stored data in order to improve or otherwise modify the quality of memory enhancement and/or sleep detection for the user or for other users (FIG. 10). For instance, in one embodiment, the rate of repetition of particular training content may be optimized.

In one embodiment, the system or device may include a module (e.g., stimulus generator) to deliver stimuli during the presentation of training content, an element to deduce the user's phase of sleep (e.g., sleep monitor), a processor (e.g., controller and/or control logic) to coordinate what stimuli the user should be exposed to, and to cause the stimulus-generating module to create the determined stimuli. The system or device may be controlled by the user, and may allow evaluation, optimal training material, and storage and creation of meta data related to training, stimuli used, sleep, and memory performance in the context of the training system, and methods to keep an accounting of which stimuli are associated with what data. The system or device may also use specific stimuli to modulate the user's phase of sleep.

In some variations, the system or device interacts with the user under two primary conditions: an initial learning event whereby an awake user attempts to learn a fact or concept, (training phase), and a later memory consolidation phase, during which the invention monitors the user's sleep state, and presents stimuli at specific epochs for the purpose of improving the user's memory of the initial learning event. In the awake phase, a user is presented with learning material. During this initial learning/training phase, the device may present a conditioning stimulus, or may record an ambient stimulus for future playback. Later, in the consolidation phase, as the user enters sleep, the device may monitor physiological parameters to identify sleep state. At various times during sleep, the user may enter a slow wave sleep (SWS) epoch, which may be identified by the device and prompts the device to present the conditioning stimulus. In other embodiments, sensory stimuli may be delivered during another phase of sleep such as light sleep, REM sleep, or specifically during phases S1, S2, S3, or S4 of non-REM sleep.

The sleep monitor may be a subsystem or module that determines the user's sleep state. For example, in some variations, electrode recordings can be used to monitor signals generated by eye movements (electrooculography; EOG), muscle contractions (electromyography; EMG), or neural activity in the brain recorded from the scalp (electroencephalography; EEG). In other embodiments, sleep phase may be determined by one or more measurement devices (sleep monitors) that may include: accelerometers or other devices for detecting body movement whether directly by a device mounted on the user (e.g. a wristband, headband, stick-on device, etc.) or one placed nearby to detect movements for instance through a bed, pillow, or cover; devices to measure heart rate, heart beat entropy, or other features of an electrocardiogram (ECG); devices to measure respiratory rate, entropy, or tidal volume of breathing; devices to measure blood oxygen saturation ($SpO_2$), for instance by a pulse oximeter placed on a portion of the body; video monitoring of body movements, eye movements, heart beats, breathing, blood oxygenation, or other features detectable by a video camera; devices to measure body temperature such as a thermometer or an infrared sensor directed at the user; devices to measure arousal threshold for instance by presenting a sensory cue (e.g. auditory, haptic, or visual) of known intensity and monitoring various physiological parameters that indicate lighter sleep or wakefulness or by delivering a small electrical stimulus targeted to a muscle or peripheral nerve and using a recording electrode to determine the strength and extent of a reflex response; or any other suitable measurement devices currently known or hereafter developed. In yet other embodiments, multiple techniques for detecting biosignals are used at the same time and executable logic (e.g., an algorithm) for signal processing and statistical interpretation of the signals is used to determine sleep stage. In another embodiment, standard polysomnography (PSG) techniques are used to determine sleep staging.

The systems and devices described herein may include an element or set of elements to generate a stimulus. Such stimuli are typically capable of activating one or more of a user's auditory, somatosensory, olfactory, gustatory, visual, vestibular, or other sensory systems. Examples of stimulus generating elements include a screen or light, speaker, tactile electrical or mechanical stimulator, or scent-releasing device.

A learning event may be defined as the presentation of a fact-stimulus pair controlled by a computer training system, computer or Internet site, or the invention; a third party controlled moment or exposure such as a real life learning or experiential training moment, an interaction, or most generally, any event during which an aspect of the event is to be recalled or utilized at a later time. For example, when a person is studying the Fourth Amendment of the U.S. Constitution, they hear the sound of a violin or a song. In some embodiments, the fact and sound are now linked as a pair. Information regarding learning events are stored by the invention for subsequent analysis and future presentations of the fact-stimulus pair. Such presentations constitute the training phase.

The systems and devices described herein enable learning material to be compiled for a user from several sources that may include: 1) material entered into a computing device by the user or a third party that may be stored locally on the device or stored on a remote server or intermediate device; 2) material that may be in a variety of electronic formats that can be uploaded by the user or third party to a computing device for storage through the Internet on a remote server or on an intermediate device; 3) material chosen by the user from a pre-determined set of training material that may be provided by a third party or the device; 4) material that may be generated based on the user's location at a particular time or 'check-in' by a service having functionality similar to that of Gowalla or Foursquare; 5) material generated based on the user's interests as indicated by the user, by a third party, or by data mining; 6) material that may be supplied by a third party such as a teacher, work colleague, friend, advertiser, or other individual or entity; or 7) material supplied by other suitable means appreciated by one skilled in the art, that may be currently known or hereafter developed.

As mentioned above, in some variations, the learning stimulus can be an auditory, haptic, visual, gustatory, olfactory, or electrical stimulus. The invention may host a selection of stimuli that can be used by the invention or by third party devices during the learning phase. For example, a professor's presentation could use embedded audio content as a learning stimulus while lecturing to the entire classroom. Such a feature would permit all persons present in the classroom to experience fact- or content-associated stimuli for later use during sleep phases associated with memory consolidation.

In some variations, ambient, rather than provided stimuli may be used. An ambient or observed stimulus may be recorded during the learning/training event. In situations where the environment is rich in stimuli suitable for re-presentation during the sleep consolidation phase, or situations where the user is unable to receive created stimuli, the system may record one or more of the environmental stimuli, for re-presentation. This information can be transmitted to the sleep stimuli generator, another device, or to a server (e.g., stored in local or remote memory for later presentation). Any one of these devices may parse the stimuli or refine it according to signal processing or statistical interpretation techniques to make it suitable for consolidation during the sleep phase. For example, in the case where a person is studying in a café the device, which could be a program on a mobile device, will record audio through a microphone while the user is learning. Later, the audio can be filtered to find epochs of the recording where the audio has more variance than other portions of the learning period or times of the day when the user is not using the device for learning.

In some variations the system or device may synchronize with and/or harvest from third party devices or services. In one embodiment, services that provide streaming audio content can be linked to the user by their geographical location or by using or being logged in on such a service like an Internet radio service. A listing of stimuli the user was exposed to (e.g., a playlist) can be parsed to correlate stimuli with learning events. The device or system may then replay these stimuli for training during the sleep consolidation phase.

In a classroom setting, in which multiple students may attend a class where material is being taught and stimuli are presented, the system or device may apply an ambient stimulus to generate stimulus-content pairs to be recorded to a device/system locally or remotely (e.g., user database accessed through the Internet on a remote server), or through an intermediate device. The system or device may support ways that the user can implicitly connect these learning events to their accounts. For example, a user can register attendance at such an event, or, for instance, museum exhibit, by using a QR code, hashtag, or hyperlink, registering with an RFID or near-field communication device, or by checking in with a third party or socially-derived network with the functionality of a service such as Foursquare or Gowalla. The element may include a unique event identification (ID) or a combination of geographic and temporal information to ensure the appropriate event is registered.

In some embodiments, the information to be learned is directly visualized by the use of a computing device such as a desktop computer, tablet device, mobile device or the like. The system or device may be accessed as an Internet browser application, or as a standalone application. In both cases, the invention may be responsible for presenting training stimuli, such as visual cues on the computing screen, or auditory cues presented on speakers.

In some embodiments, a secondary user may access information regarding the primary user's use through the Internet. In other embodiments, the secondary user may remotely initiate the learning phase. For example, a teacher may remotely access a student's use for the purpose of tracking progress made on a lesson rubric.

In some embodiments, the invention is coupled with the use of electronic book readers. This embodiment may focus on learning a new language, or acquiring new vocabulary. The system or method may interface via software to the electronic book reader, or via an external device that communicates with the electronic book reader.

In some variations, the system/device is applied to study for K-12 government-mandated tests, other standardized tests related to application to academic institutions test preparation for standardized tests such as those required for admission to primary or secondary schools, universities, post-graduate programs, or other academic pursuits; tests required for admittance to a specific professional group including but not limited to the state bar exam for lawyers, the Certified Public Accountant (CPA) exam for accountants, the medical board exams for doctors, the Series 7 exams for brokers, or other professional tests or exams that would be known to one skilled in the art of test preparation.

The components of the systems and devices described herein may be embedded in mobile devices, either in the form of hardware and/or software running on general purpose devices such as cellular phones, portable music players, tablet computers, or other suitable portable devices currently known or hereafter developed. A mobile device may provide data connectivity to other networked parts of the memory learning system. For example, the user interface for controlling priority of learning material can be controlled via software running on a mobile device. Additionally, because mobile devices are already carried by many people, they can be used to 'check in' to locations where learning content has been, is being, or will be presented to the user. Also, ambient sounds or other sensory stimuli recorded by the mobile device could be used to generate stimuli for re-presentation during the memory consolidation phase. These recorded stimuli could be presented as recorded or processed on the mobile device, a remote server, or an intermediate device to extract features that are salient or otherwise beneficial to training. Additionally, mobile devices can provide data display of learning content, training programs, stimuli patterns previously presented or to be presented during sleep, or other content. The mobile device can be used to generate sleep quality queries or other subjective 'rate yourself' style polling; to present reminders to complete training; to generate audio or haptic stimuli; to control other devices that deliver training content or sensory stimuli. In some variations a mobile device may be configured to monitor sleep staging; to receive and/or process data about sleep staging from another device; or to function as a bedside unit to record EEG or other physiological signals sent wirelessly from a device worn by the user or placed near the user.

Thus, in one variation, the system is configured to be executed as an application on a handheld device such as a mobile phone (e.g., iPhone, Android, iPad, etc.). The application may include control logic configured to run on the mobile device and record and/or apply a sensory stimulus during the learning/training phase. The control logic may present a user interface (e.g., a control operated through the mobile phone's touchscreen or buttons) to indicate when the training mode is to start and presentation and/or recording of the sensory stimulus (e.g., a sensory stimulus generated by the mobile device or a peripheral component controlled by a mobile device or ambient sensory stimulus) is to start. Thereafter, the control logic may control monitoring of a sleep monitor to determine when the user has entered into a specified sleep stage. The sleep monitor function may also be performed by the mobile device. As mentioned, the mobile device may communicate with a separate or integrated sleep monitor (electrode, accelerometer, etc.). In some variations the controller/control logic communicates with a sleep monitor module including sleep monitoring logic configured to monitor the users sleep state. The control logic may thereafter trigger the repeat of the paired sensory stimulus.

In one embodiment, the system/device is designed to autonomously collect information without requiring explicit behaviors or actions from the user and furthermore to populate activities of the user with content relevant to the interests of the user and the capabilities of the sleep consolidation module. The system/device may use or include easily embeddable web and local or desktop widgets that can be added to webpages with methods appreciated by one skilled in the art. The devices may use implicit behavior such as cursor position, eye gaze, time on website, links clicked, and other web-user interactions appreciated by one skilled in the art to identify meaningful content. Furthermore, by coupling with third party services that represent information about social contacts of the users, or other unknown users that share similar indicators of educational interests, the device can make meaningful suggestions of content that is related or more easily trainable. These content exposures can be recorded by the widget into the sleep training device database to improve the rate of memorization. The widget is one example of a method or web element that can be easily included on any blog, news service, learning service, or information provider. Including other embeddable web technologies would function in an identical manner.

In one embodiment, the device or system may be used to alter sleep state. Sleep stage can be altered in several ways including: increasing or decreasing the frequency of a particular sleep state, increasing or decreasing the duration of a particular sleep state, or altering the intensity of brain rhythms associated with a particular phase of sleep. In the latter embodiment, methods for inducing changes in the brain rhythms associated with a particular phase of sleep could include electrical stimulation of the scalp, for instance at delta brain rhythm frequencies (generally between 0.5 and 4 Hz) with a pair of electrodes placed on the scalp.

As mentioned above, human sleep is generally described according to a cycle in which rapid eye movement (REM) sleep is followed by non-REM sleep that generally proceeds sequentially through phases S1, S2, S3, and S4. Phases S1 and S2 are generally referred to as light sleep, and phases S3 and S4 are generally referred to as deep or 'slow-wave' sleep. Light sleep can be identified by examination of body movements, such as hypnic jerks, lack of eye movements, and sleep spindles recorded by EEG. Deep sleep demonstrates enhanced power in the delta spectrum (generally about 0.5 to 4 Hz) combined with lack of motor activity. During REM sleep, apart from rapid eye movements, electroencephalogram (EEG) recordings show enhanced power in the theta bands (generally about 4 to 8 Hz).

Detecting optimum cognitive states for stimulus driven memory consolidation may be done many different ways. Each method is assessed for the accuracy of sleep phase determination, cost and computational requirements, and the burden of compliance placed on the user. Therefore, the system may be adapted to include one or more of the following techniques to determine sleep state: EEG; electromyography (EMG); electrooculography (EOG); motion during sleep (called actigraphy measured by image capture, accelerometer, microphone, or other techniques); heart rate, via accelerometer, pulse oximetry, ECG; respiratory rate, via accelerometer, microphone; and body temperature, via temperature probe or distant infrared (IR) sensor.

By applying machine learning and clustering techniques to look at previous training data for a particular user, or population of users, the rate of memory consolidation and the resolution of sleep phase detection can be optimized for a user or users. To classify such signals any of the following methods may be used, including, but not limited to: Independent Component Analysis; Principal Component Analysis; Latent Dirichlet Allocation; Naive Bayesian Classifier; K-means clustering; and Neural networks.

A device user interface may allow direct user control over stimuli exposures during the sleep phase. For example, this interface may be on the device or remote, such as on a company server, mobile device, nearby computer, or through a third party content provider, such as a college or test preparation service. The user interface may therefore allow the user to select groups of learning events that they want to be retrained on. The user or third party can alter meta data and record the importance of this information for them. The user may have opportunities to interact with other users to gain information or context into what should be learned. For example, if a user is studying for an upcoming test they can log into a website and search and select for relevant content. That information may be transmitted to a training program controller.

The system may handle the accrual of many learning events during use of the system, and may therefore use multiple specific and/or unique (to a particular learned subject and/or training session). For learned material, or material created solely for evaluation, the user may be tested on their retention of past learning events in order to establish the performance of the platform, algorithms, and stimulation parameters including stimulus strength, phase of sleep, maximum number of stimuli during sleep, optimal times of day for the learning parameters, the neurophysiologic classification of memory type, or any meta information. The results of these tests can be analyzed through clustering or data mining methods to understand how the platform should function and the user should be trained in the future. Trained sensory stimuli may be repeated immediately after the training/learning phase (e.g., during the next detected specified sleep stage) or repeated over multiple sleep stages in a single night or over multiple nights. The replay of a paired sensory stimulus may be delayed for a day or more (e.g., three days, a week, ten days), or repeated on this schedule. Multiple sensor stimuli may be repeated in a single specified sleep stage, or a single sensory stimuli corresponding to a training phase may be repeated during a single specified sleep stage.

In general, the systems or devices described herein may also include logic for efficient memory training and memory consolidation during sleep. In some embodiments, an additional aspect of feedback is used to optimize (or improve) the frequency of repetition by recording on the device itself or through the Internet on a remote server, or through an intermediate device. Established techniques for optimizing the repetition time in a spaced repetition implementation may be based on detailed mathematical models of learning and may take into account the opportunity cost of forgetting and content repetition. These algorithms can be used to improve the performance of the present invention for a particular user, subset of users, or class of users defined by age, gender, cognitive ability, interests, or any clinically relevant cause of cognitive dysfunction. In various embodiments, optimization can be applied to various components of the present invention, including the rate of repetition of training stimuli, the amount of learned material or specific set of content associated with a particular stimulus or class of stimuli, the salience of stimuli associated with training stimuli, or other aspects.

Optimum learning strategies based on the above sleep-based memory consolidation may be individualized. Parameters of the sensory stimuli associated with learned content and sleep may affect the quality of memory consolidation. These parameters may include the choice of stimulus cue, timing of stimulus delivery, quantity of learned material associated with a particular cue, and the modality, intensity, or emotional valence of the sensory input. One method for identifying optimum parameters would be to use a collaborative application that enables interaction among students, teachers, and content-providers through the Internet on a remote server, or through an intermediate device. Groups of learners may be able to share their experiences and best-parameters. Additionally, learning experts or third-party services could interface with these groups, providing advice, instructions, and/or content.

EXAMPLES

FIGS. 11 to 19 illustrate one exemplary variation of a device for enhancing memory during sleep. In this variation, the device includes several components. The device may include one or a plurality of user interface components that allow a user to control whether the device is in training mode. The user interface is generally configured so that the device may be controlled by the user without requiring additional assistance. The user interface may also allow the user to select other parameters of device function. The device may also include one or a plurality of stimulus generators (optionally referred to as stimulus actuators) capable of activating at least one sensory transduction pathway. The device may also include one or a plurality of sensors that measure user physiology to determine the sleep state of the user. The device may include logic that estimates the sleep state of a user from recorded physiological and other data. The device may also include a controller comprising control logic that determines the device function based on user inputs, the user's sleep state or wakefulness, and previous device use cases by the user.

In some embodiments, the device also includes one more outputs (user outputs) such as screens, light emitting diodes (LEDs), or other components to indicate device function. The device may also include one or more switches or other control elements for the user to control device function. In some variations the device includes a computer-readable/writeable memory component (local or remote). In some variations, the device includes a controller and control logic; the device may also include send/receive sub-systems for transmission of data between the device and an off-site computer.

Example 1

A Portable Memory Enhancing Device

In one embodiment, such as that shown in FIGS. 11 to 19, the device is configured as a lightweight, portable device that includes a plastic enclosure or housing. In the example shown, the housing is a black plastic case made by B&W International (e.g. Outdoor Case Type 05). In this embodiment, the device includes a single user interface component, including a two-position, three-pole switch mounted on the top of the enclosure. The default switch position is 'Sleep Mode'. To enter Training Mode, the user toggles the switch. The switch reads either 5 volts or ground and is connected to a digital input pin of a microcontroller contained in the device. The software installed on the microcontroller reads the state of the switch and sends appropriate control signals for either Sleep Mode or Training Mode. See below for further details about the microcontroller and the control logic achieved by software installed on the microcontroller.

Figure 12:
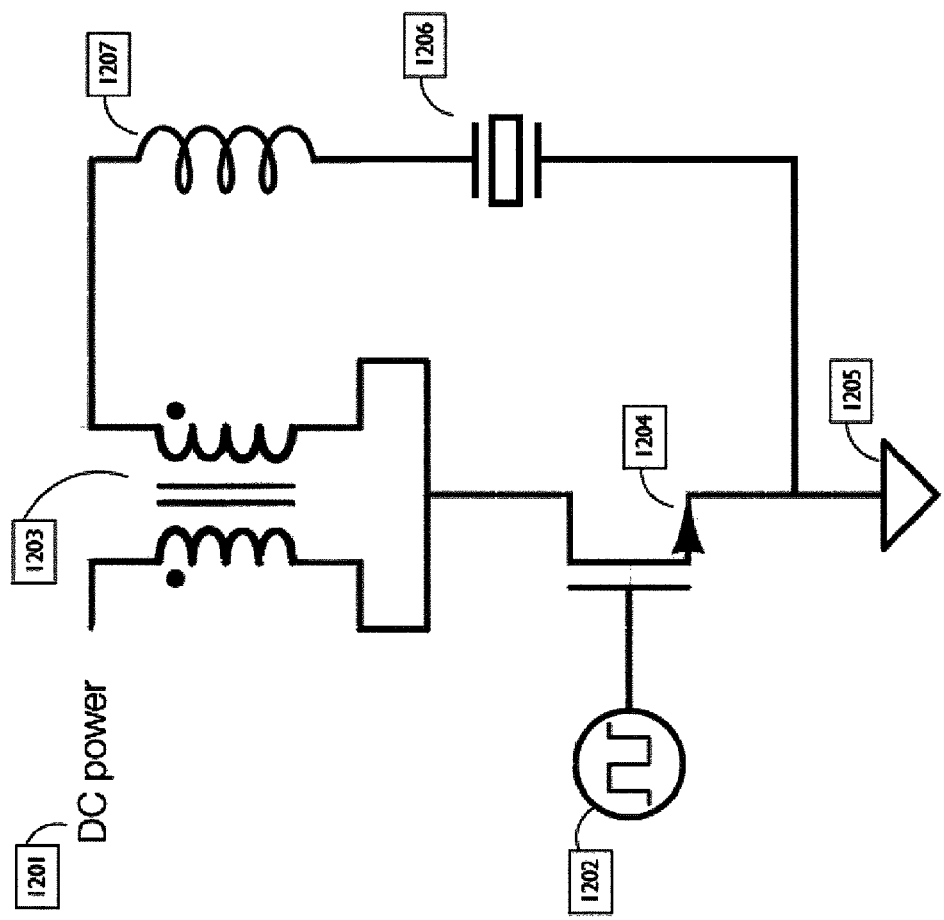
FIG. 12 shows an electronic circuit that may be used to drive a piezo atomizer for the variation shown in FIG. 11.

In this exemplary embodiment, the device contains two stimulus actuators for generating scents that activate olfactory transduction pathways in the user. The scent-releasing mechanism employs a piezo-actuator controlled by an appropriate electrical circuit to atomize a volatile liquid held in a reservoir below the atomizer and coupled to it by a wick. The electronic circuit used to appropriately activate the piezo-actuator is shown in FIG. 12. Digital control pulses oscillating at or near the resonant frequency of the piezo-actuator (1202) are sent to the electronic circuit. High pulse values to transistor (1204) allow current supplied by DC power (1201) to flow through one coil of the transformer (1203), in turn inducing currents to be sent to the piezo (1206). An inductor (1207) smooths the induced current traces without altering the oscillating frequency to generate an effective waveform for driving piezoelectric oscillation and thus releases a scent. Ground is shown at 1205.

In one variation, the circuitry, piezo-atomizer, and odorant may be similar to those described in U.S. Pat. No. 6,439,474 B2 titled "Control system for atomizing liquids with a piezoelectric vibrator" by inventor Dennis J. Denton, herein incorporated by reference in its entirety.

In this embodiment, the sleep monitor used to determine the user's sleep stage derives sleep stage from brain rhythms recorded by electroencephalography (EEG). In this example, a pair of conductive fabric recording electrodes is mounted on a headband worn by the user during sleep. The recording electrodes are oriented on the user's forehead and register both brain rhythms and electrical signals generated by contraction of facial musculature, such as eye movements known to occur during rapid eye movement (REM) sleep. The wearable EEG system includes a battery and electronic circuits to amplify, filter, and process the recorded signals. A wireless communication protocol (e.g. Bluetooth, ANT, or another wireless communication protocol) may be used to transmit the raw and/or processed signals to an EEG receiver board component of the device.

Signal processing of EEG signals may use Fourier decomposition (also referred to as a Fourier transformation) or another effective algorithm to quantify the relative and absolute proportion of signal power contained in various frequency bands. Other algorithms can be employed to reduce noise, reduce or eliminate movement artifacts, and modify other features of the recorded signal that do not relate to the biological signals of interest generated by the brain and other excitable tissue such as facial or ocular muscles. Various mathematical programming libraries facilitate simple testing and application of signal processing algorithms. For instance, Python, Matlab, LABView, or other software packages.

Sleep state logic may be executed on a processor (e.g., microprocessor) to determine from the recorded EEG data the sleep stage of the user. The logic may analyze data that extends over at least about 100 milliseconds, at least about 1 second, at least about 10 seconds, at least about 50 seconds, at least about 100 seconds, at least about 5 minutes, at least about 10 minutes, at least about 30 minutes, or longer. By analyzing data that extends over time, signals can be averaged to increase the signal-to-noise ratio. Various well-known statistical and signal processing techniques can be used for averaging, weighting signals of interest, enforcing thresholds, and applying various heuristics to distinguish specific stages of sleep such as light sleep, deep (slow-wave) sleep, REM sleep, and wakefulness. For instance, delta rhythms occur during slow-wave sleep. High amplitude, high frequency signals generated from facial muscles and eye movements occur during REM sleep. Heuristics can also be incorporated into the sleep stage processing algorithms that take into account the known order of sleep stages during the sleep cycle. The user's sleep state may be determined and used by the control logic system (see below).

A headband and signal processing unit may be charged by placing the unit on a docking station mounted on the top of the enclosure. The docking station may be connected to an EEG PCB board that includes various signal processing and wireless communication functionalities. Placing the headband unit in the docking station matches the headband unit to the EEG PCB board for subsequent wireless communication. The EEG PCB board in this example also includes a serial communication port that transmits a serial stream of data corresponding to the user's sleep state, time stamps, and other information. The serial stream is received and parsed by the programmable microcontroller.

In this embodiment, a programmable microcontroller board applies control logic that determines device function based on user inputs, the user's sleep state or state of wakefulness, and previous device use by the user. For example, an Arduino open source microcontroller framework is an effective programmable microcontroller board used in this embodiment. The Arduino system includes digital inputs and outputs, analog inputs and outputs, serial receiver, serial transmission, and power (both 5V and 3.3V). The microcontroller system in this example is programmed with custom software for controlling the various elements of the system for memory enhancement.

In one specific embodiment, the microcontroller begins by first checking whether the device is in Training Mode or Sleep Mode. If the device is in Sleep Mode, the microcontroller begins reading information via a serial communications receiver in real-time from sleep-phase detection circuitry. When the user puts on the EEG headband unit, an LED indicator (the headband LED indicator, LED1) is turned on by changing the appropriate digital output of the microcontroller to a high (5V) state. The microcontroller parses sleep stage information for the user and stores these data with timestamps in a memory component of the device. If the incoming sleep data indicates the user is in a slow-wave sleep epoch, scent delivery logic is activated by changing the appropriate digital output to a high (5V) state. The activation of the scent delivery logic is also registered on the memory component of the device with a timestamp. While slow-wave sleep is occurring, the time of operation is identified and compared to a training schedule, such that on appropriate days, scents are delivered. The device loads, reads, and parses a user configuration file stored on the device memory to determine the appropriate device function based on the training schedule for the user. The selection of which scent to deliver and the quantity of scent delivered is also determined by the training schedule. An LED indicator, stimulus indicator (the scent LED indicator, LED2), is turned on when the scent is delivered during sleep by changing the appropriate digital output of the microcontroller to a high (5V) state. The LED indicator can be left on for the remaining portion of the night so that the user can observe it upon wakening. In such embodiments, the control logic turns off LED2 at a fixed time (e.g. 2 hours) after the user wakes. When the slow-wave sleep epoch ends as determined by the registration of a different sleep state by the sleep state monitoring components of the system, the scent delivery logic is changed to inactive and scent release ceases. While the subject is in non-slow wave sleep states, scent delivery logic is not active. If the device is not being used during sleep, the microcontroller does not acquire sleep information from the associated EEG hardware and no scents are released.

If the device is in Training Mode, the microcontroller digital outputs are changed to high (5V) for LED2 and the appropriate scent delivery unit as determined by the training schedule for the user. At the end of a Training Mode session, the user toggles the position of the user interface switch and the microcontroller responds by changing the appropriate digital outputs to turn off LED2 and cease scent delivery.

Figure 11:
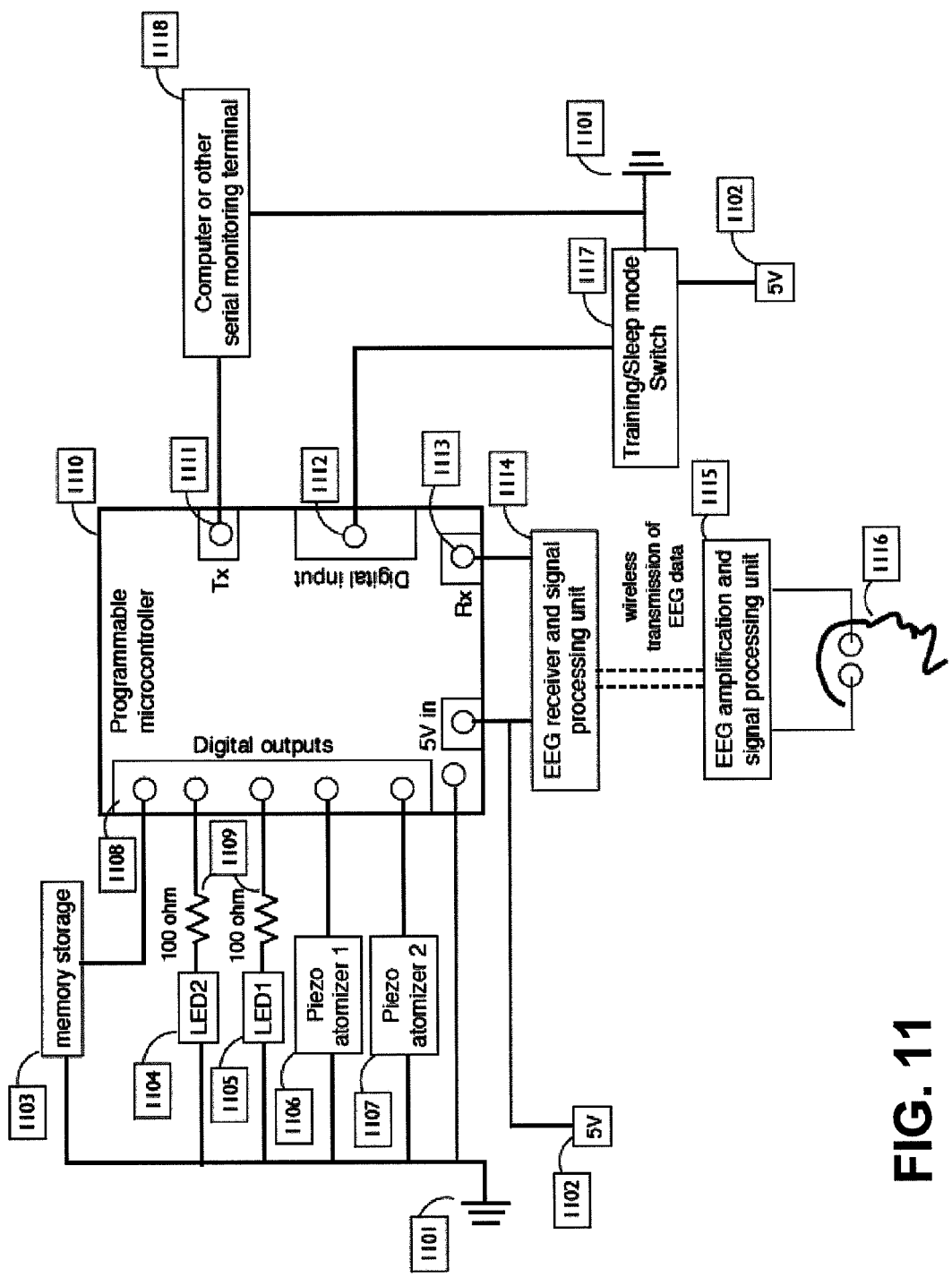
FIG. 11 is a schematic illustration of one variation of a memory enhancing device or system.

A schematic of this embodiment is shown in FIG. 11. In FIG. 11, DC power (5V, 1102) and ground (1101) are used to power the electronic components of the device. The programmable microcontroller (1110) includes connections for a plurality of digital outputs (1108), one digital input (1112), a serial transmitter (1111), and a serial receiver (1113). The digital outputs are used to control device components: LED1 (headband LED, 1105); LED2 (scent delivery LED, 1104); a memory storage component (1103); and two piezo atomizer units for delivering olfactory cues (1106 and 1107). An in-line resistor of about 100 ohms (1109) is used for each of the LEDs. The user (1116) wears a headband that includes EEG electrodes and an EEG amplification and signal processing unit (1115). EEG and sleep state information are transmitted wirelessly to an EEG receiver and (further) signal processing unit (1114) that connects to the serial receiver pin (1113) of the microcontroller. The state of the device (Training Mode vs. Sleep Mode) is determined by the position of a switch (1117) that is connected to a digital input of the microcontroller (1112) which reads either ground or 5V. In some embodiments, a computer or other serial monitoring terminal (1118) is used to monitor device function via the serial transmitter pin of the microcontroller (1111) for monitoring, debugging, and/or testing purposes.

Figure 13:
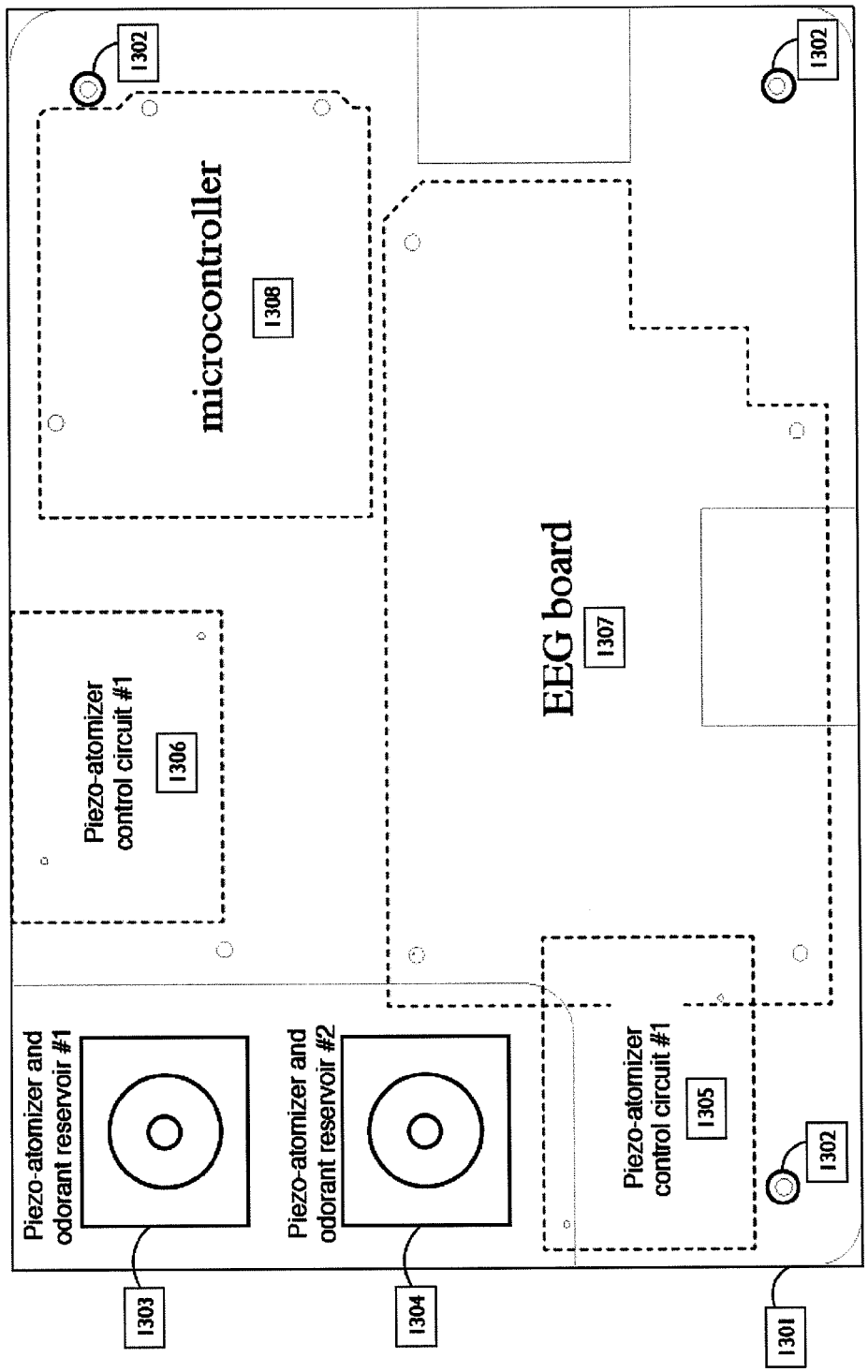
FIG. 13 illustrates one variation of a schematic for a mounting board of one variation of a device such as that shown in FIG. 11.
Figure 14:
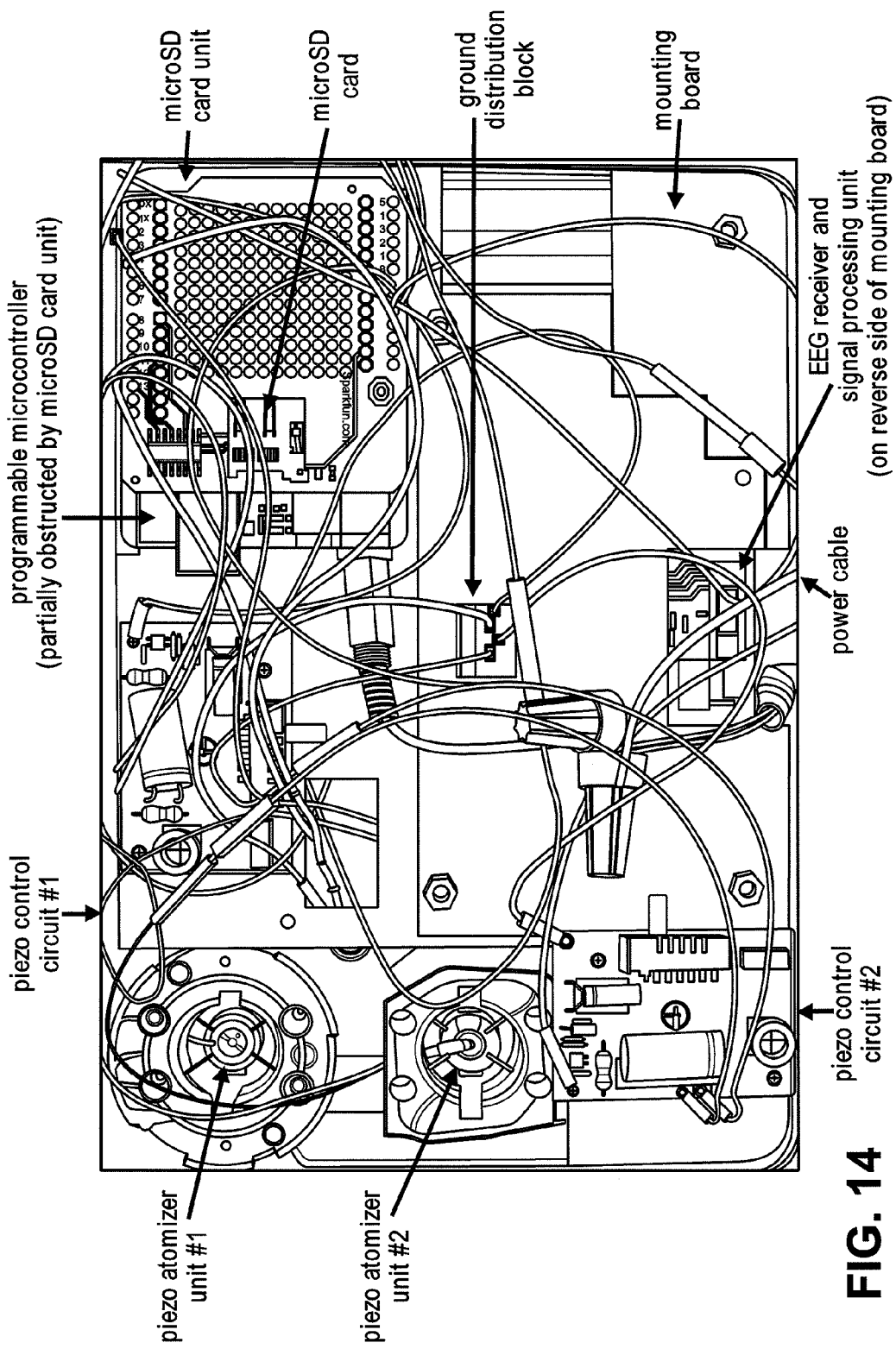
FIG. 14 shows an internal view of one variation of a device for improving memory during sleep as described herein.
Figure 15:
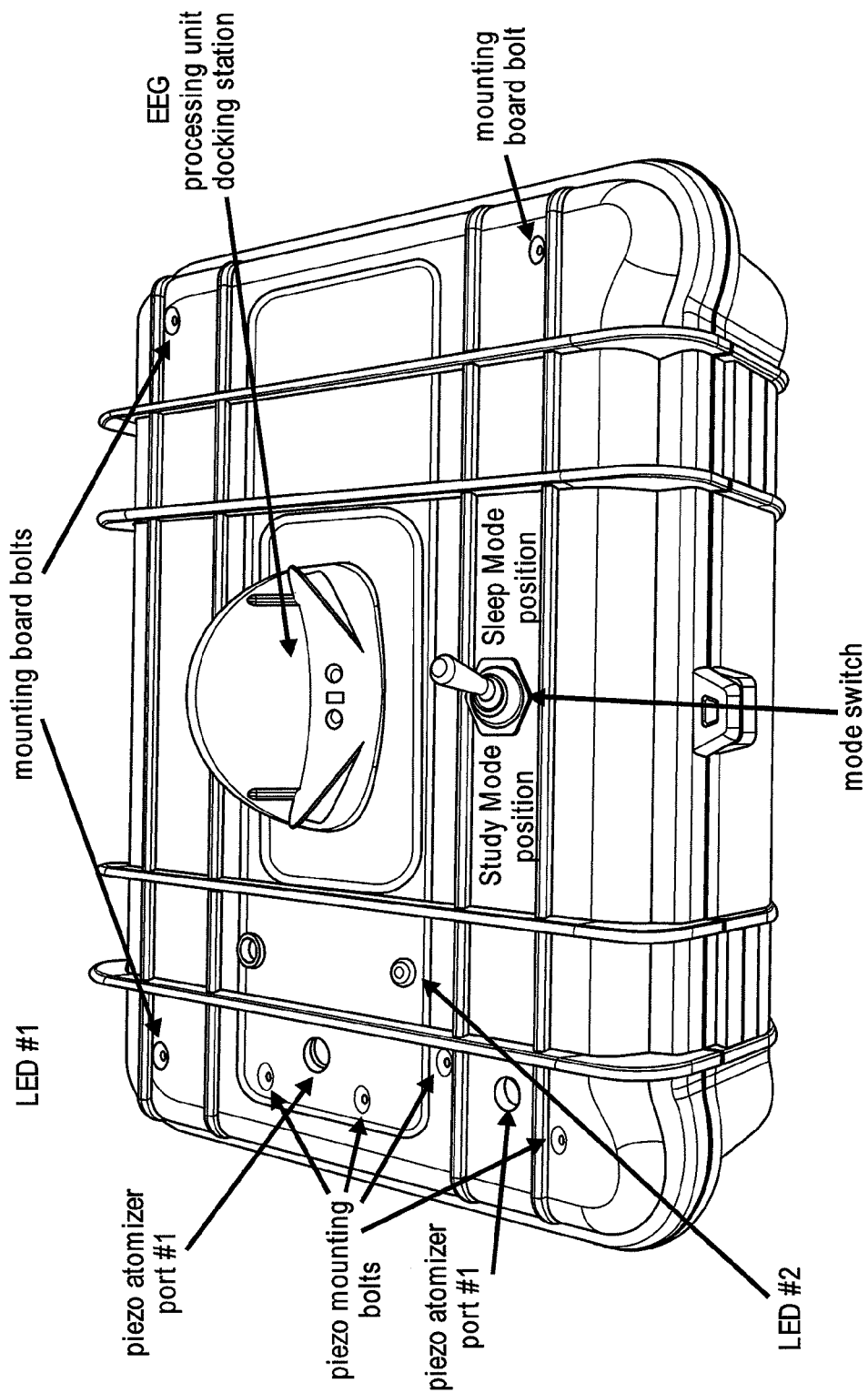
FIG. 15 shows a top view of the device of FIG. 14.
Figure 16:
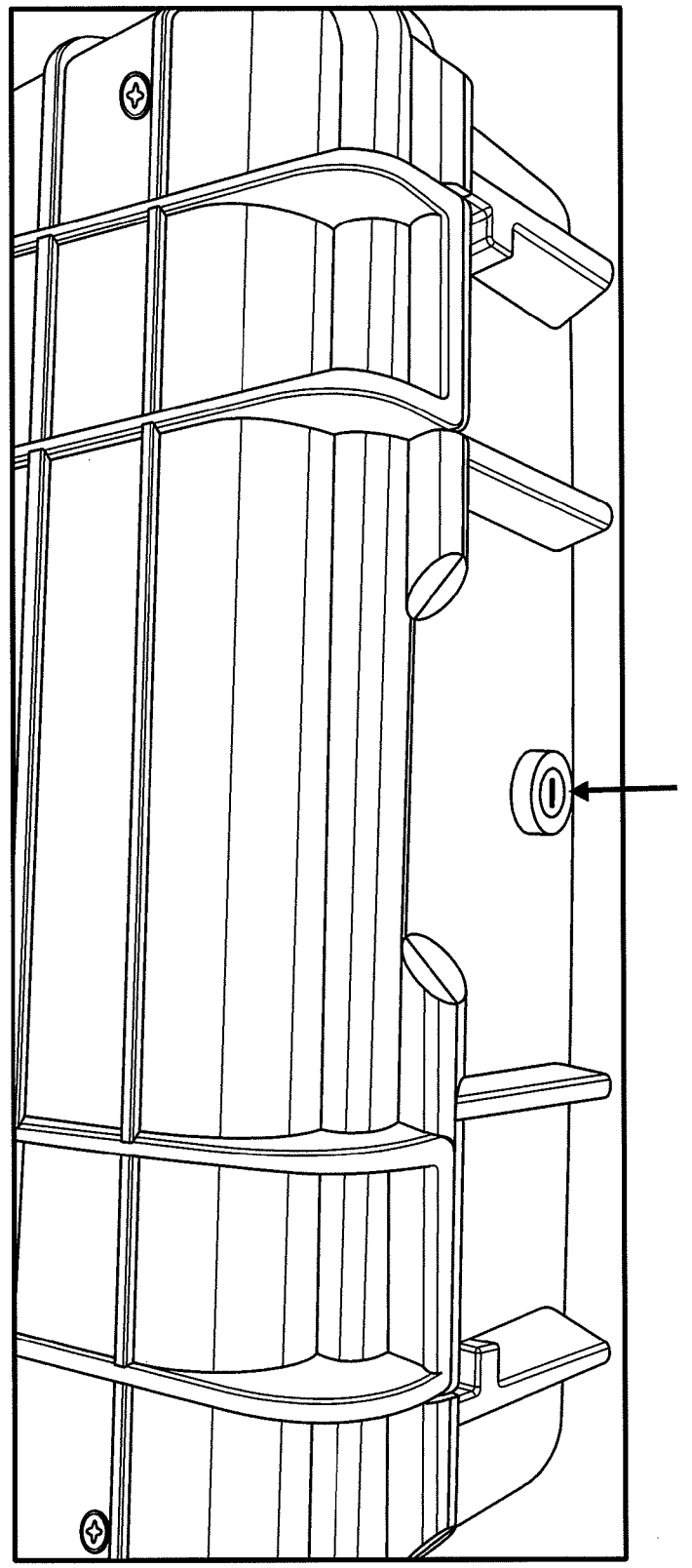
FIG. 16 shows a rear view of the device of FIG. 14.
Figure 17:
FIG. 17 shows a side perspective view of the portable device of FIG. 14.
Figure 18:
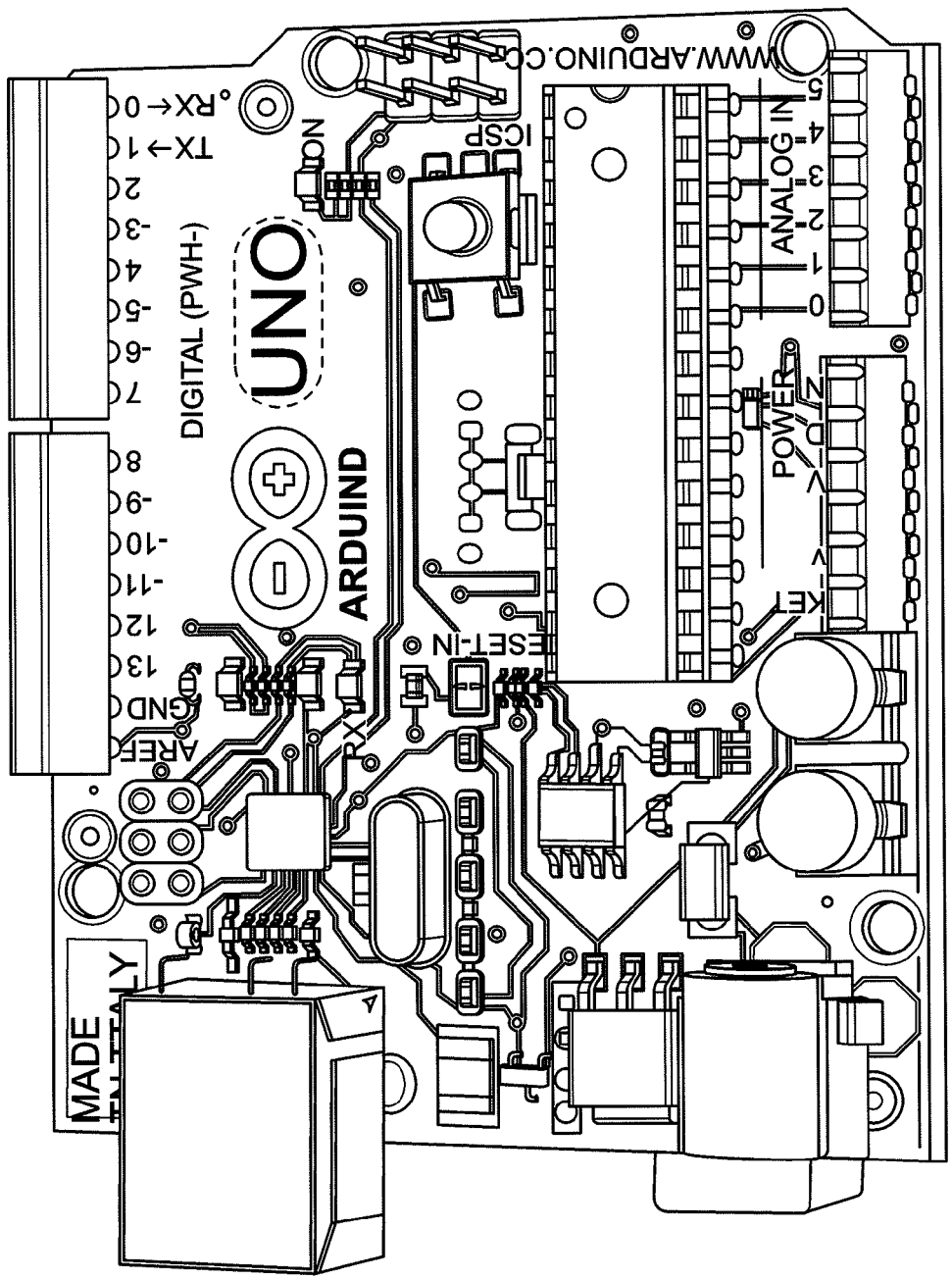
FIG. 18 illustrates one variation of a microcontroller for a device such as the one shown in FIG. 14.
Figure 19:
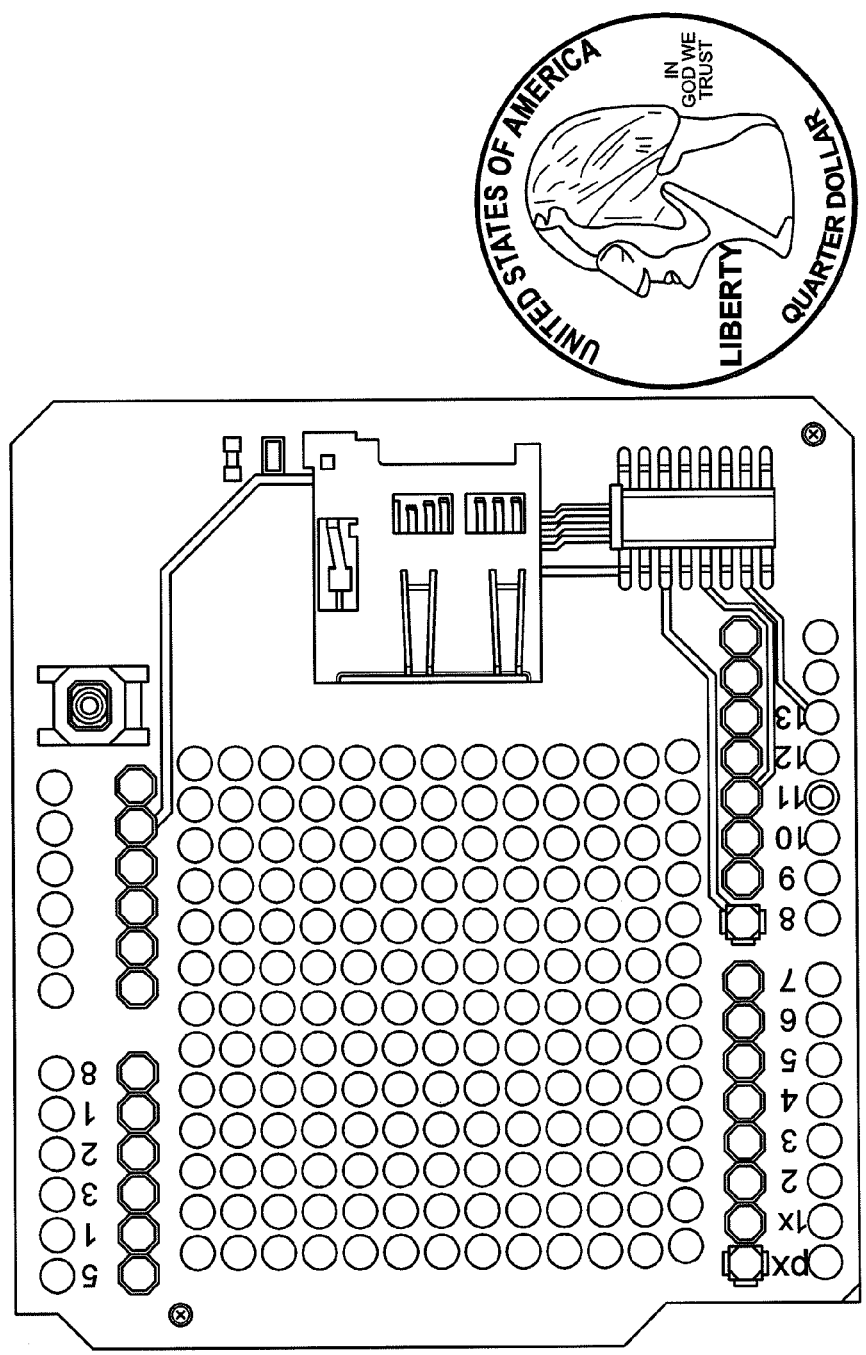
FIG. 19 illustrates one variation of a microSD card that may be used as part of the device as described herein.

In this embodiment, a custom designed mounting board (FIG. 13, 1301) is used to align and mount the various components. A form is used for alignment to drill holes of various diameters in the enclosure for mounting screws and placement of LEDs, scent ports, a power socket, and the switch. The mounting board includes pre-drilled holes for mounting screws (or other appropriate hardware) (1302). Next, the microcontroller (1308), two piezo-atomizer circuits (1305, 1306), and the EEG PCB board (1307) are mounted onto the custom mounting board (1301). The two LEDs, switch, power socket, and two piezo-atomizers (1303, 1304) are mounted to the enclosure with appropriate mounting hardware. In FIG. 13, the position of the two LEDs, power socket, and switch are not shown. Next, the mounting board is installed with appropriate mounting hardware, including spacers. Power plugs are connected to the EEG PCB board and microcontroller. Hookup wire or other soldered connectors are used to connect all components as required.

Example 2

A Memory Enhancing Device with a Computer-Readable Memory Component

Some embodiments include one or a plurality of memory storage components that permit data to be read from and written to computer-readable memory. In one embodiment, data is stored on a microSD card coupled to the programmable microcontroller for offline analysis and confirmation of device function. The stored data can also be used in case of power interruption to determine what stage of an experimental protocol a user had reached.

One advantageous feature of embodiments with data storage components is the capacity for the system to store data about the user's sleep and the times when: a user interacted with a user interface component; the state of or information presented by an indicator on the device was changed; and/or a sensory stimulus was generated. For instance, the device can write to the memory components if a switch position was changed; if an LED was turned on or off; if a stimulus such as a particular scent was released; and when a user's slow-wave sleep epoch started and ended. In advantageous embodiments, for each memory storage event, a timestamp may also be written to the memory storage. In this embodiment, storage of data about user physiology, user interaction with the device, and other information can be used in real-time or for post hoc analysis in order to improve performance of the device and/or to provide feedback to the user, for instance about their memory performance over time.

Another advantageous feature of embodiments with data storage components is the capacity for the system to read configuration files that influence the control logic output of the device and thus device function. In some embodiments, configuration files are general-purpose and indicate a particular training or studying regimen for a user.

In one specific embodiment, the system writes to a configuration file each time the user completes a particular phase of use of the device, including when: (1) a user uses the device in Training Mode for at least a minimum amount of time. The minimum amount of time may be about 10 seconds, about 30 seconds, about 1 minute, about 10 minutes, or longer; (2) an epoch of slow-wave sleep is detected in a user when the device is operating in Sleep Mode. Each of these events can be registered on each day the device is used.

In some embodiments, the memory storage components of the device are local to the device for direct (wired) communication or wireless communication via a wireless protocol such as Bluetooth or ANT. In other embodiments, the memory storage components are present on a remote server that is accessed via the Internet.

Example 3

Alternative Embodiments of Memory Enhancing Device

In alternative embodiments, the enclosure of a portable memory enhancing device is made of plastic, wood, metal, or another suitable material. Other embodiments of a memory enhancing device use one or more alternative or additional user interface components that allow the user to control device function, chosen from the list of: touchscreen, buttons, switches, and other mechanical or electrical input or selection mechanisms. In some embodiments, the memory enhancing device includes one or a plurality of screens, light emitting diodes (LEDs), or other components to indicate device function by visual, auditory, tactile, or other means. These embodiments are advantageous for indicating to the user the device mode, history, options, and other information.

In some embodiments, alternative methods for releasing a scent such as an aerosol spray or another technique known to those skilled in the art of generating smells can be used. In further embodiments, a plurality of scents can be delivered to the subject. In embodiments capable of delivering multiple odorants, distinct scents can be generated by releasing multiple scents concurrently or within a sufficiently short period of time that the volatile compounds are present concurrently in the user's environment. In such embodiments, the ratio of the two or more scents released can be varied to generate a larger number of distinct olfactory percepts.

In alternative embodiments, the stimulus actuators generate an auditory stimulus. For instance, the auditory stimulus can be generated by speakers contained in the device. Alternatively, the auditory stimulus can be generated by headphones connected to the device with wires or via a wireless protocol such as Bluetooth. In some embodiments, the intensity of the auditory stimulus is adjusted based on the current sleep state of the user, such that the stimulus does not disrupt the user's sleep. In some embodiments, physiological measurements of sleep stage and/or sleep depth are used to adjust the intensity of auditory stimuli. A similar strategy of changing stimulus intensity as a function of sleep state of the user can be used for other modalities of stimuli as well.

In alternative embodiments, the stimulus actuators generate a tactile stimulus. A tactile stimulus can be generated by a wearable component attached to the user such as with a headband, wristband, piece of clothing, fashion accessory, or other means of coupling physically to the user. The tactile stimulus can be generated by any means that activates somatosensory transduction pathways for instance by activating peripheral receptors that mediate touch, temperature sensation, or pain. In various embodiments, tactile stimuli can be generated by a piezo actuator, buzzer, heating element, or other mechanism known to one skilled in the art. Examples of non-contact tactile stimulus actuators include ultrasound transducers, components that generate a magnetic field, and other non-contact means to activate somatosensory transduction pathways.

In alternative embodiments, the stimulus actuators generate a visual stimulus. Advantageous visual stimuli are those that are low resolution and thus could be effectively transmitted both to an awake user in Training Mode and a sleeping user in Sleep Mode. Advantageous low resolution visual stimuli contain positional and light level information but are not intended to transmit high resolution information. For instance, a white or colored light in a particular area of the visual field such as the left upper visual field. In some embodiments, red light is used as an advantageous color due to its relatively higher transmission through closed eyes relative to other wavelengths of light. In some embodiments, visual stimuli are time-varying. Temporal patterns may be regular (e.g. sinusoidally varying light intensity), irregular, random, or pseudo-random. Visual stimuli may be generated by one or a plurality of LEDs, an OLED screen, or other controllable light-generating source. The visual stimulus actuators may be mounted on eyeglasses, a hat, or other wearable forms of clothing or accessories.

In alternative embodiments, the stimulus actuators generate a gustatory stimulus. In such embodiments, a taste can be delivered via appropriate hardware coupled to the device that delivers tastant molecules to the lips, tongue, palate, and/or mouth. In one such embodiment, an orthodontic retainer securing to the teeth and palate, additionally comprises microfluidic chambers holding concentrated volumes of tastants (e.g. essential oils, artificial sweeteners). Upon receipt of a wireless control signal, a chamber releases its contents, which come in contact with taste buds on the palate and tongue.

In some embodiments, a plurality of stimulus actuators is used to deliver stimuli chosen from two or more sensory modalities. In such embodiments, a more diverse set of stimuli can be generated, permitting a larger number of unique stimuli to be delivered to a user during extended, repeated, or ongoing use of the device.

Example 4

Instructions for Use of a Memory Enhancing Device

In this example, the user may be provided with instructions for use including several steps that will be described in instructions. Instructions may be written on paper, electronically, or may be pictorial (e.g., ideograms) or the like.

For example, the user may be instructed to place the memory enhancing device at a convenient bedside location such as a nightstand and to plugs the power supply into a wall socket. In this case, the user will study while sitting in bed near the device. Alternatively, the user may put the memory enhancing device near them during study at an alternate location at home (for instance at a desk or table) or at a cafe, library, or other suitable location for study. In this use case, the user will need to remember to bring the device to their bedside before going to sleep.

In a second step, the user commences a study session by toggling the switch to Training Mode. When Training Mode is selected, control signals are generated by the microcontroller to generate stimulus (e.g., a release a scent) and turn on a first light emitting diode (LED1) mounted at the top of the enclosure, indicating that the stimulus has been delivered (e.g., scent releasing mechanism is activated). In one example of a study to examine the efficacy of the device (discussed in detail below), the user may be asked to study a particular set of content or play a web-based brain game that tests memory function. The Training Phase may last for an appropriate amount of time, for example, from about 2 minutes to about 2 hours, from about 2 minutes to about 1 hour, from about 5 minutes to about 45 minutes, from about 5 minutes to about 30 minutes, from about 5 minutes to about 15 minutes, etc.

At the end of the training phase, the user moves the switch to the Sleep Mode position. The scent generation ends and LED1 is turned off. In some variations the system may automatically move the switch to the sleep mode position or simply change the mode of the system internally. For example, the system may be switched to the sleep mode (or sleep phase monitoring mode/sleep consolidation mode) by a timer or by detecting when the subject is sleeping.

The user may be instructed to wear the sleep monitor (e.g., headband) when they go to sleep. The device may indicate when the headband is successfully recording and transmitting to the device by turning on a second LED (LED2) mounted on the enclosure. In one example, the stimulus (e.g., scent) presented during an earlier training session will be presented again while the subject is in an epoch of deep (slow-wave) sleep. The user will not be consciously aware that the scent is presented during sleep. They will not be awoken. For the first deep (slow-wave) epoch of the night, LED1 is turned on and remains on until after the user wakes up. Thus, in Sleep Mode, LED1 indicates to the user upon awakening whether the scent was released during sleep.

At the end of the night, the user may place the headband back on the docking station for charging.

Example 5

A Memory Enhancing System Based on an iOS Device (or Other Mobile Device)

In one embodiment, the component functions are achieved by a third party mobile device such as a cellular phone, portable music player, or personal digital assistant. In this embodiment, a custom application running on the mobile device coordinates the components to produce the memory enhancing effect.

In this embodiment, the user interface component is the touchscreen interface, keyboard, or other user interface of the mobile device. For instance, the user selects the desired Mode (Training Mode or Sleep Mode) using the touchscreen, keyboard, or other interface of the mobile device. In some embodiments, the screen of the mobile device can be used to indicate device function such as whether the device is in Training Mode or Sleep Mode.

In this embodiment, the mobile device also functions as a stimulus generator. Most modern mobile devices contain speakers and/or a headphone jack, as well as the requisite hardware and software to generate arbitrary auditory stimuli. In alternative embodiments, the mobile device can control the delivery of other modalities of stimuli through peripheral accessories that can be activated via wired connections and wireless protocols such as Bluetooth or ANT. For instance, a stimulus generator capable of delivering one or more olfactory stimuli could connect to the mobile device and be activated at the appropriate times based on the control logic of the custom application running on the mobile device.

In this embodiment, the mobile device can also be used as a component to measure user physiology that corresponds to sleep state. Many mobile devices include accelerometer and/or gyroscope components that measure movements of the mobile device and can be accessed by applications running on the mobile device. By placing the mobile device on the bed, user movements during sleep can be measured to acquire the necessary data to estimate sleep states according to the well-established technique of actigraphy. Similarly, the mobile device includes a microphone that may be used for monitoring sounds arising from body movements, as well as those arising from user breathing patterns. Both types of sounds may be used to assess sleep state. In alternative embodiments, the mobile device can be used to acquire other physiological data related to sleep state either directly or via peripheral or accessory components.

In this embodiment, the algorithm for determining sleep state based on recorded physiological data is a component of the software application running on the mobile device. Most modern mobile devices include hardware components with sufficient memory and processing power to run the requisite algorithms in near real-time.

In this embodiment, the controller logic that determines device function based on user inputs, the user's sleep state or wakefulness, and previous device use cases by the user is also achieved by the custom application running on the mobile device. Mobile devices also contain built-in memory for storing data about the user, the device function, or other data required for proper memory enhancement using this device. Mobile devices have wireless transmission capabilities for sending this data to another computer or remote server via the Internet.

When this embodiment is placed in Training Mode, the device delivers an appropriate contextual sensory stimulus. In some embodiments of the mobile device version of this invention, the application also presents Training Content on the screen of the mobile device, including appropriate user interface components and functions. In this embodiment, as the user studies the lesson, the device produces the contextual stimuli.

In Sleep Mode, set by the user prior to sleep onset or activated automatically based on the signals derived from accelerometer and/or gyroscope components of the mobile device, the mobile device loads the appropriate contextual stimuli from the learning database and begins collecting sensor data related to the sleep physiology of the user. The mobile device may collect this data using built-in sensors such as an accelerometer, gyroscope, microphone, or ambient light level detector, or communicate with accessory sensory devices. The mobile device applies an appropriate algorithm to the collected data to estimate the current sleep state of the user. When the sleep state matches the trigger state (e.g. slow wave sleep), the mobile device generates the appropriate contextual stimulus.

To assess the effectiveness of a particular embodiment of the device, it is advantageous in some cases to use a test or other assessment of cognitive function, learning, and/or memory. Such tests can take many forms, including standardized tests, assessments of different cognitive domains (e.g. language, math, reasoning, foreign language, history, motor performance, and motor learning), tests administered by a trained professional (e.g. a teacher, school counselor, or clinical social worker), self-administered tests, computer- or web-based brain games, and other formal or informal assessments that can be tracked, quantified, and/or normalized.

One specific example for testing a user's memory employs a visuospatial game played via the Internet by using a web browser. The visuospatial game operates in a training phase and a testing phase. In the training phase an image is displayed near the center of the screen. After about several seconds, a target is displayed elsewhere on the screen for about another several seconds. Next, the image and target disappear and the background is displayed for about several seconds. The presentation of image and target (with a different, randomized or pseudo-randomized location) are repeated for different images. In various embodiments of the game, more than about 2 image-target pairs are presented, more than about 5 image-target pairs are presented, more than about 10 image-target pairs, more than about 20 image-target pairs, more than about 50 image-target pairs, more than about 100 image-target pairs, or more image-target pairs.

In the testing phase of the visuospatial game, the set of images displayed for a particular user during a training session are presented again. The user is instructed to use the mouse or touch screen interface to choose the location of the screen where they remember the target being presented. After the user clicks or touches to indicate a location, the actual location is indicated with a target displayed for about several seconds on the screen, and the distance between the indicated and target position is recorded. Next, the subsequent image is presented and the user again selects the remembered target location. The order of image presentation may be the same as during training or the order of the images may be shuffled. A testing session may be repeated one or more times. The number of times the testing session is repeated may be fixed (e.g. three repeated testing sessions) or the number of repeated testing sessions may be chosen according to a threshold of minimum performance. Due to the feedback about the correct target location provided after each image presentation, subjects generally improve their performance over multiple testing sessions.

The accuracy with which users select a remembered target location can be compared between different memory enhancement or memory disruption conditions to determine the extent of memory modulation, if any.

Figure 20:
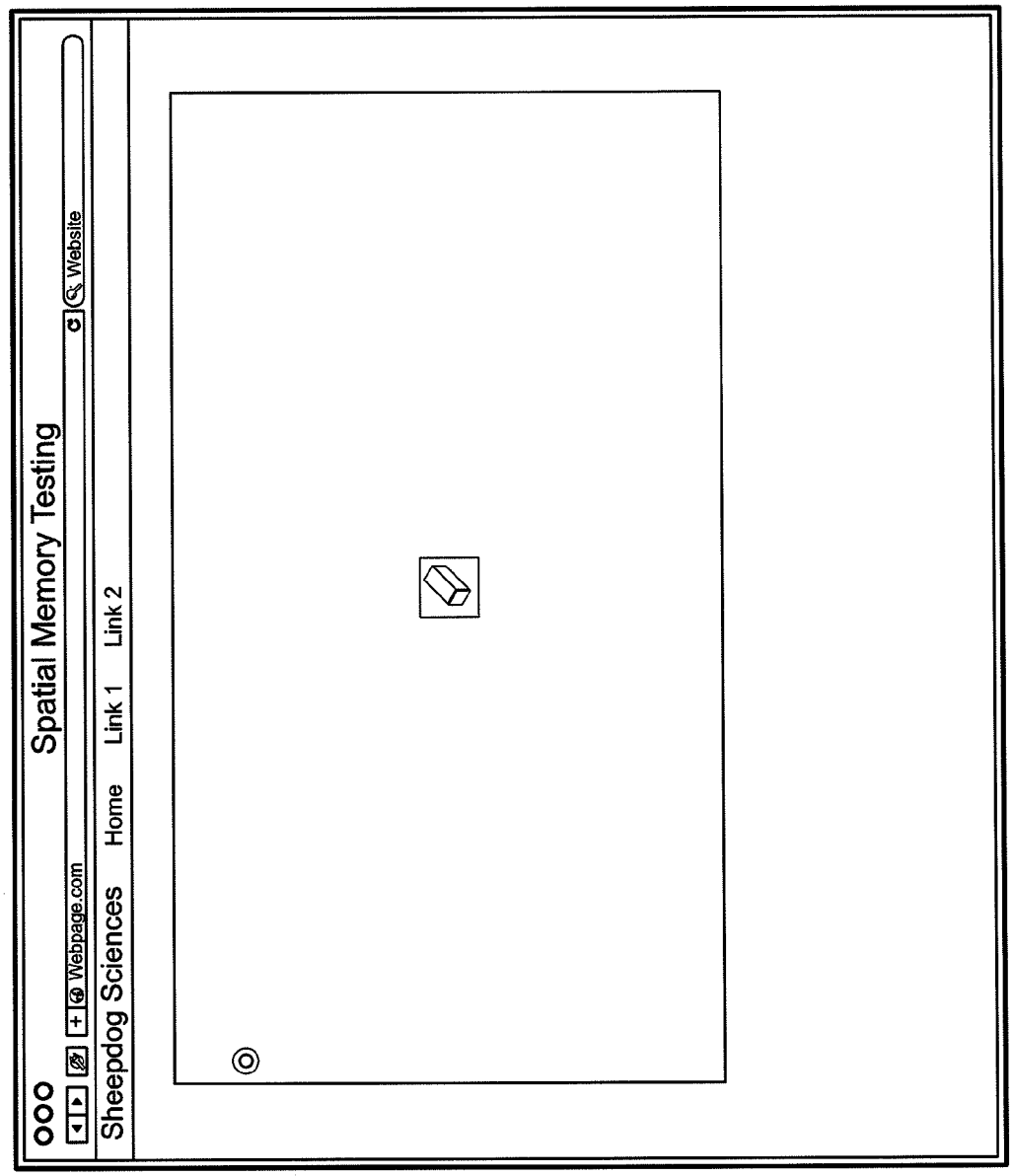
FIG. 20 shows an exemplary computer screen capture showing a visuospatial memory game used in a prototype system, in training mode when the user is taught the location of each object.
Figure 21:
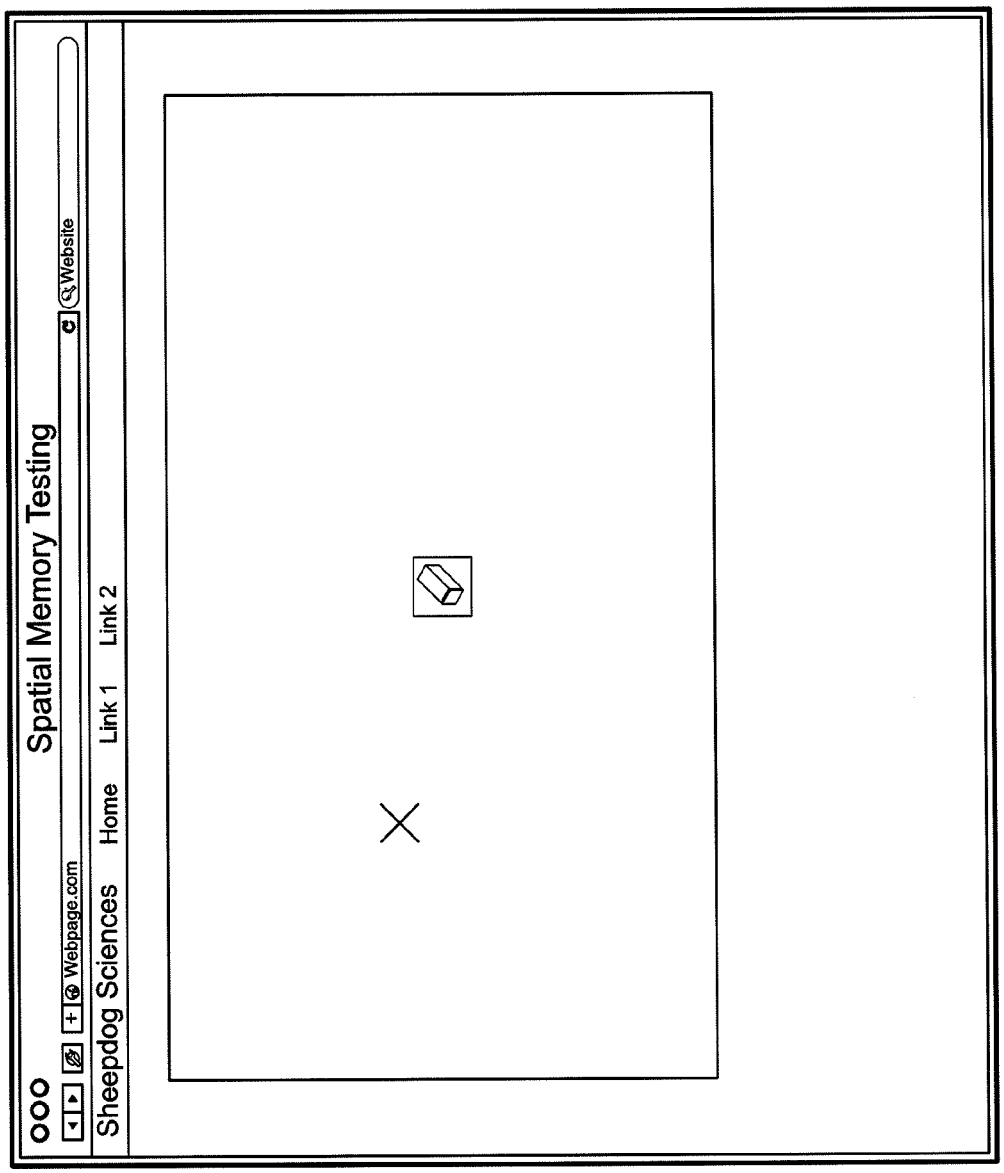
FIG. 21 shows another exemplary computer screen capture showing a visuospatial memory game after the user clicks the location at which they remember the target object to have been previously presented.

Using an embodiment of a device for enhancing memory similar to that shown in the schematic of FIGS. 11-19, healthy adults were tested in a visuospatial memory task as just described, and similar to that shown in FIGS. 20 and 21. The results are summarized in FIG. 22. The memory task for training was a visuospatial 'concentration'-style game in which the subject learns the location of pairs of identical images.

During training, a scent was released by an atomizer controlled by a microcontroller. The subject practiced the memory game in the evening, and a baseline memory score was determined. The subject slept wearing the sleep monitor (forehead electrodes) of the system for monitoring brain rhythms. When SWS was detected, the portable, user-actuated system including the controller (microcontroller), which was placed at the subject's bedside, activated a scent atomizer in the experimental condition. In the placebo condition ('vehicle', FIG. 22), the scent was released during training mode when the subject was practicing the game but not during sleep. In the morning, subjects were tested on the memory game practiced the preceding night.

Figure 22:
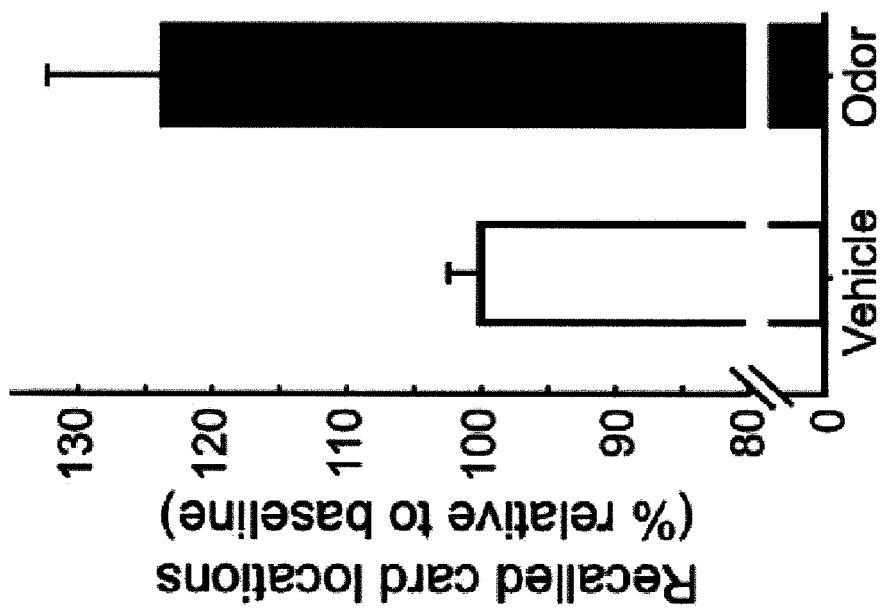
FIG. 22 is a chart showing exemplary results from the test task using a prototype as shown in FIGS. 14-17 when subjects are trained using a memory game as illustrated in FIGS. 20 and 21.

Pilot data were collected using software and hardware recording the results of the trial in subjects using the device, and in subjects for whom the memory consolidation step was not performed. This preliminary data (n=3 per condition) showed successful enhancement of memory. Subjects recalled a larger proportion of image locations in the morning under the experimental conditions relative to the placebo conditions (FIG. 22).

To save stimuli resources and help the user relate highly connected information, when possible the system or user may choose to use an identical stimulus or similar stimuli to train multiple, highly linked pieces of learning content. For example, a quack could be played to remember facts both about the geography of the United States and Presidents of the United States.

In some variations, a system for modulating memory consolidation may be more effective if it includes presenting effective contextual sensory stimuli during wakefulness when memory encoding occurs (e.g., during studying or experience of events that are desirable to be remembered) as well as presenting related sensory stimuli during sleep when memory consolidation occurs. A computerized "learning database" is an effective system for selecting, prioritizing, and scheduling which stimuli to present at a particular time of wakefulness or sleep for a particular user. In some variations, the learning database is stored on machine-readable memory contained on a system for modulating memory consolidation wearably attached or near a user. In an embodiment, the learning database is a SQLite or other database stored on a user's mobile handset (e.g. iPhone, iPod touch, Android phone) or tablet computer (e.g. iPad or Android tablet). In an embodiment, the learning database is stored remotely on a computer or server accessible through the Internet (e.g., Amazon S3 or Dropbox). Any database structure that enables storing, querying, and delivering information related to the memory consolidation process can be used. In some embodiments, custom database structures are used for a learning database.

Effective selection of contextual sensory stimuli for a specific training session may support modulation of memory consolidation during sleep. An important feature for such a system is a learning database configured to store information about what sensory stimuli have been presented to or experienced by a user. In some embodiments, the learning database stores data that was or can be used to generate a sensory stimulus as would occur for a database configured to store audio files (e.g. mp3 files) that can be played through appropriate computer and speaker systems. In other embodiments, the learning database is configured as a relational database and stores a reference, ID number, link, or other symbolic reference to a particular sensory stimulus. For instance, the descriptive tag 'rose smell' can be stored in the database. In some variations, a processed version of a contextual stimulus is stored in the learning database. Dimensional reduction analysis techniques (e.g. principal components analysis, adaptive dimensional reduction through supervised learning, spectral analysis within key frequency bands) can be applied to sound files for instance to identify dominant features in a particular sound, song, or audio recording. Sounds of birds chirping or waves crashing may be distinct from each other yet share common features as defined on the basis of the distribution power in various acoustic frequencies or other temporal features of the auditory stimulus.

In some variations, an appropriately configured learning database is used to select contextual sensory stimuli that are sufficiently distinct from contextual sensory stimuli previously presented to the user by a system for modulating memory consolidation. In some embodiments, a computerized algorithm compares database entries about previous contextual sensory stimuli presented to a user with a new set of potential contextual sensory stimuli, then selects one or more new stimuli to present. In some embodiments, several stimuli are selected and they are prioritized to determine the order they will be used as contextual sensory stimuli during user's study session.

In some variations, the algorithm is configured to select contextual sensory stimuli that are perceptually or statistically distinct from previously presented stimuli. Actual stimuli and/or pointers to previously presented stimuli may be stored in the learning database. In embodiments with a learning database configured to store a reference, pointer, or other symbolic representation of a contextual stimuli (rather than a machine-readable version of the stimulus itself), the system further comprises a system to access a stimulus from the reference, pointer, or symbolic representation—or access additional information (such as descriptive hashtags, i.e. 'waves crashing', 'sound', 'environmental')—in order to classify the sensory stimulus.

In some variations, an algorithm for comparing potential new stimuli to previously presented stimuli is configured to have strict criteria for selecting contextual sensory stimuli such that a new sensory stimulus to be presented cannot be similar to previously presented stimuli. For instance, if a subject has previously been presented with a sound of waves crashing on a beach, a subsequent similar stimulus, such as the sound of a waterfall, could be excluded. In other variations, a potential new sensory stimulus that is similar to a previously presented sensory stimulus is presented with low priority (i.e., only if needed due to extensive study sessions by the user such that all higher priority contextual stimuli have already been presented).

In some variations, an algorithm for comparing potential new stimuli to previously presented stimuli is configured to have a loose criteria, such that a similar but distinct stimulus is chosen to be presented to a user. In this embodiment, a recording of waves crashing on a beach could be chosen so long as it was not identical to a previous recording of waves crashing on a beach presented to the user during a study session and/or sleep session. In some variations, a statistical likelihood of a sensory stimulus being perceptually distinct from another stimulus is determined based on an algorithm (e.g. weighting of dominant principal components) and used as a criteria for selecting a sensory stimulus.

In some variations, similar sensory stimuli are intentionally chosen when similar content is presented in a study session. The system can be configured to select sensory stimuli from a similar modality and/or with similar perceptual, conceptual, or statistical features. The system is configured to determine what type of study material is being studied (and in some cases presented by the system) and automatically match a particular type of sensory stimulus to it. In one exemplary variation, environmental sounds (e.g. birds chirping, waves crashing) are associated with study of math concepts; while musical electronic (non-environmental) sounds are associated with engineering concepts. Geometry concepts similar to math would then be associated with a similar environmental sound such as the sound of wind through leaves on a tree. A higher degree of specificity between stimuli and concepts would also be beneficial in some contexts, such as when symphonic recordings dominated by string instruments are associated with algebra concepts and jazz recordings featuring saxophone solos are associated with study of geometry concepts.

In some variations, the set of potential contextual sensory stimuli are the same sensory modality (e.g. all sounds, all smells, all tactile stimuli), while in other embodiments the set of potential contextual sensory stimuli include stimuli to activate different sensory modalities. In another variation, hybrid sensory stimuli that include stimuli for activating more than one sensory modality are included (e.g. a sound and a smell presented together or with a fixed temporal interval).

Systems and Methods for Selecting Distinct Contextual Sensory Stimuli for One or More Specific Training Sessions The hardware and software of a learning database can be configured in several ways for generating, selecting, prioritizing, and/or scheduling contextual sensory stimuli to be presented during one Study Mode period. The learning database is further configured to store the identity (or a reference to the identity) of any contextual sensory stimulus presented during a Study mode period, so that it can be scheduled for re-representation during sleep. As described in greater detail below, in some embodiments, the learning database is configured so that some contextual sensory are de-prioritized for re-presentation during sleep and accordingly may not actually be re-presented during sleep.

In some variations, a learning database system is configured so that contextual sensory stimuli are pre-selected before a training session begins based on the content being studied or based on features of an experience to be remembered. Pre-selected stimuli can be universally associated with particular study content that is commonly studied by a population of users (such as SAT vocabulary words or human anatomy terms required for passing a medical school exam). In this manner, the pre-selected contextual stimuli are not scheduled to be presented at a particular time or in a particular order. Rather, the learning database is configured to have an association between a set of learning content and one/or more contextual sensory cues. When a user studies that particular content with a memory enhancement system, the learning database is queried, the appropriate sensory cue or set of cues is identified, and the learning database transmits the appropriate cue to be presented. One variation of this form of the invention would be a clip of a Bach symphony being associated with the names of the bones of the hand. In some embodiments, the learning database pre-selects a set of cues and associates them with a particular user or set of users in the system, then determines the quality of memory enhancement for the associated learning content and cue identity for each of the cues. Over time, as more data is acquired concerning the effectiveness of particular cues for enhancing memories related to particular content, the system can use artificial intelligence or other algorithms to optimize cue-content association and update the learning database accordingly. In an embodiment, one component of the learning database is a quantitative or qualitative metric of confidence in the effectiveness of a cue-content pair. The confidence metric is then updated as new data is acquired, incorporated in the learning database, and used as an input to an appropriate statistical algorithm.

In some variations a learning database system is configured so that contextual sensory stimuli are pre-selected before a training session begins for a particular user. Features of contextual sensory stimuli selected or prioritized for association as a sensory-tag cue include sensory modality, intensity or salience, length (e.g. how long is an auditory clip; some individuals may have longer attention for a cue while other users may require cues to change more quickly as a function of content being studied), and other features of the contextual sensory cue. For embodiments that use auditory cues, features of auditory clips can be used to prioritize or select cues, including environmental sounds (e.g. birds chirping or highway traffic), songs (symphonic, clips from live music shows, riffs from a particular instrument, etc.), or abstract electronic sounds. In an embodiment, the learning database is configured to pre-select sensory cues based on a user's demographics, interests, etc. (age, sex, interests, friends' interests, any disabilities or sensory issues (color blindness, high frequency hearing loss, etc.)).

In some variations a learning database system is configured so that contextual sensory stimuli are pre-selected before a training session begins based on a user's learning environment. The learning environment can be detected automatically by determining where the user is located. This can be accomplished by GPS components of a tablet computer or phone handset (e.g. iPhone), by proximity sensors (e.g. RF) associated with a particular location, or by the user manually indicating their location via a user interface on a static computerized system (e.g. one fixed in place at the study environment, as in a library) or via another messaging system (e.g. text message, tweet, entry into a dedicated web page, etc.). In this variation, the learning database is configured to have an association between a location, environment, or behavioral context for the user (e.g., as a student in a classroom) and one or more contextual sensory stimuli. For instance, smells are good in a private studying environment, as well as in a shared learning environment, but the issues with air flow and controlling intensity of stimulus can be a problem if a user enters Study Mode while outside or in a large room (e.g. a large lecture hall). Similarly, the learning database can automatically prioritize sounds as a contextual cue—and even particular types of sounds—if a user is in a public location and using headphones. In some embodiments, statistical algorithms are used to make a 'best guess' about a user's location or environment.

In some variations a learning database system is configured so that contextual sensory stimuli are pre-selected based on the time of day, day of the week, or time of year. In some variations the learning database is configured to select particular cues at a particular time of day. In an exemplar variation, calmer sounds are chosen during evening study times while more energetic sounds are selected in the early morning or after lunch when a user may benefit from cues that are energizing. In some variations the learning database is configured to select particular cues for a particular day of the week. Similar to how the system assigns, selects, or prioritizes sounds based on the time of day, users may benefit from having cues that are more energizing on Mondays and require a different set of cues on the weekend. In some variations the learning database is configured to select particular cues for a particular time of the year. In an exemplar variation, 'holiday' themed cues (i.e. songs related to Christmas, Hanukah, etc. or smells associated with the holiday season such as egg nog) may be effective. In other embodiments, cues are pre-selected to provide contrast with common environmental stimuli occurring at that time of year (e.g., winter holiday themed cues in July). In this exemplary embodiment, the learning database may be configured not to select cues present in the user's environment, so that during the winter holidays, cues would be selected to have little perceptual or statistical relationship with sounds, smells, or tastes generally associated with this time of year.

In some variations a learning database system is configured to select context sensory stimuli in a pre-determined order. In an exemplar embodiment, 10 sounds or 5 smells are pre-selected for a user's first study session, and a new set of sounds and smells will be presented on subsequent study sessions. In some variations a user orders a 'pack' of new sounds through a web interface or 'in app' purchase, then these purchased cues are presented in a fixed order. Users can select individual cues that they like (or sets of cues), similar to how individuals can purchase ringtones for their phone.

In some variations a learning database system is configured to select context sensory stimuli algorithmically. In some variations, the learning database is configured to have software for achieving a desired sensory cue-selection algorithm. In some variations the selection of a sensory cue occurs approximately in real-time (right before the stimulus needs to be delivered). In some variations the next stimulus or stimuli to be presented to a user can be queued up, ready for when they begin a study mode. In some variations multiple sets of stimuli can be queued up, and the selection of one or more of the stimuli is contingent upon other factors such as the time of day, location of the user, content to be studied, etc. In an advantageous embodiment, software algorithms to process or algorithmically select stimuli (i.e. to personalize them according to frequency component or the amount of time they are ramped on and off) can occur 'in the cloud' at a convenient time before a user enters a study mode (i.e. on an Amazon EC2 server according to a bid that runs it when server time is cheap such as in the middle of the night). In another embodiment of the invention, the learning database is configured to select a cue randomly, stochastically, or statistically.

In some variations a learning database system is configured so that a third party can select one or more contextual sensory stimuli. In various embodiments, the third party is a teacher, coach, friend, company (i.e. for marketing), or other entity, group, or individual. The invention may be further configured so that the third party can make the contextual sensory cue selection by communicating with the learning database. Communication with the learning database can occur via text message, tweet, API call, Internet form, voice-to-text, or other mode of communication. In some variations a third party is a company and the cue is or is related to a jingle or otherwise supports marketing efforts of the company and thus represents a sponsorship opportunity. In some variations a third party is an artist who selects specific cues to associate with their art (or which are part of their art, as for sound clips used by an electronic musician) so as to trigger a specific set of memories related to an artistic performance. In this way the experience of the artist's art has the potential for a further layer of control by the artist—not just what the audience experiences, but also what they retain over time. In an embodiment, the selection of one or more contextual sensory stimuli is 'crowdsourced'. A group of individuals selects a stimulus on behalf of the user.

In some variations the learning database generates a set of desired contextual sensory stimuli to present. In some cases, the members of this set may be prioritized concerning what sensory stimuli to present in which order. The learning database and memory enhancement system is further configured to assess the sensory stimulation hardware and related components available to present stimuli to a user at the requested time and determines which of the desired set of contextual sensory stimuli can be presented. In the case wherein some stimuli cannot be presented, the system will skip or deprioritize them for presentation at another time. These circumstances may occur for instance if a user has a speaker or headphones available to present an audio stimulus but no odorizers or similar hardware for presenting an olfactory stimulus. Accordingly, all olfactory stimuli that have been prioritized or scheduled for presentation will be skipped or delayed until another time when appropriate smell generating hardware is available. This embodiment of the invention would also be useful if a user has low fidelity headphones incapable of presenting a low (bass) tone effectively, so sounds that have dominant low frequency components would be skipped or delayed until another time when appropriate sound generation hardware is available.

In some embodiments of the invention, the contextual sensory cue delivered during sleep mode is a modified version of the cue presented during an earlier study mode period. In some variations the original stimulus is modified to improve the efficiency with which stimuli are delivered in one or more of the following ways: a stimulus that is temporally varying (e.g. a sound or spatiotemporal pattern of tactile stimulation) is sped up; one or more short clips are presented from a stimulus that is extended in time (e.g. a 10 minute environmental recording or song); a stimulus is masked or otherwise modifying a stimulus so that it is less likely to wake the user or another individual sleeping near the user (e.g. on a background of white noise); a stimulus is ramped up and down in intensity when it begins and ends; multiple stimuli delivered during an earlier study session are presented concurrently in a combined stimulus so that multiple memory traces are activated concurrently. A variation wherein two or more stimuli are combined may also be advantageous for tying related concepts together in memory. For instance, learning related equations about particle physics with two different sound cues, then tying these two equations together during sleep mode by playing the cues concurrently, overlapping in time, or subsequent to each other. In some instances, a desirable association between two related concepts is not emphasized during the initial learning of the material. For example, a student may be learning an exponential equation in a mathematics lecture and learning the growth rates of bacteria in a biology lab, but only emphasizes the association during sleep through presentation of combined stimuli. In one embodiment, sound cues are presented during sleep mode on an unobtrusive background that is minimally distracting such as white noise or another relaxing auditory stimulus that is unlikely to wake a user or other nearby sleeper.

Scheduling Re-Play of Stimuli

Described herein are systems and methods for selecting stimuli that have been previously presented during training for presentation again during sleep and scheduling of memory reactivation events across nights of sleep. Long-term use of a memory enhancement system based on sensory-tags presented to a user during study and re-presentation of these tags during sleep leads to a number of unexpected system design challenges. First, sleep is limited in time. Particular stages of sleep that may be conducive to memory consolidation (and enhancement of this process) are further limited. For instance, slow-wave sleep occurs during a minority of a sleep period—and is particularly limited in some individuals, including those with some sleep disorders, certain cognitive disorders (e.g. Alzheimer's disease and Down syndrome), and as a consequence of normal aging due to the known gradual decrease in the proportion of time spent in slow-wave sleep as individuals age. Due to the limited time spent in slow-wave sleep and other stages of sleep, systems for scheduling which stimuli to re-present are advantageous.

Optimal memory formation may require intermittent reinforcement. This feature of learning and studying is well known to psychologists, cognitive scientists, and neuroscientists but has not been previously considered in the context of modulation of memory consolidation during sleep. Thus, the learning database and scheduler system is configured in a particularly beneficial embodiment of the invention to intermittently reinforce memory consolidation by re-presenting contextual sensory stimuli presented during a (much) earlier study session. In an embodiment of the invention, a contextual sensory stimulus ('stimulus A') is associated with learned content during a particular study period by the user. In an embodiment of the invention, the learning database and scheduler system are configured to present 'stimulus A' during slow-wave sleep (or another phase of sleep) at a time chosen from the group of: a nap during the same day when the study session occurred during which 'stimulus A' was presented; a nap on a subsequent day after the study session occurred during which 'stimulus A' was presented; the first night of sleep on the evening immediately following the study session occurred during which 'stimulus A' was presented; or on a night a variable number of nights after the 'stimulus A' study session, where the amount of time between the study session and the first re-presentation of 'stimulus A' is chosen from the list consisting of: 2 nights, 3 nights, 4 nights, 5 nights, 6 nights, 7 nights, 8 nights, 9 nights, 10 nights, 2 weeks, 3 weeks, 4 weeks, 5 weeks, 6 weeks, 7 weeks, 8 weeks, 3 months, 6 months, 1 year or longer.

In some variations the learning database and scheduler system are configured to re-present one or more contextual sensory stimuli during sleep that were previously presented to the user during a study mode period. Re-presenting the same stimulus to trigger memory consolidation, memory re-consolidation, or disruption of memory consolidation or re-consolidation is a beneficial feature of the invention because systems configured in this manner (and methods for achieving this embodiment of the invention) enable more reliable or stronger memories to be stored by improving memory consolidation but do not require additional study sessions during wakefulness.

There are often large amounts of information to learn, consolidate, and retain, yet limited periods of sleep.

Everyday situations often require a large amount of information to be retained by the user. In such cases, the user may find himself/herself scheduling an overwhelming number of reinforcing stimuli, despite the limited amount of available slow-wave sleep for sleeping reinforcement. In an unmanaged situation, the desired sleep-reinforcing event may not occur within the desired time window for learning the information. Thus, systems and methods for determining how to schedule contextual sensory stimuli presented during a study session to be presented during sleep would be beneficial for making a broadly useful memory enhancement system that can be used over days, weeks, months, and years.

In some embodiments, the system tracks the number of awake learning events undertaken for each piece of information (when the user used a memory enhancement system in 'Study Mode'). In an embodiment, users assign priority to each piece of information learned or experienced through a ranking, scoring, or other prioritization system. In an embodiment, the user prioritizes information acquired using a tablet, mobile phone, web interface, or other software system. One system that has similar functionality for ranking and organizing information in this manner through a web browser or mobile device is Trello (www.trello.com). A component of the system described here is a scheduler to determine which contextual sensory stimuli to re-present during a particular sleep epoch. The schedule is optionally adjusted based on the rankings and prioritization given by the user. In alternative embodiments, prioritization of content for memory enhancement in a user is done by a third party individual, company, or service. For all learning content that had been previously associated with a contextual cue, the learning database is configured to store an association between the content and cue. In this manner, a user can rank the content for priority of learning without needing to be aware of the cues that had been associated during study with content.

Based on the prioritization system chosen by or on behalf of the user, the learning database is queried for the associated contextual sensory cue presented and that cue is presented to the sleeping user during an appropriate stage of sleep according to the order defined by the prioritized learning list. In some circumstances, de-prioritizing memories that do not need to undergo enhanced memory consolidation during sleep is beneficial. De-prioritization of content can be done for a variety of reasons, including: if the user already has formed a strong memory (has learned) the related content; or if the content is less important than other content for the user to retain (e.g. for material a teacher has told the student will not be tested).

In some variations the system is configured to alert the user if any stimuli have not been re-presented during sleep over a period of time. This situation would occur for instance if there is a backlog of sensory cues previously associated with learned content that has been classified as lower priority. In various embodiments, the period of time is chosen from the group consisting of: less than one day, more than 1 day, more than 2 days, more than 3 days, more than 4 days, more than 5 days, more than 6 days, more than 7 days, more than 2 weeks, more than 1 month, or longer. In some embodiments, the user creates an 'alert' or calendar entry for particular learned content. The alert or calendar entry would be used to schedule re-presentation of the contextual sensory cue to happen before a given date, on a given date, or after a given data. A user may want to have re-presentation occur before a test or quiz and would thus create a calendar entry the day or some fixed number of days before the quiz (but the user would be agnostic as to when during the period preceding the calendar entry the re-presentation event occurs). Alternatively, a user may want to have re-presentation occur on a given date, and the system would schedule that item to be a high priority cue for re-presentation during a sleep epoch on that day (or the night following that day). In optional embodiments of the invention, the system is configured to automatically generate an alert to the user if there are too many scheduled cues for re-presentation in a given period. In an alternative embodiment, the system is configured to suggest a bedtime or amount of sleep required in order to fulfill the full number of priority re-presentation events. In an embodiment, the system suggests to the user that they take a nap due to the large number of sensory re-presentation events scheduled. The alert generated by the system can optionally be sent by one or more methods chosen from the group of: email, phone call, voice message, text message, direct message tweet, or another form of communication. In another embodiment, a passive alert to sleep is presented to the user in the form of suggestive sensory stimuli. For example, a user that performs a fixed routine just prior to sleep, including using fragrant soap, may be alerted by the system to go to sleep by delivering a similar fragrant odor. In short, this is an alternate framework for considering what it means to have 'sleep debt'. The term 'sleep debt' is generally associated with the concept of amount or quality of sleep, but in this context is associated with not having sufficient sleep time for re-presenting contextual sensory stimuli.

Presenting a contextual sensory stimulus more than once during one or more epochs of slow-wave sleep (or another phase of sleep) or during one or more nights of sleep can be advantageous for further strengthening the memory consolidation process for the related learned content. The number of repeated presentations of a sensory stimulus is chosen from the group of more than once, more than twice, more than three times, more than four times, more than five times, more than 10 times, more than 15 times, more than 25 times, more than 50 times, more than 100 times, more than 500 times, more than 1000 times, more than 10000 times, or more frequently. In an embodiment, different modified versions of a contextual sensory stimulus or clips from a stimulus that is extended in time are presented. In this way, the triggering of particular learning content is repeated but the cue itself is slightly different and thus less susceptible to habituation by the appropriate sensory system or systems. In some embodiments, a contextual sensory stimulus associated with lower priority learned content is re-presented fewer times during one or more epochs of slow-wave sleep than it would otherwise have been.

In an embodiment, the learning database and/or scheduler is configured to automatically assign priority of learned content according to personalized criteria that can include demographic and other information (e.g. age, sex, IQ, academic strengths and weaknesses, interests, assignments (from work, school, etc) and other information).

As sleep is limited in time, some embodiments optimize the number of presentations delivered to a user.

Closed-loop feedback may be used. For example, in some variations the user is able to notify the scheduler system as to whether the desired memory has been successfully modulated at any time after the initial learning session for that memory. The scheduler subsequently alters the delivery schedule of the tagging 'stimulus A'. In the particular case of memory enhancement, the scheduler may perform either of: ceasing delivery of the 'stimulus A' (allowing other tagging stimuli to be presented during SWS), or increasing the frequency of planned instances when 'stimulus A' is to be delivered for passive maintenance of a memory. Alternatively, if the user reports failed memory enhancement, the scheduler can decrease the frequency of planned instances of 'stimulus A' delivery.

Closed-loop feedback—individualized scheduling—may also or alternatively be used. In some variations user reporting of successful and unsuccessful memory consolidation can be used by the scheduler to optimize the timing of stimulus delivery. Consistent user reporting of outcome allows the scheduler in desired instances to create a statistical model of outcome success as a function of various stimulation parameters, such as time of stimulus presentation, time intervals between stimulus presentation, as well as user physiological parameters, such as sleep quality, duration of sleep or nap, and heart rate. As a result of this statistical analysis, the scheduler can adjust the scheduled delivery of stimuli in a manner optimal for the user, given his prior performance history. In some embodiments, reporting of outcome can be done automatically such as via a self-testing program on a website or the reporting of outcome can be done by a third party such as a teacher or tutor.

Systems and Methods for Scheduling Sleep

An advantageous optional feature of the learning database and sensory cue selection and scheduling system may include the ability to 'schedule' sleep for a user. In some variations the system interfaces with a user's calendar via a Google calendar API, Microsoft Outlook, a personal assistant who manages the user's memory enhancement, or other calendaring system and 'schedule' a nap or longer (or shorter) night of sleep for a user in order to achieve particular memory enhancement effect or with the intention that the user will enter a particular phase of sleep for a certain amount of time.

One or more of the following factors, measurements, or user demographics can be used to further adjust the scheduler of sleep: (1) a user's studying and memory enhancement needs—during an intensive period of study (e.g., a recent law school graduate spending the summer studying for the bar exam) or during a period of time when re-activation of previously consolidated memories would be advantageous (e.g., for a student in the days or week before a final exam, such that previously enhanced memories from earlier in the semester can be further consolidated); (2) a user's recent or historical sleep, slow-wave sleep, or another sleep state as self-reported or measured by a sleep sensor component of a memory enhancement system or by another sleep measurement system or device; (3) a user's physiology, including one or more of measurement of brain rhythms, heart rate (and heart rate variability), galvanic skin response, breathing rate, pupil dilation, and other physiological measurements that can be used to infer or determine a user's cognitive, physiological, emotional, or attentional state with relation to memory encoding, consolidation, and retrieval; (4) a user's demographic information such as age, sex, health, weight, or other comorbidities that affect sleep or memory processes or both (sleep apnea, a sleep disorder, mild cognitive impairment, normal aging, Alzheimer's disease, other forms of dementia, stroke, chemotherapy treatment, radiation therapy, Down syndrome, attention-deficit hyperactivity disorder, etc); and (5) a third-party's needs for memory enhancement by the user, such as a teacher, tutor, corporate trainer, or military/first responder training or debriefing protocol.

Exemplary systems and methods for scheduling repetition of contextual sensory stimulus presentation during sleep are described herein. In some variations the learning database and scheduler system is configured to present a contextual sensory stimulus is presented multiple times in a single epoch of sleep. The number of times a stimulus is presented during a single night of sleep or epoch of a sleep stage during a night of sleep is generally chosen from the list of at least once, at least twice, at least three times, at least 4 times, at least 5 times, at least 10 times, at least 15 times, at least 25 times, at least 100 times, or more times, depending on the length of the night of sleep or sleep epoch and the length of time of a single sensory stimulus. In an embodiment, the learning database and scheduler system is configured to present a contextual sensory stimulus during multiple sleep epochs in a single night. Generally, there are more than one and less than 10 epochs of slow-wave sleep in a single night.

In some variations the learning database and scheduler system is configured to present multiple contextual sensory stimuli sequentially in a single epoch of slow-wave sleep or another sleep stage. The scheduler system can be optionally configured to deliver or trigger the delivery of sensory stimuli in an order chosen according to one or more of the following frameworks: (1) sensory stimuli presented according to the priority of the learned content associated with them during studying; (2) in the order in which the sensory stimuli were presented during studying; (3) in the reverse order which the sensory stimuli were presented during studying; (4) in an order that assigns a lower priority (later presentation) for sensory stimuli that were presented at the beginning of a study session due to the well-known 'Primacy Effect' wherein memories are stronger for items at the beginning of a list or study session; (5) in an order that assigns a lower priority (later presentation) for sensory stimuli that were presented at the end of a study session due to the well-known 'Recency Effect' wherein memories are stronger for items at the end of a list or study session; (6) in a random order; (7) in an order structured so as to achieve repetitions for a particular sensory stimulus or set of sensory stimuli several times in succession before moving on to a next sensory stimulus; or (8) ordering rules customizable by a user or third party via a user interface.

In embodiments wherein a contextual sensory stimulus that extends in time (generally a sound, spatiotemporal tactile stimulus, or visual stimulus) is delivered to a subject during study, the scheduler is appropriately configured for re-presentation of all or part of that cue during sleep. In an embodiment, the entire sensory cue is re-presented during slow-wave sleep or another sleep state. In some embodiments, the epoch of slow-wave sleep ends before the entire sensory cue has been presented, in which case the system can be configured to stop the replay of the sensory stimulus. In another embodiment, brief clips of the sensory stimulus are re-presented during sleep. The clips can be chosen to be from: the beginning, the end; key transition points in the sensory cue (e.g. for a song, at the beginning of a verse or a time when a saxophone solo occurs in a live jazz recording—these times periods can marked by a third party (e.g. hired via oDesk or Amazon Mechanical Turk), or the time periods can be detected algorithmically by analyzing the waveform of the song); random periods in the stimulus; or clips within the stimulus that have been shown by other users to be effective as sensory-tags for enhancing memory consolidation. In an embodiment, in various repetitions of the cue in a single night or across multiple nights can use different clips from the same sensory stimulus.

In some variations appropriate for use with both short and long sensory stimuli, processed versions of a stimulus are presented during the sleep phase. For instance, an audio file can be processed using dimensional reduction analysis techniques to identify the most salient aspects of the stimulus. This embodiment can also employ signal processing techniques for audio files that take advantage of what is known about human hearing, such as by using known audio compression techniques (e.g. mp3). Principal component analysis and Fourier transforms of the audio file could also be beneficial to use as stimuli.

In some embodiments, the scheduler is configured to adjust the salience or intensity of a contextual sensory stimulus. In some embodiments, optimization of the salience of intensity of a contextual sensory stimulus is done during study. Factors including the stimulus, user sensory thresholds, background noise, etc. can affect the required salience during both study modes and sleep modes. In an embodiment, the salience or intensity of a tone is adjusted across multiple presentations of a cue within one epoch of slow-wave sleep or across multiple epochs of SWS. For instance, for sounds the sound pressure level can be changed with each iteration of a sensory stimulus during study and/or sleep (e.g. the sound gets gradually louder until it reaches a predefined upper bound or the sound begins at silence or a minimum loudness, then ramps up in sound pressure level to a predefined upper limit). For smells, the amount of odorant released can be adjusted to affect the salience or intensity of a contextual sensory cue.

In variations wherein a contextual sensory stimulus that extends in time (generally a sound, spatiotemporal tactile stimulus, or visual stimulus) is delivered to a subject during study, the scheduler is appropriately configured for re-presentation of all or part of that cue during sleep. In an embodiment, the entire sensory cue is re-presented during slow-wave sleep or another sleep state. In some embodiments, the epoch of slow-wave sleep ends before the entire sensory cue has been presented, in which case the system can be configured to stop the replay of the sensory stimulus. In another embodiment, brief clips of the sensory stimulus are re-presented during sleep. The clips can be chosen to be from: the beginning, the end; key transition points in the sensory cue (e.g. for a song, at the beginning of a verse or a time when a saxophone solo occurs in a live jazz recording—these times periods can marked by a third party (e.g. hired via oDesk or Amazon Mechanical Turk), or the time periods can be detected algorithmically by analyzing the waveform of the song); random periods in the stimulus; or clips within the stimulus that have been shown by other users to be effective as sensory-tags for enhancing memory consolidation. In some variations various repetitions of the cue in a single night or across multiple nights can use different clips from the same sensory stimulus.

In variations appropriate for use with both short and long sensory stimuli, processed versions of a stimulus may be presented during the sleep phase. For instance, an audio file can be processed using dimensional reduction analysis techniques to identify the most salient aspects of the stimulus. This embodiment can also employ signal processing techniques for audio files that take advantage of what is known about human hearing, such as by using known audio compression techniques (e.g. mp3). Principal component analysis and Fourier transforms of the audio file could also be beneficial to use as stimuli.

Systems and Method for Use with Electronic Learning Media

As mentioned above, the apparatus, systems and methods described herein may be used with any appropriate source of learning or training, including electronic book readers and other electronic media, such as web pages/browsers. A system for improving memory having a training mode and a sleep consolidation mode may be configured to be used for enhanced learning of electronic media, where the form of electronic media is selected from the group including, but not limited to: electronic books ('e-books' or 'e-readers'); text content served via the Internet to a computing device; audio recordings played by a computerized system; video recordings played by a computerized system; classroom lectures; dynamic or interactive software systems (i.e. games); electronic braille readers; text-to-speech audio; and other forms of multimedia including text, images, audio, and video.

In particular, the invention can be used to modulate how electronic media material is learned by enhancing or disrupting memories associated with all or part of the electronic media material. In an advantageous embodiment, the electronic media can be material accessed on a website, mobile/tablet application, or e-reader.

In contrast to traditional books, electronic media accessed through the Internet (or via an Internet-enabled device) may be particularly advantageous, because the memory improvement system can be configured to record information to a computer memory or remote server about the content experienced, as well as the time, location, presented sensory stimuli, and other meta-data about the training session. These data are useful for providing feedback to the user or for reviewing previously experienced material.

The system may be configured so that the experienced electronic media represents a training session. In order to form an association between the content learned during a training session, the system enters training mode and presents one or more sensory stimuli concurrently with a user's experience (e.g., reading, watching, listening) of selected electronic media. The presented sensory stimuli are then presented to the user when the user is in a specified sleep state.

Sensory stimuli can be of any modality. Beneficial sensory modalities can be chosen depending on the form of the electronic media being experienced. For instance, auditory cues may be presented either continuously or intermittently while the user experiences textual and/or visual electronic media. Auditory cues may also be advantageous for electronic media that takes the form of audio recordings or video recordings, but an auditory cue needs to be selected to be one that is nondisruptive to hearing the audio portions of the experienced electronic media.

Some modalities of sensory stimuli presented during experience of electronic media require additional hardware. Olfactory stimuli can be delivered through an odorizer, volatile odor, candle, or other system. Tactile stimuli can be presented through a wearable array of buzzers or other tactile transducers. In some embodiments that require additional hardware for creating sensory stimuli, the hardware is manually controlled by the user. In other embodiments that require additional hardware for creating sensory stimuli, the hardware is configured to be controlled by a computer, e-reader, mobile device, smartphone, or other computerized system via a wired or wireless protocol to define when the odor is released and related parameters.

The system may register the sensory stimuli that are presented during a training session and schedules them to be presented again to the sleeping user during a specified sleep stage during a period of sleep that follows the training session, as mentioned above.

In some variations, the system is configured to enhance learning of content experienced in e-books, including textbooks, works of non-fiction, works of fiction, and volumes focused on visual experience such as graphic novels or books about design, art, or photography.

In some variations of the invention an e-book is experienced by a user by a computerized system chosen from the list including, but not limited to: dedicated e-reader such as an Amazon Kindle or Barnes and Noble Nook; an app running on a tablet, mobile device, or smartphone (e.g. Kindle app on an iPhone); a web-interface on a desktop computer, laptop, tablet, mobile device, or smartphone; or standalone software for aggregating and/or managing content.

A useful feature of the invention may be that sensory stimuli, experienced content, and metadata may be uploaded to a company server and available for feedback to the user, improvement of user experience, sharing via social media, and data mining.

Another useful optional feature of the system is automatic recognition that a user has experienced an instance of electronic media during a previous training session. In short, a user is reviewing material. Thus, the system may detect "review" versus novel learning. In this case, the same sensory cue may be automatically presented, if possible given sensory transducers available at that time—e.g. if the user had previously experienced an olfactory cue and an appropriate olfactory transducer is available when material is reviewed, then the same or similar olfactory cue is presented; however if an appropriate olfactory cue cannot be generated during the review of previously experienced material and an alternative transducer is available (e.g., for sound), then a new stimulus is presented. In this way, a stronger association can be formed by re-presenting a same or largely similar sensory stimulus.

Thus, for example, any of the apparatus and systems described herein may be configured to integrate training mode functionality with third-party electronic media content experienced via the Internet on a website, a mobile or tablet 'app', software programs running on a desktop or laptop computer, or standalone hardware. The may be beneficial because it enables a user to enhance or disrupt memories of their choosing experienced through third party software and/or hardware. In various advantageous embodiments, a plug-in, API, bookmarklet, widget, software package, software library, or other software architecture is used to integrate training mode functionality with third-party electronic media.

This embodiment may also add an important portability and flexibility to a memory modulation system by permitting its integration with content experienced via a web browser, content aggregator, or other appropriate software (e.g., Evernote).

Optionally, integration can occur by having an app, plug-in, or other software structure running as a background process when a user accesses content on a third-party site. Optionally, the app runs as a background process on an e-book, mobile device, tablet, smartphone, or other electronic system.

The following examples describe illustrative examples of the invention. These examples are not exhaustive, and may include any additional features or elements described herein. In addition, additional or alternatively configurations and methods of operation are possible, and may be reasonably understood from the disclosure herein.

Example 6

Electronic Media

Sensory cues can be pre-defined for particular electronic media and automatically presented to the user as they experience the chosen content during a training session. Auditory, visual, and tactile cues are easily controlled in the temporal domain and thus advantageous modalities for being pre-defined for a particular electronic media or e-book.

Optionally, sensory cues are configured to occur intermittently as a user experiences an e-book, audio recording, video recording, or other instance of electronic media. By pre-defining the cues for particular content, important portions of content can be preferentially tagged by sensory stimuli. For instance, a new set of sensory stimuli is presented for a summary section at the end of each chapter of a textbook. Audio-linked e-books are available for instance through the company 'Booktrack'.

For audio recordings and video recordings, the playback rate is known, so sensory stimuli can be selected to match the duration of the electronic media. Further, sensory stimuli can be selected or constructed to have thematic elements occurring concurrently with salient or informative portions of the electronic media so that these sections can be prioritized for reactivation during sleep.

For text content, different users read at different speeds, meaning that sensory stimuli cannot be perfectly aligned with the content. In an embodiment when a user reads text (and/or views images), sensory stimuli are constructed or selected to be sufficiently long such that it does not matter how long a user takes to get through a section. If they move to a new section of content, then the system skips to a next track, keeping a record of which portions of the cue were presented. The system only replays the portion of sensory cue they actually experienced during a training session as a sleep sound.

Optionally, the system can be configured to be adaptive, for instance by applying a machine learning algorithm to estimate the speed with which they get through material of a particular type, difficulty, or area of expertise—and use the estimate of reading speed to select sensory stimuli of appropriate duration or structure.

Optionally, the system can be configured by a user by selecting an estimated reading speed (i.e. in words per minute). The reading speed is used by the system to estimate how long a user will require to get through a section, defining the duration or structure of sensory stimulus selected.

Optionally, eye tracking can be used to determine a user's progress in reading text. Alternatively, a user can indicate their position within text by a touch screen interaction, by moving a mouse, pressing a mouse button, by a keyboard interface, or by remote control. Speed reading apps present one/few word(s) at a time, so the stimulus coordination app can know exactly what the user is currently learning. For example ReadQuick: http://mashable.com/2012/08/31/readquick-review/

Optionally, if a sensory stimulus finishes before a user completes a section, a second sensory stimulus is selected and presented.

Optionally, a repeating sensory feature such as a melodic theme or rhythm for an auditory stimulus can be presented whenever a particular concept or topic occurs in the experienced multimedia material.

This feature may be advantageous because it partially circumvents the limited period when a specified sleep stage occurs (e.g. slow-wave sleep, which occurs from 10 s of minutes per night to a few hours per night). The limited amount of a specified sleep stage limits the time when sensory stimuli can be presented during sleep and limits how many memories can be processed during sleep. By only replaying the thematic element of a sensory stimulus, more content can be processed during sleep due to associated with a smaller number of cues.

Optionally, unique sensory stimuli are presented when a user reads a specific page, paragraph, or set of words. For example, as a desired content page is approached the sound of a wrinkle may be played.

Example 7

Electronic Playlist

In one variation, a user chooses her own playlist of auditory stimuli (i.e. sounds). In another variation, a user selects one or more genres of music or artists that they enjoy to be the basis of which auditory cues are presented. Any software for playing audio files on electronic media can be used, including streaming web audio (e.g., Rdio, Spotify, Pandora, or SoundCloud), audio stored locally on a user's hardware (e.g. iTunes), audio played from physical media (e.g. played via a flash drive, compact disc, or record player), or personal music stored in the cloud (e.g. iCloud or Amazon Cloud Player).

Optionally, a user can enter their login credentials for a third party site to allow the memory modulation system to access their music library or other data.

Optionally, the system can keep track for a user what content has been presented during a previous training session so that a unique cue is available for a new training session.

Optionally, the system is configured to make an API call to skip to a next audio recording (e.g. 'track') or select a new audio recording.

In some cases, when a user selects her own playlist, experienced electronic media material cannot be aligned to the content and/or structure of the learned material during a training session because the audio files are not matched to the length of time needed to experience the learned material. Optionally, a user can manually move on to a new track for a new section of material. In this case, the system is configured to store the portion of the audio file that was presented so that non-presented portions of the song are not replayed to the user during sleep.

Example 8

Multimedia Learning Experience

If learning experience on e-book or other platform involves video with sound or audio, then (if using auditory or visual cues) the cues could distract from the experience of the content. In some variations, the system is configured to automatically recognize the format of the electronic media and deliver audio stimuli designed to be nondisruptive to hearing the sounds of the audio and/or video content.

Ambient music and structured white noise are examples of types of auditory cues that would be minimally disruptive to experienced electronic media that incorporates an auditory component.

For instance, a video recording of a lecture requires that a student hear the lecturer's voice. The system may recognize that the learning content has an auditory component based on the file type, metadata, or other identifier of the electronic media, then selects an ambient music stimulus to play at a background sound level that does not distract the user from hearing the lecturer's voice on the video recording.

Thus, in any of the variations described above, the system may be used in conjunction with electronic media; further, the system may tailor the sensory stimuli used based on the content of the electronic media. Thus, the system may pre-review or analyze the electronic media in order to determine the sensory stimuli to apply. For example, the system (e.g., media analysis module of the system) may analyze the electronic media to determine one or more of: (1) the type of sensory stimuli (e.g., sense modality and/or particular sensory stimuli within a sensory modality) based on the content of the electronic media; (2) the duration of the sensory stimuli based on the pacing/duration of the electronic media; (3) the volume of the sensory stimuli (based on overlap with other media within the sensory modality of the sensory stimuli, etc.

From the foregoing it will be seen that this invention is one well adapted to attain all ends and objects hereinabove set forth together with the other advantages which are obvious and which are inherent to the structure. It will be understood that certain features and subcombinations are of utility and may be employed without reference to other features and subcombinations. This is contemplated by and is within the scope of the claims. Since many possible embodiments may be made without departing from the scope thereof, it is to be understood that all matter herein set forth or shown in the accompanying drawings is to be interpreted as illustrative, and not in a limiting sense.

What is claimed is:

1. A system for improving learning, memory, or learning and memory from an electronic media, the system having a training mode and a sleep consolidation mode, the system comprising:
   a sleep monitor configured to monitor a user's sleep state;
   a sensory stimulator configured to provide a plurality of distinct sensory stimuli based on the electronic media;
   a controller comprising control logic configured to select a sensory stimulus for a specific training session based on the content of the electronic media, and to control the application of the sensory stimulus, wherein the controller receives information on the user's sleep state from the sleep monitor, and controls the sensory stimulator to apply the contextual sensory stimulus from the specific training session according to a training schedule when the user is experiencing a specified sleep stage during a sleep consolidation mode; and
   a learning database configured to be populated with training content and sensory stimuli co-presented with the training content,
   wherein the controller is configured to determine which sensory stimuli to use based on the electronic media.

2. The system of claim 1, wherein the sensory stimulator is configured to provide an ambient sensory stimulus recorded during the training session.

3. The system of claim 1, wherein the controller is configured to determine which sensory stimuli to use based on the content of the electronic media.

4. The system of claim 1, wherein the controller is configured to determine how to apply the sensory stimuli based on the content of the electronic media.

5. The system of claim 1, wherein the controller is configured to determine which sensory stimuli to use based on the structure of the electronic media.

6. The system of claim 1, further comprising a memory configured to store information that indicates one or more of which sensory stimuli have been applied for specific training sessions, the sleep state of user, and completion of application of a sensory stimulus during a sleep consolidation mode following a specific training session.

7. The system of claim 1, wherein the sensory stimulator is configured to deliver one or more of: olfactory stimuli, auditory stimuli and tactile stimuli.

8. The system of claim 1, wherein the electronic media comprises an electronic book.

9. The system of claim 1, further comprising a communications module coupled to the controller configured to allow communication with a remote site.

10. The system of claim 1, wherein the control logic comprises an application configured to be executed on a mobile device.

11. The system of claim 1, further comprising an analysis module configured to pre-analyze the electronic media to determine a sensory stimuli to apply.

12. A portable user-controllable device for improving learning and memory from an electronic media, the device comprising:
- a user interface comprising a control allowing a user to place the device into a training mode before the user experiences the electronic media;
- a sensory stimulator configured to present a plurality of distinct sensory stimuli concurrently with a user's experience of the electronic media;
- sleep monitoring logic configured to determine when the user is in a specified sleep state; and
- a controller comprising control logic configured to determine a sensory stimulus based on the electronic media for a particular training session; wherein the controller is further configured to reapply the specific sensory stimulus when the user is in the specified sleep state following the training session;
- wherein the controller is configured to determine which sensory stimuli to use based on the content, structure or content and structure of the electronic media.

13. The device of claim 12, wherein the sleep monitoring logic is configured to determine when the user is in a specific sleep state using user motion and heart rate.

14. The device of claim 12, wherein the control logic comprises a set of distinct sensory stimuli to be presented during a particular training session.

15. The device of claim 12, wherein the sensory stimulator is configured to deliver one or more of olfactory stimuli, auditory stimuli, and tactile stimuli.

* * * * *